(12) United States Patent
Dietliker et al.

(10) Patent No.: US 9,199,934 B2
(45) Date of Patent: Dec. 1, 2015

(54) ALPHA-HYDROXYKETONES

(75) Inventors: Kurt Dietliker, Allschwil (CH); Peter Murer, Oberwil (CH); Rinaldo Hüsler, Basel (CH); Tunja Jung, Rheinfelden-Herten (DE)

(73) Assignee: BASF SE, Ludwigshafen (DE)

( * ) Notice: Subject to any disclaimer, the term of this patent is extended or adjusted under 35 U.S.C. 154(b) by 684 days.

(21) Appl. No.: 12/593,025

(22) PCT Filed: Mar. 25, 2008

(86) PCT No.: PCT/EP2008/053458
§ 371 (c)(1),
(2), (4) Date: Sep. 25, 2009

(87) PCT Pub. No.: WO2008/122504
PCT Pub. Date: Oct. 16, 2008

(65) Prior Publication Data
US 2010/0104979 A1    Apr. 29, 2010

(30) Foreign Application Priority Data
Apr. 4, 2007 (EP) .................................... 07105642

(51) Int. Cl.
| | | |
|---|---|---|
| *G03F 7/004* | (2006.01) | |
| *C07C 69/95* | (2006.01) | |
| *C07D 307/00* | (2006.01) | |
| *C07D 211/32* | (2006.01) | |
| *G03F 7/38* | (2006.01) | |
| *G03F 7/40* | (2006.01) | |
| *C07C 49/83* | (2006.01) | |
| *C07C 49/835* | (2006.01) | |
| *C07C 49/84* | (2006.01) | |
| *C07C 62/38* | (2006.01) | |
| *C07C 69/757* | (2006.01) | |
| *C07C 219/12* | (2006.01) | |
| *C07C 235/82* | (2006.01) | |
| *C07D 295/185* | (2006.01) | |
| *C07D 305/12* | (2006.01) | |
| *C07F 7/08* | (2006.01) | |
| *C07F 7/18* | (2006.01) | |

(52) U.S. Cl.
CPC .............. *C07D 211/32* (2013.01); *C07C 49/83* (2013.01); *C07C 49/835* (2013.01); *C07C 49/84* (2013.01); *C07C 62/38* (2013.01); *C07C 69/757* (2013.01); *C07C 219/12* (2013.01); *C07C 235/82* (2013.01); *C07D 295/185* (2013.01); *C07D 305/12* (2013.01); *C07F 7/0836* (2013.01); *C07F 7/0854* (2013.01); *C07F 7/1868* (2013.01); *G03F 7/004* (2013.01); *G03F 7/38* (2013.01); *G03F 7/40* (2013.01); *C07C 2101/14* (2013.01)

(58) Field of Classification Search
CPC  C07C 2101/14; C07C 219/12; C07C 235/82; C07C 49/83; C07C 49/835; C07C 49/84; C07C 62/38; C07C 69/757; C07D 211/32; C07D 295/185; C07D 305/12; G03F 7/004; G03F 7/38; G03F 7/40
USPC ........ 430/270.1, 302, 913, 281.1, 286.1, 927, 430/330, 331, 944, 945; 560/53, 54
See application file for complete search history.

(56) References Cited

U.S. PATENT DOCUMENTS

| | | | |
|---|---|---|---|
| 4,318,791 A | 3/1982 | Felder et al. | |
| 4,347,111 A | 8/1982 | Gehlhaus et al. | |

(Continued)

FOREIGN PATENT DOCUMENTS

GB          2259704 A        3/1993

OTHER PUBLICATIONS

Kohler et al, "The Reactions of Certain Gamma Ketonic Acids. V. Ketonic Beta Lactones and the Walden Inversion", Journal of the American Chemical Society, 1938, 60 (9), pp. 2142-2148.*

*Primary Examiner* — Amanda C Walke
(74) *Attorney, Agent, or Firm* — Shruti Costales

(57) ABSTRACT

Compounds of the Formula (I) wherein x is an integer from 1-4; p is an integer from 1-3; q is an integer from 0-3; Ar is phenyl, naphthyl, anthryl or phenanthryl each of which optionally is substituted by one or more Cl, CN, $OR_5$, $C_3$-$C_5$alkenyl or $C_1$-$C_6$alkyl which optionally is substituted by one or more $OR_6$, COOR or halogen; $R_1$ if x is 1, is $OR_7$, O—$X^+$, $NR_8R_9$, $C_1$-$C_{20}$alkyl optionally substituted by one or more $COOR_{10}$, or is $C_2$-$C_{20}$alkyl interrupted by one or more O, or is $C_2$-$C_5$alkenyl or phenyl-$C_1$-$C_4$alkyl; $R_1$ if x is 2, is for example $C_1$-$C_{20}$alkylene; $R_1$ if x is 3, is for example a trivalent radical; $R_1$ if x is 4, is for example a tetravalent radical; $R_2$ and $R_3$ are hydrogen or $C_1$-$C_8$alkyl, or $R_2$ and $R_3$ together are O, $C_1$-$C_3$alkylene or CH═CH; $R_4$ is $C_1$-$C_4$alkyl; $R_5$, $R_6$, $R_7$, $R_8$, $R_9$ and $R_{10}$ are for example hydrogen or $C_1$-$C_4$alkyl; and X is a x-valent cationic counter ion; are in particular suitable as photoinitiators for the curing with UV-A light (320-450 nm).

$$\left[ \mathrm{Ar} - \underset{\underset{O}{\parallel}}{\mathrm{C}} - \underset{\mathrm{HO}}{\overset{\overset{(R_4)_q}{|}}{\mathrm{C}}} \underset{\underset{O}{\parallel}}{\overset{\overset{(CH_2)_p}{|}}{\mathrm{C}}} R_2 \atop R_1 \right]_x \quad (I)$$

13 Claims, No Drawings

(56) References Cited

U.S. PATENT DOCUMENTS

| | | | |
|---|---|---|---|
| 4,563,438 A | 1/1986 | Berner et al. | |
| 5,399,770 A | 3/1995 | Leppard et al. | |
| 6,090,236 A * | 7/2000 | Nohr et al. | 156/275.5 |
| 6,251,962 B1 * | 6/2001 | Desobry | 522/18 |
| 6,361,925 B1 | 3/2002 | Leppard et al. | |
| 6,623,910 B2 * | 9/2003 | Shimada et al. | 430/270.1 |
| 7,084,183 B2 * | 8/2006 | Fuchs et al. | 522/36 |
| 2005/0004249 A1 | 1/2005 | Fuchs et al. | |
| 2006/0270748 A1 * | 11/2006 | Sommerlade et al. | 522/6 |
| 2009/0018354 A1 | 1/2009 | End et al. | |
| 2009/0104464 A1 * | 4/2009 | Galbo et al. | 428/461 |

* cited by examiner

ALPHA-HYDROXYKETONES

The present invention is directed to novel alpha-hydroxyketone compounds and their use a photoinitiators in polymerizable compositions.

Alpha-hydroxyketones are known as photoinitiators in the art. Such compounds are for example disclosed in U.S. Pat. No. 4,318,791, U.S. Pat. No. 4,347,111 or WO 03/040076. The use of alpha-hydroxyketone compounds in combination with other photoinitiators is for example known from U.S. Pat. No. 4,563,438, U.S. Pat. No. 6,361,925 or GB 2259704.

Alpha-hydroxyketone type photoinitiators are efficient photoinitiators for clear coatings using UV light of wavelengths <320 nm (UV-C, UV-B). Further, said initiators provide good surface cure, while for example in formulations containing light stabilizer packages or pigments through cure often is insufficient. So far the alpha-hydroxyketone type compounds in order to achieve a sufficient through cure therefore are used in combination with a photoinitiator absorbing at longer wavelengths, e.g. a mono- or bisacylphosphine oxide.

Surprisingly, it has now been found, that a new type of α-hydroxyketones, although possessing an absorption that is blue-shifted compared to acylphosphine oxides or other UV-A photoinitiators, is very reactive upon irradiation with UV-A light so that efficient through and surface cure under these conditions is provided. This feature is achieved due to the new substitution pattern and could not be expected in view of the performance of state-of-the-art α-hydroxyketone photoinitiators under identical conditions.

Subject of the invention therefore are compounds of the formula I, wherein

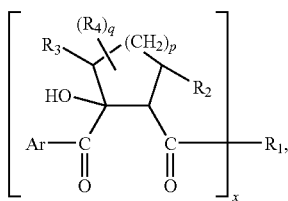

wherein
x is an integer from 1-4;
p is an integer from 1-3;
q is an integer from 0-3;
Ar is phenyl, naphthyl, anthryl or phenanthryl each of which optionally is substituted by one or more Cl, CN, $OR_5$, $C_3$-$C_5$alkenyl or $C_1$-$C_6$alkyl which optionally is substituted by one or more $OR_6$, $COOR_6$ or halogen;
$R_1$ if x is 1, is $OR_7$, $O^-X^+$, $NR_8R_9$, $C_1$-$C_{20}$alkyl optionally substituted by one or more $COOR_{10}$, or is $C_2$-$C_{20}$alkyl interrupted by one ore more O, or is $C_2$-$C_5$alkenyl or phenyl-$C_1$-$C_4$alkyl;
$R_1$ if x is 2, is $C_1$-$C_{20}$alkylene, $C_2$-$C_{20}$alkylene which optionally is interrupted by one or more O, or is O-A-O, O-A-$NR_{15}$, $NR_{15}$-A-O, $NR'_{15}$-A-$NR_{15}$, $NR_{15a}$-$A_1$-$NR_{15b}$ or $NR'_{15}$—$(CH_2)_{x'}$-A-$(CH_2)_{x'}$—$NR_{15}$ or is $O^-X^{2+}O^-$;
x' has one of the meanings as given for x;
$R_1$ if x is 3, is $N(R_{30}O)_3$—; $C_3$-$C_{20}$alkanetriyltrioxy which optionally is substituted by OH; $C_3$-$C_{20}$alkanetriyltriamino; a trivalent siloxane, or 3 $O^-X^{3+}$;
$R_1$ if x is 4, is $C_4$-$C_{20}$alkanetetrayltetraoxy optionally substituted by OH; $C_4$-$C_{20}$alkanetetrayltetraamino; a tetravalent siloxane; or 4 $O^-X^{4+}$;

$R_2$ and $R_3$ independently of one another are hydrogen or $C_1$-$C_8$alkyl, or $R_2$ and $R_3$ together are O, $C_1$-$C_3$alkylene or CH=CH;
$R_4$ is $C_1$-$C_4$alkyl;
$R_5$ is hydrogen, $C_1$-$C_4$alkyl, phenyl which optionally is substituted by one or more $C_1$-$C_4$alkyl, $C_1$-$C_4$alkoxy or halogen; or is $(C_2$-$C_6$alkyleneO$)_n$—$R_6$;
n is an integer from 1-20;
$R_6$ is hydrogen, $C_1$-$C_4$alkyl, $C_2$-$C_5$alkenyl or $C_2$-$C_6$alkanoyl;
$R_7$ is hydrogen, $C_2$-$C_5$alkenyl, $C_2$-$C_{20}$alkyl which optionally is substituted by one or more OH, $NR_{11}R_{12}$ or $Si(R_{14})_y(OR_{13})_z$; or is $C_2$-$C_{20}$alkyl which is interrupted by one ore more O or $NR_{15}$ and optionally is substituted by one or more OH, $NR_{11}R_{12}$ or $Si(R_{14})_y(OR_{13})_z$; or is $C_1$-$C_{20}$haloalkyl which optionally is substituted by one or more OH, $NR_{11}R_{12}$ or $Si(R_{14})_y(OR_{13})_z$; or is $C_2$-$C_{20}$haloalkyl which is interrupted by one or more O or $NR_{15}$;
$R_8$ and $R_9$ independently of one another are hydrogen, $C_1$-$C_{20}$alkyl; $C_1$-$C_8$alkyl substituted by CN, $COOR_{11}$ or $Si(R_{14})_y(OR_{13})_z$; $C_2$-$C_8$alkyl substituted by one or more $NR_{11}R_{12}$ or $OR_{11}$; or are $C_3$-$C_8$cycloalkyl, $C_3$-$C_5$alkenyl, phenyl-$C_1$-$C_4$alkyl or phenyl which optionally is substituted by $C_1$-$C_4$alkyl, $OR_{11}$ or halogen;
or $R_8$ and $R_9$ together are $C_3$-$C_7$alkylene which optionally is interrupted by one ore more O or $NR_{15}$ and which $C_3$-$C_7$alkylene or interrupted $C_3$-$C_7$alkylene optionally is substituted by one or more $C_1$-$C_4$alkyl or $COOR_{11}$;
z is an integer from 0-3;
y is an integer from 0-3, wherein the sum of y+z is 3;
$R_{10}$ is hydrogen or $C_1$-$C_4$alkyl;
$R_{11}$ and $R_{12}$ independently of one another are hydrogen or $C_1$-$C_4$alkyl which optionally is substituted by OH;
$R_{13}$ is hydrogen, $C_1$-$C_4$alkyl or $Si(R_{14})(R'_{14})(R''_{14})$;
$R_{14}$, $R'_{14}$ and $R''_{14}$ independently of each other are hydrogen or $C_1$-$C_4$alkyl;
$R_{15}$ and $R'_{15}$ independently of one another are hydrogen; $C_1$-$C_{20}$alkyl which optionally is substituted by OH, $COOR_{11}$ or CN; or is $C_2$-$C_{20}$alkyl which optionally is interrupted by one or more O; or is $C_3$-$C_5$alkenyl, phenyl-$C_1$-$C_4$alkyl, $C_1$-$C_8$alkanoyl or benzoyl;
$R_{15a}$ and $R_{15b}$ independently of one another form an aliphatic ring with a carbon atom of $A_1$ or $R_{15a}$ and $R_{15b}$ together are $C_1$-$C_3$alkylene;
$R_{30}$ is $C_2$-$C_8$-alkylene optionally interrupted by one or more O;
A is $C_2$-$C_{20}$alkylene which optionally is interrupted by one or more O or $NR_{15}$; $C_2$-$C_{20}$haloalkylene which optionally is interrupted by one or more O or $NR_{15}$; $C_5$-$C_{20}$cycloalkylene; or A is a divalent siloxane
$A_1$ is $C_2$-$C_{20}$alkylene which optionally is interrupted by one or more O or $NR_{15}$; and
X is a x-valent cationic counter ion.

The photoinitiators of the current invention are capable of providing both excellent surface cure and through-cure under UV-A irradiation. Hitherto the same effect was only achieved using combinations of mono- or bisacylphosphine oxide photoinitiator compounds (providing through-cure) and α-hydroxyketones (providing surface cure). Surprisingly both, better surface cure and through cure, are achieved if the new photoinitiators are used. Since the photoinitiators have a less red-shifted absorption than acylphosphine oxide structures, they imply less yellowing before and after cure than the latter, while maintaining an excellent performance regarding color changes upon long-time weathering.

$C_1$-$C_{20}$alkyl is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkyl.

Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_2$-$C_{20}$alkyl interrupted by one or more O is for example interrupted 1-9, 1-7 or once or twice by O. In case the groups are interrupted by more than one O, said O-atoms are separated from one another by at least one methylene group, i.e. the O-atoms are non-consecutive. Examples are the following structural units —$CH_2$—O—$CH_3$, —$CH_2CH_2$—O—$CH_2CH_3$, —[$CH_2CH_2O$]$_y$—$CH_3$, with y=1-9, —($CH_2CH_2O$)$_7CH_2CH_3$, —$CH_2$—$CH(CH_3)$—O—$CH_2$—$CH_2CH_3$, or —$CH_2$—$CH(CH_3)$—O—$CH_2CH_3$.

$C_1$-$C_{20}$Haloalkyl is, for example linear or branched $C_1$-$C_{18}$-, $C_1$-$C_{14}$-, $C_1$-$C_{12}$-, $C_1$-$C_8$-, $C_1$-$C_6$- or $C_1$-$C_4$haloalkyl and is $C_1$-$C_{20}$alkyl mono- or poly-substituted by halogen up to the exchange of all H-atoms by halogen. Examples are chloromethyl, trichloromethyl, trifluoromethyl or 2-bromopropyl, especially trifluoromethyl or trichloromethyl. $C_1$-$C_{20}$haloalkyl is for example $C_n[H_xHal_y]_{2n+1}$, wherein the sum of x+y=2n+1 and Hal, is halogen, preferably F.

$C_2$-$C_{20}$haloalkyl which is interrupted by one or more O or $NR_{15}$ corresponds to $C_2$-$C_{20}$alkyl which is interrupted by one or more O or $NR_{15}$, wherein the alkyl one or more H-atoms are replaced by halogen, similar as explained above.

$C_3$-$C_8$Cycloalkyl is for example cyclopropyl, cyclopentyl, cyclohexyl, cycloheptyl or cyclooctyl, especially cyclopentyl and cyclohexyl, preferably cyclohexyl.

$C_3$-$C_8$Cycloalkyl in the context of the present application is to be understood as alkyl which at least comprises one ring. Thus, for example methyl-cyclopentyl, methyl- or dimethyl-cyclohexyl are also meant to be covered by this term. Further examples are structures like

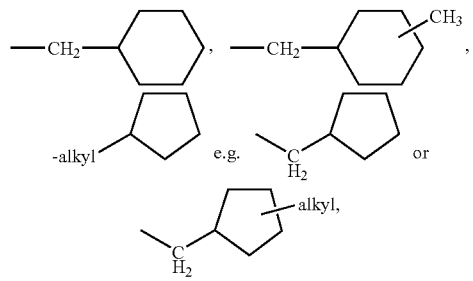

as well as bridged or fused ring systems, e.g.

etc. are also meant to be covered by the term.

$C_2$-$C_5$alkenyl and $C_3$-$C_5$alkenyl are mono or polyunsaturated, linear or branched and are for example $C_2$-$C_4$- or $C_3$-$C_4$alkenyl. Examples are allyl, methallyl, vinyl, 1,1-dimethylallyl, 1-butenyl, 3-butenyl, 2-butenyl or 1,3-pentadienyl, especially allyl or vinyl.

$C_1$-$C_4$alkoxy is linear or branched and is for example methoxy, ethoxy, propoxy, isopropoxy, n-butyloxy, sec-butyloxy, iso-butyloxy or tert-butyloxy, especially methoxy or ethoxy.

$C_1$-$C_8$alkanoyl is linear or branched and is, for example, $C_1$-$C_6$- or $C_1$-$C_4$alkanoyl or $C_4$-$C_8$- or $C_2$-$C_8$alkanoyl. Examples are formyl, acetyl, propionyl, butanoyl, isobutanoyl, pentanoyl, hexanoyl, heptanoyl or octanoyl, preferably acetyl.

Phenyl-$C_1$-$C_4$alkyl is for example benzyl, phenylethyl, α-methylbenzyl, phenylpropyl, phenylbutyl or α,α-dimethylbenzyl, especially benzyl. Substituted phenyl-$C_1$-$C_5$alkyl is substituted one to four times, for example once, twice or three times, especially twice or three times, preferably on the phenyl ring.

$C_1$-$C_{20}$alkylene is linear or branched alkylene, for example methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene or octadecylene. In particular, $C_1$-$C_{12}$alkylene, is for example ethylene, decylene,

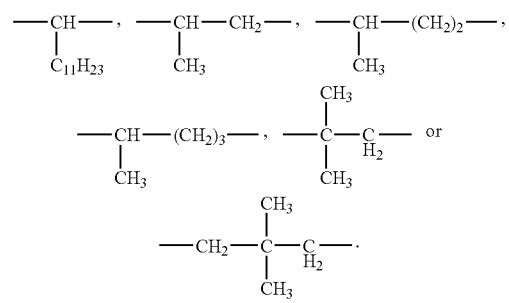

$C_2$-$C_{20}$ alkylene which is interrupted one or more times by —O— is for example, interrupted 1-9 times, for example 1-7 times or once or twice. This produces structural units such as, for example, —$CH_2$—O—$CH_2$—, —$CH_2CH_2$—O—$CH_2CH_2$—, —[$CH_2CH_2O$]$_y$—, —[$CH_2CH_2O$]$_y$—$CH_2$—, where y=1- 9, —($CH_2CH_2O$)$_7CH_2CH_2$—, —$CH_2$—$CH(CH_3)$—O—$CH_2$—$CH(CH_3)$— or —$CH_2$—$CH(CH_3)$—O—$CH_2$—$CH_2CH_2$—. The interrupting atoms are non-successive.

$C_2$-$C_{20}$haloalkylene is linear or branched $C_1$-$C_{18}$-, $C_1$-$C_{14}$-, $C_1$-$C_{12}$-, $C_1$-$C_8$-, $C_1$-$C_6$- or $C_1$-$C_4$haloalkylene, and denotes $C_1$-$C_{20}$alkylene wherein at least one H-atom is replaced by a halogen atom, that is the $C_1$-$C_{20}$alkylene is mono- or poly-substituted by halogen up to the exchange of all H-atoms by halogen.

$C_2$-$C_{20}$haloalkylene which is interrupted by one or more O or $NR_{15}$. The structures are in analogy to the interrupted $C_1$-$C_{20}$alkylene, provided that at least one H-atom is replaced by a halogen atom.

$C_5$-$C_{20}$cycloalkylene is, for example, cyclopentylene, cyclohexylene, cyclooctylene, cyclododecylene, especially cyclopentylene and cyclohexylene, preferably cyclohexylene. $C_5$-$C_{20}$Cycloalkylene in the context of the present application is also meant to represent for example, structural units such as

in which x' and y' independently of one another are 0-6 and the sum of x'+y' is ≤6, or

in which x' and y' independently of one another are 0-7 and the sum of x'+y' is ≤7. Further, bridged or fused ring systems are meant to be covered, as, for example

Halogen is fluorine, chlorine, bromine and iodine, especially fluorine, chlorine and bromine, preferably fluorine and chlorine.

Substituted phenyl is for example substituted one to five times, e.g. once, twice or three times, in particular once or twice at the phenyl ring.

If $R_2$ and $R_3$ together are O or $C_1$-$C_3$alkylene, they together denote for example O, $CH_2$, $CH_2CH_2$, $C(CH_3)_2$), resulting for example in the following structures

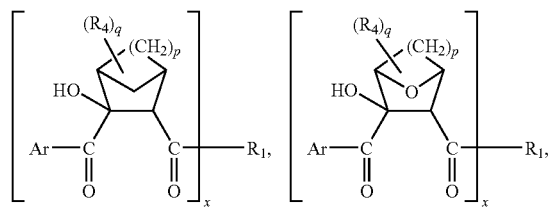

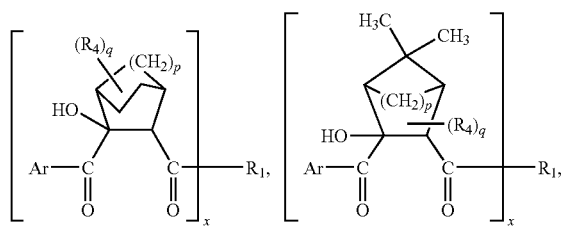

wherein $R_1$, $R_4$, Ar, p. q and x are as defined above.

If $R_8$ and $R_9$ together are $C_3$-$C_7$alkylene which optionally is interrupted by one ore more O or $NR_{15}$, saturated rings are formed, for example cyclohexyl, cyclopentyl, aziridine, oxirane, oxolane, azolidine=pyrrolidine, 1,3-diazine, 1,2-diazine, piperidine, morpholine rings,

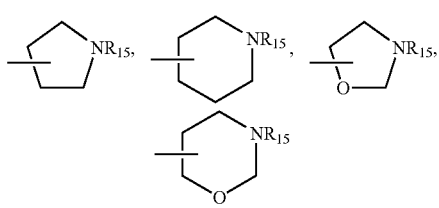

in particular morpholine rings.

If $R_{15a}$ and $R_{15b}$ independently of one another form an aliphatic ring with a carbon atom of $A_1$ for example structures as follow are formed

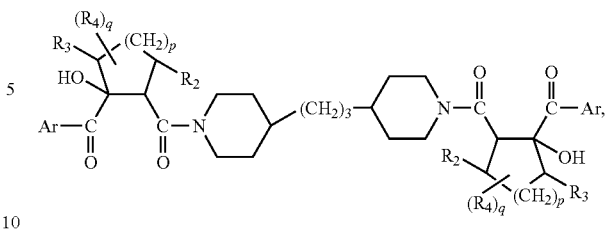

wherein Ar, $R_2$, $R_3$, $R_4$, q and p are as defined above.

If $R_{15a}$ and $R_{15b}$ together are $C_1$-$C_3$alkylene for example structures as follow are formed

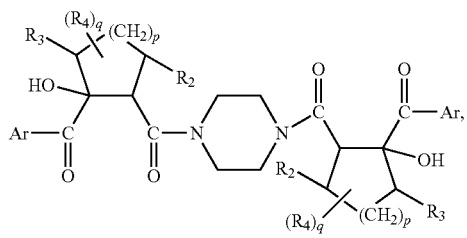

wherein Ar, $R_2$, $R_3$, $R_4$, q and p are as defined above.

A divalent siloxane is for example represented by the formula X

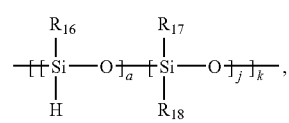

(X)

wherein the units

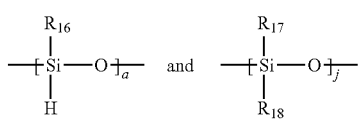

are arranged randomly or in blocks;

a is an integer from 0 to 100;

j is an integer from 0 to 10 000;

k is the integer 1 or 2;

$R_{16}$ $R_{17}$ and $R_{18}$ are each independently of the others $C_1$-$C_{18}$alkyl, phenyl, $C_2$-$C_6$hydroxyalkyl, $C_2$-$C_6$aminoalkyl, $C_5$-$C_8$cycloalkyl,

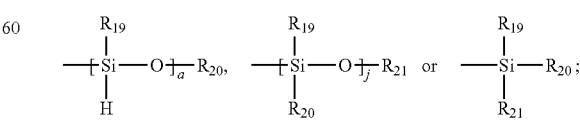

$R_{19}$, $R_{20}$ and $R_{21}$ independently of each other are $C_1$-$C_8$alkyl.

A trivalent siloxane is for example represented by the formula XI

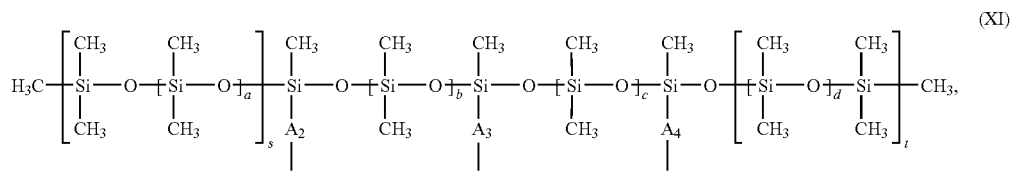

wherein $A_2$, $A_3$ and $A_4$ independently of each other are a direct bond, $C_1$-$C_{10}$alkylene which optionally is substituted by $[O(CH_2)_g-O]_h$ or $[O(CH_2)_g]_h$;

a, b, c and d independently of each other are an integer from 0 to 100;

s and t independently of each other are an integer 0 or 1;

g is an integer from 1-10;

h is an integer 1, 2 or 3.

A tetravalent siloxane is for example represented by the formula XII

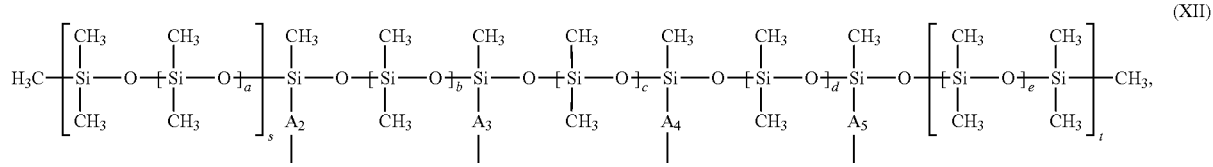

wherein $A_2$, $A_3$, $A_4$ and $A_5$ independently of each other are a direct bond, $C_1$-$C_{10}$alkylene which optionally is substituted by $[O(CH_2)_g-O]_h$ or $[O(CH_2)_g]_h$;

g is 1-10;

h is 1-3;

a, b, c, d and e independently of each another are an integer from 0 to 100;

s and t independently of each other are an integer 0 or 1;

$R_1$ when x is 3, as a trivalent linking group for example is $C_2$-$C_{20}$alkanetriyltrioxy optionally substituted by OH; such as for example

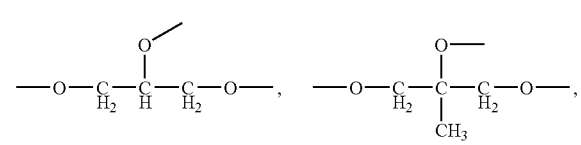

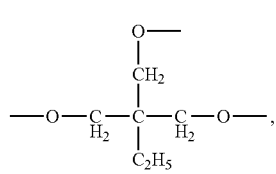

etc.;

$R_1$ when x is 3, as a trivalent linking group for example is $C_2$-$C_{20}$alkanetriyltriamino, such as for example

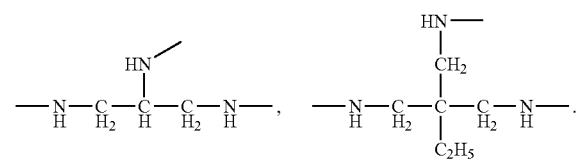

In the context of the present application this term is also meant to represent corresponding groups wherein one or all H-atom(s) of the amino group(s) is (are) replaced by $C_1$-$C_4$alkyl, e.g.

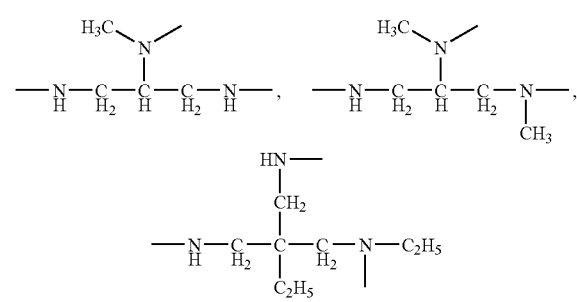

etc.

$R_1$ when x is 4, as a tetravalent linking group for example is $C_4$-$C_{20}$alkanetetrayltetraoxy optionally substituted by OH, such as for example

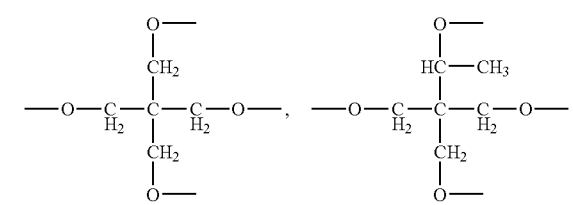

etc.;

$R_1$ when x is 4, as a tetravalent linking group for example is $C_4$-$C_{20}$alkanetetrayltetraamino, such as for example

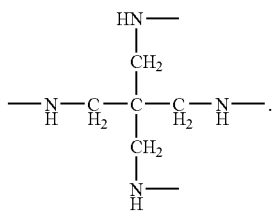

In the context of the present application this term is also meant to represent corresponding groups wherein one or all H-atom(s) of the amino group(s) is (are) replaced by $C_1$-$C_4$alkyl, e.g.

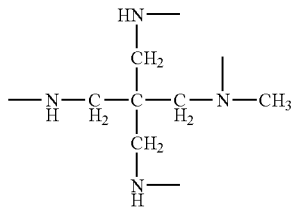

etc.

An x-valent cationic counter ion X is for example a cation with one, two, three or four positive charges.

Accordingly, X is for example a metal cation in the oxidation state +1, such as $Li^+$, $Na^+$, $K^+$, $Cs^+$, an "onium" cation, such as ammonium-, phosphonium-, iodonium- or sulfonium cation;

or X is a metal cation in the oxidation state +2, such as $Mg^{2+}$, $Ca^{2+}$, $Zn^{2+}$, $Cu^{2+}$, e.g. $Mg^{2+}$, $Ca^{2+}$, $Zn^{2+}$, preferably $Mg^{2+}$ or $Ca^{2+}$;

or X is a metal cation in the oxidation state +3, such as $Al^{3+}$, or a metal cation in the oxidation state +4, such as $Sn^{4+}$ or $Ti^{4+}$.

Examples for onium cations are ammonium, tetra-alkylammonium, tri-alkyl-aryl-ammonium, di-alkyl-di-aryl-ammonium, tri-aryl-alkyl-ammonium, tetra-aryl-ammonium, tetra-alkylphosphonium, tri-alkyl-aryl-phosphonium, di-alkyl-di-aryl-phosphonium, tri-aryl-alkyl-phosphonium, tetra-aryl-phosphonium.

E.g. $N^+R_{22}R_{23}R_{24}R_{25}$ or $P^+R_{22}R_{23}R_{24}R_{25}$, wherein $R_{22}$, $R_{23}$, $R_{24}$, $R_{25}$ independently of one another are hydrogen, phenyl, phenyl substituted by OH or $C_1$-$C_4$ alkyl or are $C_1$-$C_{20}$alkyl which optionally is substituted by OH, $C_1$-$C_4$alkoxy, $NR_{26}R_{27}$, benzoyl, phenyl or $Si(OH)_y(OC_1$-$C_4alkyl)_z$;

or two of $R_{22}$, $R_{23}$, $R_{24}$ or $R_{25}$ together form a 5- or 6-membered saturated or unsaturated ring, which optionally is fused onto other ring systems and which 5- or 6-membered saturated or unsaturated ring optionally includes additional heteroatoms, for example S, $NR_{15}$ or O;

$R_{26}$ and $R_{27}$ independently of one another are hydrogen or $C_1$-$C_4$alkyl which optionally is substituted by OH; and y and z independently of one another are 0-3, provided, that the sum of y+z is 3.

Examples of appropriate ammonium compounds are tetramethylammonium, tetraethylammonium, tetrapropylammonium, tetrabutylammonium, benzyltrimethylammonium, benzyltriethylammonium, benzyltripropylammonium and benzyltributylammonium. Tris($C_1$-$C_8$alkyl)-ammonium ions are also suitable, for example trimethylammonium.

Other suitable cationic counter ions are for example sulphonium or iodonium compounds, such as

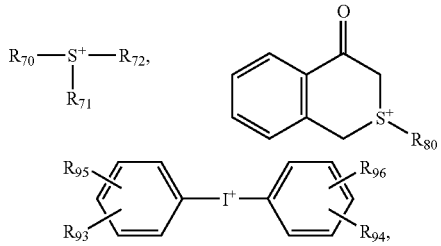

wherein $R_{70}$, $R_{71}$ and $R_{72}$ are each independently of the others $C_1$-$C_{20}$alkyl, unsubstituted phenyl, or phenyl substituted by —S-phenyl;

$R_{80}$ is $C_1$-$C_{12}$alkyl, especially ethyl, or is benzyl; and $R_{93}$, $R_{94}$, $R_{95}$ and $R_{96}$ are each independently of the other hydrogen, $C_1$-$C_{20}$alkyl, OH-substituted $C_1$-$C_{20}$alkyl, $C_1$-$C_{20}$alkoxy, OH-substituted $C_1$-$C_{20}$alkoxy, halogen, $C_2$-$C_{12}$alkenyl, cycloalkyl, especially methyl, isopropyl or isobutyl.

Also suitable as cationic counter ion X are dye cations. Examples are cations of triarylmethanes, for example malachite green, indolines, thiazines, for example methylene blue, xanthones, thioxanthones, oxazines, acridines, cyanines, rhodamines, phenazines, for example safranin. Also suitable are dyes containing acid groups, for example methyl red, ethyl orange, methyl orange, acid yellow, rosolic acid, phenol red, fluorescein, Rose Bengal, thymolphthalein monophosphoric acid, auramine O, cresyl violet, rhodamine B, brilliant green or variamine blue.

X is preferably $Li^+$, $Na^+$, $K^+$, $Cs^+$, $N^+R_{22}R_{23}R_{24}R_{25}$ or $P^+R_{22}R_{23}R_{24}R_{25}$; e.g. $Li^+$, $Na^+$, $K^+$, $N^+R_{22}R_{23}R_{24}R_{25}$ or $P^+R_{22}R_{23}R_{24}R_{25}$, in particular $Li^+$, $Na^+$, $K^+$ or $N^+R_{22}R_{23}R_{24}R_{25}$.

The term "optionally substituted" means, that the radical to which it refers is either unsubstituted or substituted.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preparation of Compounds of the Formula I.

The compounds of the formula I are for example prepared according to different methods from the corresponding aromatic carboxylic acid of formula (A)

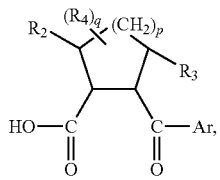

(A)

wherein p, q, $R_2$, $R_3$, $R_4$ and Ar are as defined above.

Preferably a compound (A), wherein $R_2$ and $R_3$ denote hydrogen, q is 0 and p is 2 is employed:

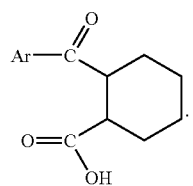

(A')

Method 1: Via Intermediates of C1 and C2 (See Below)

Step 1. An aromatic carboxylic acid of formula (A) is treated with halogen to give the halogenated intermediates (B1) or (B2) or (B3) or a mixture of (B1) and (B2) or a mixture of (B1) and (B3) or a mixture of (B1) and (B2) and (B3).

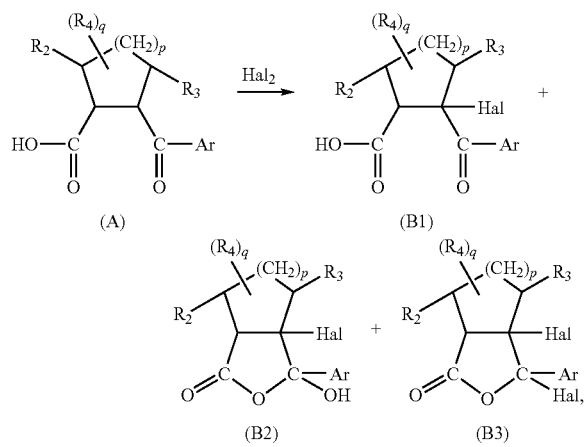

wherein $Hal_2$ denotes a halogen, e.g. $Cl_2$ or $Br_2$ and p, q, $R_2$, $R_3$, $R_4$ and Ar are as defined above.

Step 2. (B1), (B2), (B3) are transferred to the corresponding hydroxy-substituted compounds (C1) and (C2), e.g. by treating with a base:

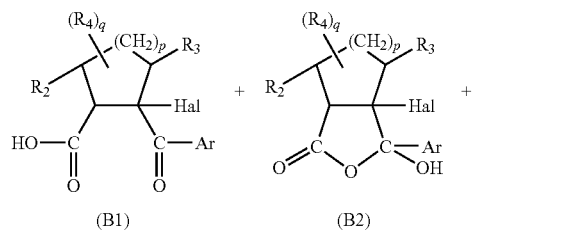

-continued

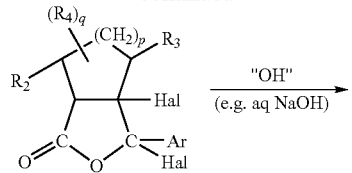

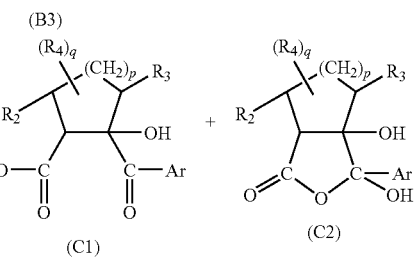

(C1) corresponds to a compound of the formula I, wherein $R_1$ is OR, with $R_7$ representing hydrogen.

Step 3. Finally, if $R_1$ in the compounds of the formula I is other than OR, with $R_7$ representing hydrogen, $R_1$ is then introduced via reaction with a suitable mono-, di-, tri-, or tetra-valent alcohol or amine $R_1(H)_x$, wherein $R_1$ and x are as defined above in an esterification reaction to give the compound of the formula I:

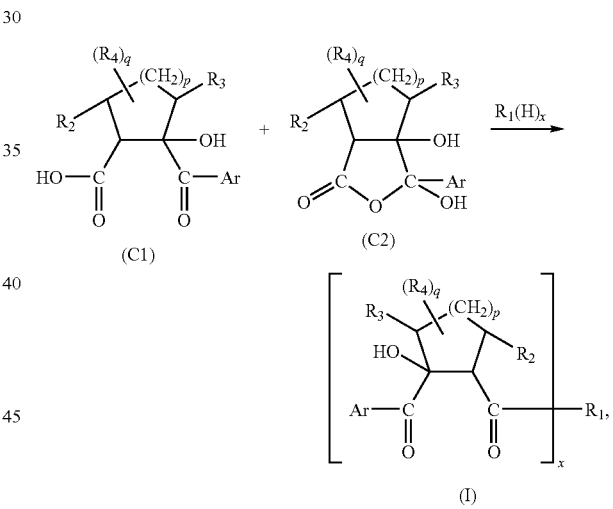

wherein x and $R_1$ are as defined above.

Method 2: Via Intermediates of Formula F (See Below)

Step 1. An aromatic carboxylic acid of formula (A) is treated with bromine in acetic anhydride/acetic acid to give the brominated intermediate (D):

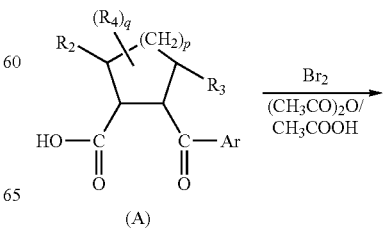

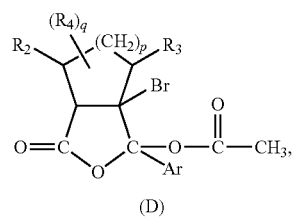

(D)

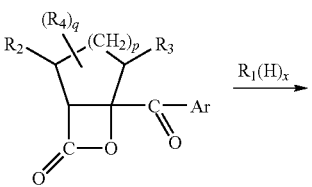

(F)

wherein p, q, $R_2$, $R_3$, $R_4$ and Ar are as defined above.

Step 2. The brominated intermediate (D) is treated with acid to give the intermediates (E1) or (E2) or a mixture of (E1) and (E2):

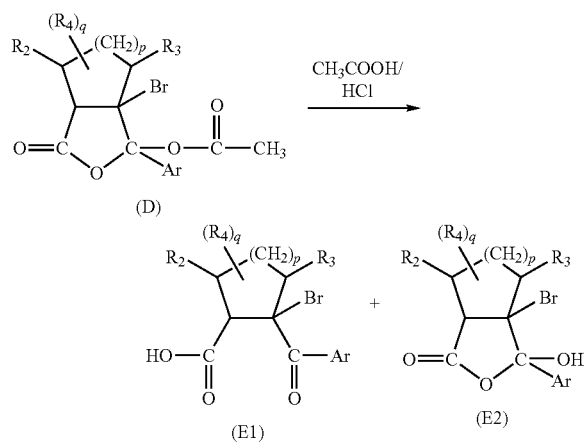

Step 3. Treatment of (E1) and (E2) with sodium hydrogencarbonate results in the formation of a lactone (F):

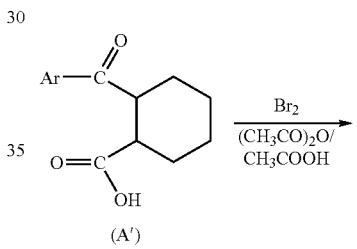

wherein x and $R_1$ are as defined above

Preferably, a compound (A') is used as the starting material, in particular in method 2, which results in the following reaction scheme for the preparation of the compounds of formula I, wherein p is 2, q is 0 and $R_2$ and $R_3$ denote hydrogen:

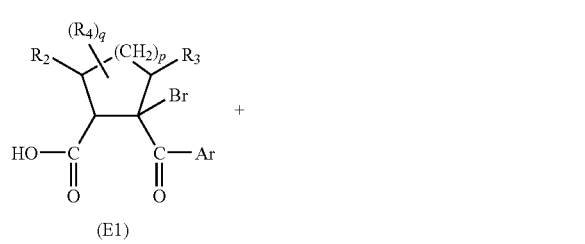

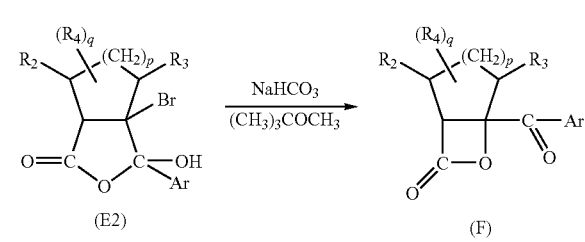

Step 4. The lactone of formula (F) is transferred to the compound of formula I by reacting it with a suitable mono-, di-, tri-, or tetra-valent alcohol or amine $R_1(H)_x$, wherein $R_1$ and x are as defined above, in an esterification reaction to introduce the group $R_1$:

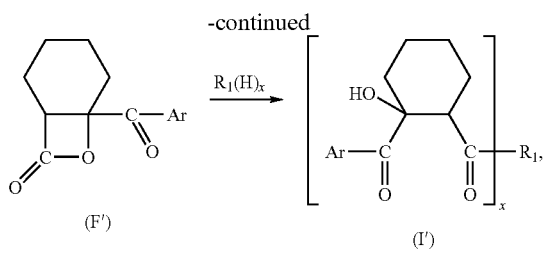

wherein Ar, $R_1$ and x are defined as above.

Preparation of the Intermediate Compounds of the Formula (A).

The starting compound for both methods 1 and 2, (A) or (A'), is for example prepared according to different reaction paths:

Path 1: Via Friedel-Crafts Reaction

An aromatic hydrocarbon (ArH) is reacted with a cyclic hydrocarbon anhydride (B) or (B') in a Friedel-Crafts reaction in the presence of a Friedel-Crafts catalyst to give the corresponding aromatic carboxylic acid (A) or (A'), respectively:

1.1:

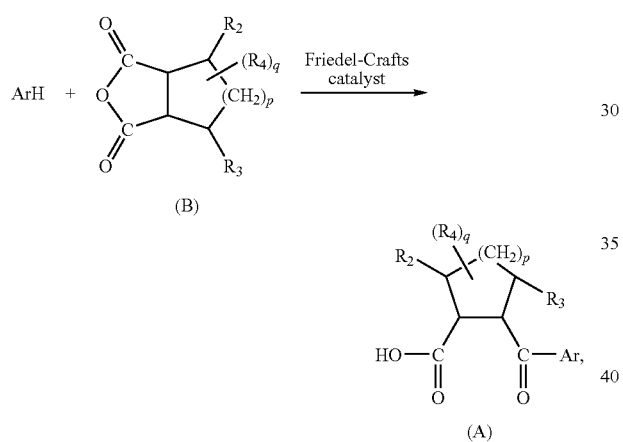

wherein Ar, $R_2$, $R_3$, $R_4$, p and q have the meanings as given above.

1.2:

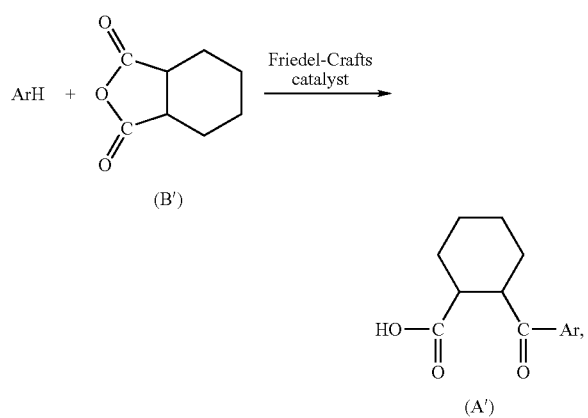

wherein Ar has the meaning as given above.

The person skilled in the art is aware of how to achieve compounds of the formula (B) or (B'), several are commercially available. Examples of preparation methods are given below:

(B) or (B') are for example obtained by hydrogenation of a corresponding aromatic compound (H), (H')

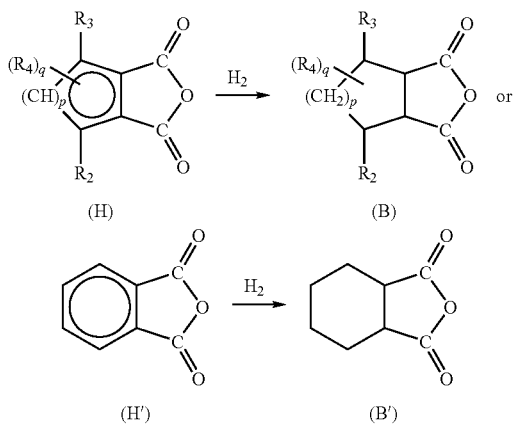

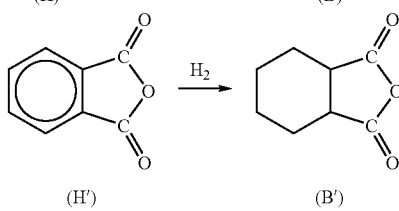

(B) and (B') may for example also be prepared by a Diels-Alder reaction of maleic acid anhydride with a suitable conjugated diene compound and subsequent hydrogenation:

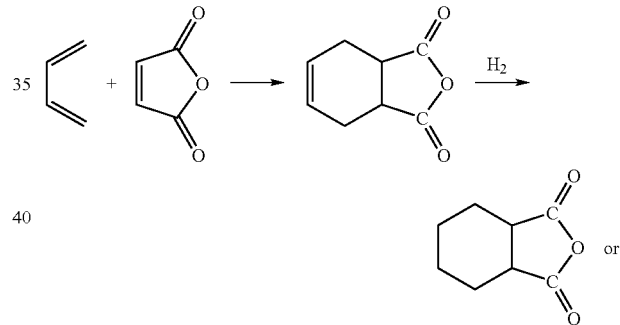

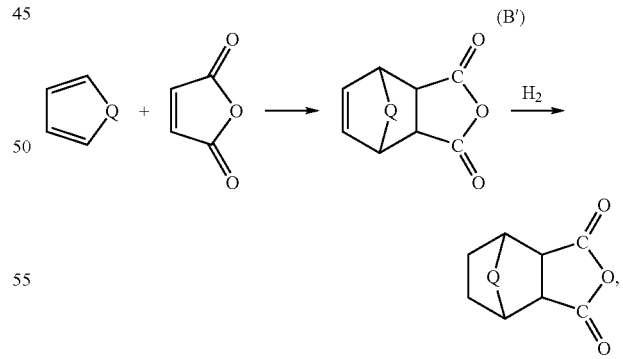

wherein Q denotes O, $C_1$-$C_3$alkylene or CH=CH in compounds of the formula I wherein $R_2$ and $R_3$ are defined together.

Path 2: Via Diels-Alder Reaction

Compounds of the formula (A) or (A') are also obtained via a Diels-Alder reaction performed with cinnamic acid or it's derivatives and a suitable conjugated diene compound, followed by hydrogenation, see examples given below:

2.2.1:

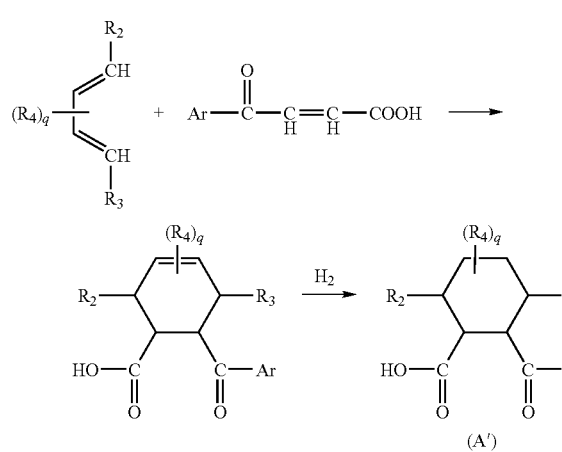

2.2.1:

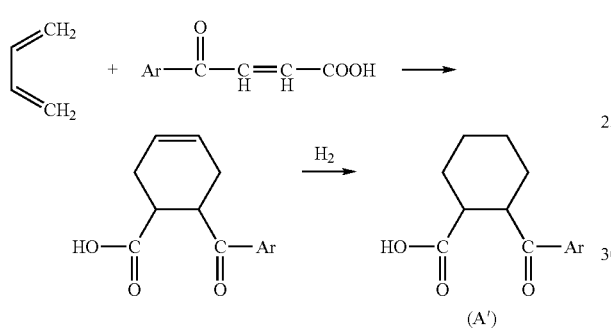

2.3.1:

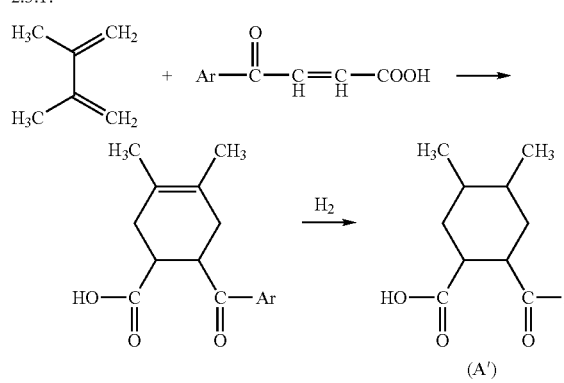

2.4.1:

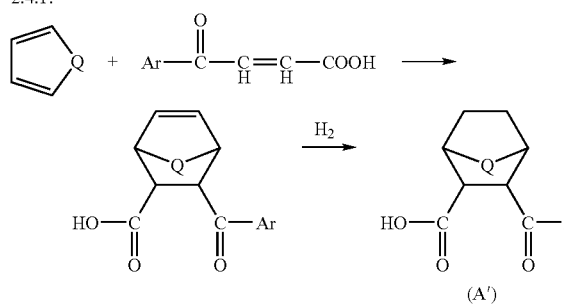

Employing 3-aroyl-acrylic acid esters instead of 3-aroyl-acrylic acid in the above reaction directly opens access to esters of the compound (A) or (A') respectively:

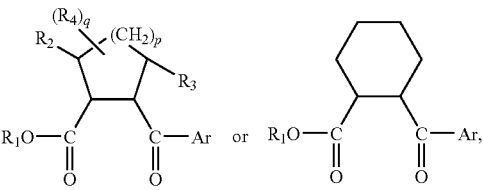

which in both methods, 1 and 2, as described above, the estes.

The Diels Alder reaction for example also can be carried out with maleic acid anhydride and a suitable conjugated diene compound, followed by hydrogenation and subsequent Friedel-Crafts reaction with the aromatic compound Ar—H to give a compound of formula (A) or (A') respectively:

2.1.2:

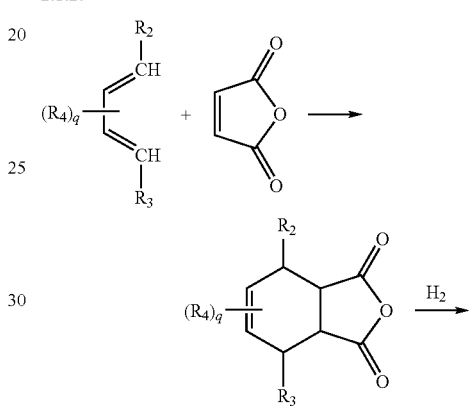

(A') corresponds to (A) and p = 2

2.2.2:

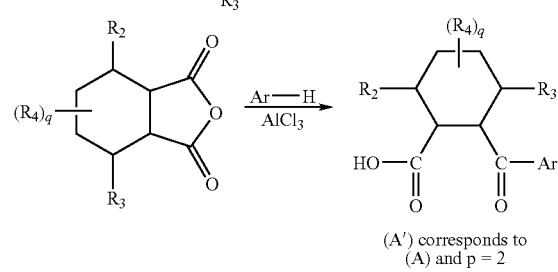

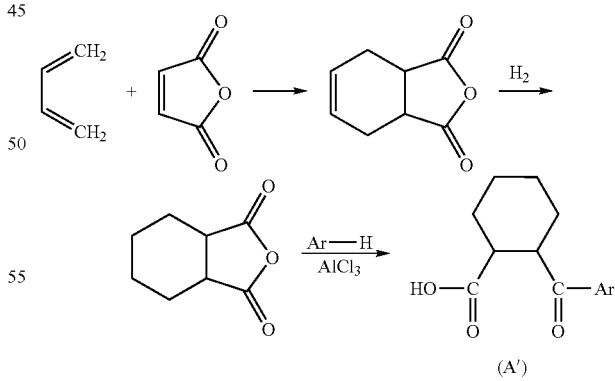

2.3.2:

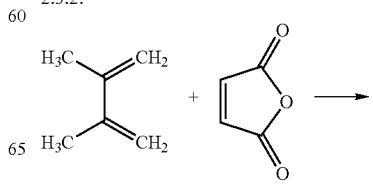

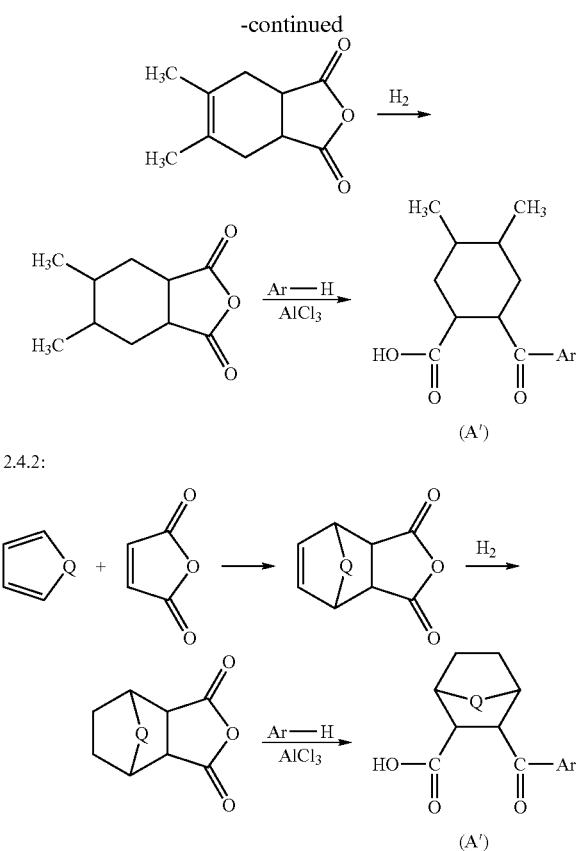

2.4.2:

The halogenation in reaction Step 1. of Method 1 is advantageously carried out by employing halogenating agents as known to the person skilled in the art. Examples are chlorine or bromine, suitable are for example chlorine gas or bromine in acetic acid. Another halogenation agent which may be employed in said reaction is for example sulfurylchloride, for example in a neutral solvent such as e.g. xylene.

That is, the aryl-halogeno-cycloalkyl ketones are for example prepared from the corresponding aryl-cycloalkyl-ketones by the commonly known methods of α-halogenation of ketones. The reaction is for example accelerated by employing an acidic catalyst, such as for example chlorosulphonic acid or toluene sulphonic acid.

Examples of preferred solvents to be used in such halogenation reactions are pure acetic acid, chlorobenzene, o-dichlorobenzene, methylene chloride, tetrachloroethane. The halogenation may for example also be carried out in melt, without a solvent.

The halogenation reaction is for example carried out at ambient temperature or elevated temperature, optionally up to the reflux temperature of the employed solvent.

The conversion of the halogenated intermediate compound (B1), (B2) or (B3) to the hydroxylated intermediate compound (C1) or (C2) in reaction Step 2 of Method 1 is for example achieved by reacting (B1), (B2) and (B3) with an aqueous alkali hydroxide, such as for example sodium hydroxide, or an alkali-alcoholate, such as for example sodium methanolate, solution. The person skilled in the art is familiar with such hydroxylation reactions and is aware of the corresponding reaction conditions and suitable reagents. A small excess of alkali may for example support the end of the hydrolysis. If the hydrolysis is carried out with an alkali alcoholate or the addition of alcohol to sodium hydroxide solution an epoxyether is formed which in an additional step is opened to the α-hydroxy ketone by acidification of the reaction mixture. Preferably said ring opening is initiated by addition of hydrochloric acid or sulphuric acid.

Usually the hydrolysis reaction is for example carried out at ambient temperature or elevated temperature, optionally up to the reflux temperature of the employed solvent.

Preferred suitable solvents for this reaction for example are alcohols, such as methanol or ethanol, water, toluene or mixtures of said solvents. Optionally the solvent(s) employed in the previous halogenation step is also employed for the hydrolysis. In case that the solvent is not an alcohol the hydrolysis for example may be supported by a phase transfer catalyst such as for example quarternary ammonium- or phosphonium salts.

The esterification reaction of the intermediate compounds of the formula (C1) or (C2) in Step 3 of Method 1. and in Step 4 of Method 2. with a mono-, di-, tri- or tetra-alcohol $R_1(H)_x$, wherein $R_1$ and x are as defined above, is performed in a manner known from the textbooks of chemistry, familiar to the person skilled in the art.

Conveniently, the reaction is carried out by mixing the reactants, optionally in a suitable solvent in acidic conditions, i.e. in the presence of an acid, such as for example sulphoric acid, acetic acid etc., or in the presence of a catalyst, such as for example dicyclohexylcarbodiimide.

If, for example mono-alcohols are used, an excess of said alcohols may be employed and the solvent distilled off later on. With suitable alcohols the water is removed by azeotropic distillation by means of an auxiliary solvent according to methods as disclosed in the art. Better results in the esterification reaction are for example obtained by taking a detour via the corresponding acid chloride of (A) or (A') respectively. The acid chloride is for example prepared by a customary reaction with thionyl chloride or another suitable reagent. Then the esterification is carried out with the acid chloride in the presence of a suitable base, such as for example triethylamine or pyridine, and the corresponding alcohol $R_1$—H.

The reaction of an amine $R_1$—H with an acid chloride also is the reaction of choice for the preparation of amides of the formula (I). The hydrochloric acid formed in said reaction is for example neutralized by the addition of a suitable base.

However, the most preferred method for the esterification or preparation of the amides resides in a ring opening reaction of a lactone compound (F) with an alcohol $R_1$—H or an amine $R_1$—H.

In Method 2, Step 1, the brominated lactone (D) or (D') is for example prepared by reacting the corresponding acid with an equimolar amount of bromine at ambient temperature in acetic acid as solvent. The bromination of compounds of the formula (A) for example is performed in acetic acid or acetic acid anhydride as solvent. Suitably the intermediate compound of formula (A) and bromine are each dissolved in acetic acid or acetic acid anhydride, respectively, and the bromine solution is slowly added to the intermediate. Advantageously the reaction mixture is cooled so as to keep the reaction temperature about 20° C. Preferably, acetic acid anhydride is used as the solvent, as the product precipitates from said medium and accordingly can be isolated by filtration, in particular filtration at 0° C. to enhance the yield. To transfer the aceto group in the compounds of formula (D) or (D') into a hydroxy group to give the intermediates (E1) and (E2) or (E1') or (E2') respectively, the compound of formula (D) or (D') in Method 2, Step 2 is for example treated with acid. The compound is for example dissolved in acetic acid and then treated with a stronger acid, such as concentrated hydrochloric acid or sulphuric acid. The hydrolysis of the lactone is advantageously carried out in strongly acidic medium to prevent the hydroylsis of the alkali-labile bromide at this process stage. By heating the suspension to about 35-50° C. the reaction is accelerated and completed. The reaction mixture is poured into water or introduced dropwise into the water, and the product is for example filtrated or extracted with a suitable solvent, such as for example an ether or a chlorinated hydrocarbon. Preferred solvents are ethylacetate, dimethylether, tert.-butyl-methylether, methylene chloride or chloroform. Suitably, the organic phase is washed with water to remove residual acetic acid. After drying and evaporation of the solvent, the product is obtained.

It is, for example, also possible to leave the products (E) in the solvent (not miscible with water) and directly introduce the solved intermediate in the next reaction step. Preferably, ethylacetate, tert.-butyl-methylether or chloroform are used as solvent.

To obtain the intermediate (F) or (F'), respectively, as β-lactone in a good yield, it is essential to create the conditions to have the starting material in the regioselective and stereoselective optimal position for the formation of the 4-membered β-lactone ring. It has now been found, that the bromocarboxylic acids (E1) and (E2) or (E1') and (E2') respectively, meet said conditions. Thus, according to Method 2, Step 3 the intermediates (E1), (E2) or (E1'), (E2'), respectively, are for example treated with a diluted solution of sodium hydrogen carbonate as base. Advantageously the reaction is carried out at temperatures of 0° C. to 20° C., for example 5° C. to 10° C. For example some of the sodium hydrogen carbonate solution (in a concentration of about 0.5% to 2%) is placed in the reaction vessel, while a more concentrated amount of sodium hydrogen carbonate is added dropwise and the intermediate(s) (E), in a solvent which is not miscible with water, is (are) added dropwise, while keeping the pH in a range of about 5 to 7, preferably 6-7. Examples of suitable solvents are ethers, such as for example tert.-butyl-methylether, diethylether, diisopropylether; esters, such as for example acetic acid ethyl ester, acetic acid butyl ester; chlorinated hydrocarbons, such as for example methylene chloride or chloroform; as well as ketones, such as for example methylethyl ketone or methylisobutyl ketone. Preferred are tert.-butyl-methylether, diisopropylether, acetic acid ethyl ester, methylene chloride. The reaction is conducted under stirring and is kept in the abovementioned temperature and pH-range, while controlling the $CO_2$-formation. If the β-lacton during the reaction starts to crystallize uncontrolled, advantageously the amount of organic solvent is increased.

An elaborate review of reactions for the preparation and reactions of β-lactones is for example published by H. Kröper in Houben-Weyl, *Methoden der Organischen Chemie [Methods of Organic Chemistry]*, 4. Ed., Vol. VI/2, pages 511ff (1963). The disclosure of which hereby is incorporated by reference.

According to Method 2, Step 4 the lactone intermediate (F) or (F') is transformed to the corresponding ester or amide of the formula (I) or (I') by methods which are known to the person skilled in the art. For example the methods which are used to transform corresponding acid chlorides to the esters or amides of the formula (I) also can be applied using the lactones of the formula (F) as the starting material.

Thus, treatment of (F) with diluted acid or base results in the formation of intermediates of the formula (C1) and (C2) or (C1') and (C2') respectively, which then can be reacted to give the wanted products as described above.

Or, for example, treatment of the intermediate (F) with an alcohol and a catalytic amount of acid results in the formation of the corresponding ester of the formula (I) or (I') without the formation of side products, which have to be separated from the product. Another possibility to obtain the esters of formula (I) resides in the treatment of (F) with alcohol and a low amount of the corresponding alcoholate.

The corresponding amides are for example, obtained by reacting the intermediate (F) with the corresponding amine.

Such reactions are known in the art and are for example described in textbooks of chemistry or the Houben-Weyl reference cited above.

The Friedel Crafts reaction (see preparation of intermediate, Path A) suitably is carried out in the presence of a Friedel-Crafts catalyst. Such catalysts are known to the person skilled in the art and are published in textbooks of chemistry. The catalysts suitable for Friedel-Crafts reactions for example are described in George A. Olah, *Friedel-Crafts and Related Reactions*, Vol. I, 201 and 284-90 (1963). Aluminium trihalides such as $AlBr_3$ and $AlCl_3$ are particularly suitable.

Other examples are $SnCl_4$; rare earth metal trifluormethanesulfonates (published in *Bulletin of the Chemical Society of Japan*, 2000, 73(10), 2325); copper trifluormethanesulfonates (known from *Tetrahedron*, 2001, 57, 241); uranyl salts (disclosed in *Journal of Molecular Catalysis A: Chemical*, 2000, 164(1-2), 195). The use of HF is described in *Journal of Organic Chemistry*, 1991, 56(20), 5955, while in *Journal of Organic Chemistry*, 1996, 61(26), 9546 alumina/trifluoroacetic anhydride is employed under microwave conditions. $ZnCl_2$ as catalyst is known from *Indian Journal of Heterocyclic Chemistry*, 2002, 11, 229.

Zeolite catalysts in Friedel Crafts reactions are for example disclosed *J. Molecular Catalysis: Chemical* 1998, 134, 121, *Applied Catalysis A: General*, 2000, 201, 159, while the use of clays or exchanged clays is known from U.S. Pat. No. 4,304,941. Suitable clay catalysts are further, for example such distributed as FULCAT™ by Rockwood Additives Ltd.

The application of heteropoly acids or heteropoly acid-containing solid supports as Friedel-crafts catalysts is for example described in *Journal of Molecular Catalysis A: Chemical* 2004, 209(1-2), 189.

The reaction conveniently is carried out in an inert solvent. However it is also possible, for example, to use the aromatic hydrocarbon ArH itself, when liquid, as solvent, in which case it is used in excess. It will be readily understood that the process can also be carried out in inert solvents. Suitable solvents are, for example, the solvents described in George A. Olah, *Friedel-Crafts and Related Reactions*, Vol. I, 298-302 (1963). The choice of the respective solvent depends on the solubility of the educts and catalysts. Typical examples of solvents which may be used in the process are halogenated hydrocarbons such as chlorobenzene, dichlorobenzene, carbon tetrachloride, dichloromethane, tetrachloro-ethylene, bromobenzene, aromatic hydrocarbon derivatives such as nitrobenzene, dinitrobenzene, benzene and toluene, saturated aliphatic hydrocarbons such as pentane, hexane, heptane and the mixtures of isomers thereof, petroleum ether or cyclohexane, or further solvents, typically carbon disulfide, nitroalkanes such as nitromethane, diethyl ether, dimethyl sulfoxide or tetramethylene sulfone.

Chlorobenzene, dichloromethane, benzene, toluene and heptane are preferred solvents.

The reaction is generally carried out by mixing the compound of formula (B) with the ArH and reacting said starting materials in a suitable vessel, which is provided with a heating and cooling means. The reaction conveniently is carried out under inert conditions, i.e. the vessel should be equipped with appropriate means to create said atmosphere by for example working in an atmosphere of nitrogen. Other inert gases, as for example argon, could also be employed. The person skilled in the art is familiar with these facts.

Said reaction can be carried out in different manner. Representative, but not exclusive examples are given below.

a) the catalyst is suspended in a minimum amount of either one or both of the starting materials and then the reactants are added subsequently in any order or are added together.

b) the compound of formula (B) is added during the reaction, to the aromatic hydrocarbon ArH and the catalyst which have been previously mixed;

c) the aromatic hydrocarbon ArH is added during the reaction, to the compound of formula (B) and the catalyst which have been previously mixed;

d) the catalyst is added during the reaction, to the aromatic hydrocarbon ArH and the compound of formula (B) which have been previously mixed.

The reaction vessel also may for example consist of a column that is filled with the catalyst and the aromatic hydrocarbon ArH and the compound of formula (B) are pumped (e.g. continouesly) over the catalyst through the column.

A further possibility is to bring the reactants together via a reactive distillation, which is a process in which a catalytic chemical reaction and distillation occur simultaneously in a single apparatus.

The molar ratios of the starting materials are not critical. Either an excess of the compound of formula (B) or an excess of the aromatic hydrocarbon ArH may be used. The mol ratio of the compound of formula (B) to the aromatic hydrocarbon ArH is for example from 1:10, 1:5, 1:2, or 1:1 or vice versa the mol ratio of the aromatic hydrocarbon ArH to the compound of formula B is for example from 1:10, 1:5, 1:2, or 1:1.

The amount of catalyst to used in the Friedel-Crafts reaction depends on the kind of catalyst which is used. The person skilled in the art is familiar with these facts. For example, if $AlCl_3$ or $AlBr_3$ is used as the catalyst said catalyst conveniently is added in equimolar ratios or in slight excess. In the case where clays, for example FULCAT® are employed as catalayst the equimolar ratio may be reduced. Suitable amounts are for example disclosed in the literature given above with respect to the different catalysts.

The reaction temperature is conveniently in the range from about −30° C. to about 200° C., in principle depending on the kind of catalyst which is used for the reaction. In the case of $AlCl_3$ for example from about −5° C. to about 20° C.; for clay, such as FULCAT®, for example from about 80° C. to about 150° C.

The compounds of the formula (A) and (A') are prepared via a Diels-Alder cycloaddition reactions. The person skilled in the art in general is familiar with the conduction of such reactions [see path 2. for the preparation of compounds of formula (A); as well as one method to prepare the compounds of formula (B)], which are thoroughly described in the literature and usual textbooks of chemistry.

As shown above (see path 2), 3-aroyl-acrylic acid and its derivatives are reacted with a suitable conjugated diene compound.

The reaction of 3-benzoyl-acrylic acid with 1,3-butadiene in ethanol under pressure and 100° C. to give 6-benzoyl-cyclohex-3-ene carboxylic acid is for example disclosed by L. F. Fieser and M. Fieser in *JACS* 57, 1679 (1935), while H. L. Holmes et al in *JACS* 70, 141 (1948) describe the reaction of 3-benzoyl-acrylic acid and 2,3-dimethyl-1,3-butadiene in toluene at 125° C. to give 6-benzoyl-3,4-dimethyl-cyclohex-3-ene carboxylic acid. According to the disclosure of M. Mamaghani, *Tetrahedron* 58, 1, 147-152 (2002), reaction of 3-benzoyl-acrylic acid methylate and cyclopentadiene in benzene at ambient temperature results in the formation of 3-benzoyl-bicyclo[2.2.1]hept-5-ene-2-carboxylic acid methyl ester. For example the following solvents are employed in Diels Alder reactions: aromatic hydrocarbons, such as benzene, toluene, xylene, ethers such as dioxane, diethylether, tetrahydrofurane, alcohols such as for example ethanol or other solvents as for example dichloromethane or acetonitril. The temperatures to conduct the reaction usually are in the range from ambient temperature up to about 200° C., while, when high temperature are afforded, in many cases also conducting the reaction under pressure is necessary to prevent the low volatile components from evaporating. Addition of a small amount of for example hydroquinone or a mercaptane in case that dienes which are sensitive to radical polymerization are employed, will suppress said unwanted radical polymerization. In some cases addition of a small amount of a catalyst is advantageous. For example catalysts of the Lewis acid type are suitable, such as $AlCl_3$ or trifluoromethane sulfonic acid. By employing heterogenous catalysts auxiliary substances may enlarge the reaction surface and thereby cause a cost reduction in the preparation process.

As shown above in 2.1.2 to 2.4.2 maleic acid anhydride is reacted with a suitable conjugated diene compound to give the wanted Diels-Alder reaction product. For example maleic acid anhydride reacted with butadiene in benzene or dioxane at ambient temperature is quantatively transferred to cis-1,2, 3,6-tetrahydrophthalic acid anhydride (K. Alder et al, *Liebigs Annalen der Chemie*, 460, 98 (1928) and 514, 1 (1934)). In the reaction of maleic acid anhydride with 2,3-dimethyl-1,3-dibutadiene in nitromethane and addition of 5 mol % of a rhuthenium catalyst on a hydroxyl apatite support, 5,6-dimethyl-3a,4,7,7a-tetrahydro-isobenzofurane-1,3-dione is formed (K. Mori et al. *JACS* 125, 11460 (2003)). 4,10-dioxatricyclo[$5.2.1.0^{2,6}$]dec-8-ene-3,5-dione is formed by reacting maleic acid anhydride with furane in diethylether. First the kinetically faster endo-product is formed which during 8 h at ambient temperature completely rearranges to the thermodynamically stable exo-product (R. B. Woodward and H. Baer, *JACS* 70 1161 (1948)). Maleic acid anhydride and 1,3-cyclohexadiene in benzene with heating at ambient temperature quantitatively react to 4-oxatricyclo[$5.2.2.0^{2,6}$]undec-8-ene-3,5-dione.

General reviews about conducting Diels Alder reactions are for example given by *Organic reactions* 4 1, 60 (1940) and 5, 136 (1949); *Chem Rev.* 61, 537 (1961); A. S. Onishenko, "*Diene Synthesis*", D, Davey Co., New York (1964); R. Huisgen, R. Grashey and J. Sauer, "*The Chemistry of Alkenes*", Ed. S. Patai, Interscience, New York (1964), Chapter 11; A. Wassermann "*Diels-Alder Reactions*", Elsevier, New York (1965); *Angew. Int.* 5, 211 (1966) and 6, 16 (1967); Houben-Weyl, "*Methoden der Organischen Chemie*", Vol. 5/1c, 977, G. Thieme, Stuttgart (1970).

More information about suitable Lewis acids can for example be found in *JACS* 86, 3899 (1964) and 95, 4094 (1973); *Tetrahedron Letters* 5127 (1970); *Can. J. Chem.* 59, 2377 (1972) and *JOC* 45 5012 (1980).

The disclosure of all said documents hereby is incorporated by reference.

Compounds of the formula I, wherein $R_1$ is a salt structure, i.e. $O^-X^+$, 2 $O^-X^{2+}$, 3 $O^-X^{3+}$ or 4 $O^-X^{4+}$, are obtained from the corresponding acid by reacting it with a suitable salt, e.g. NaCl, or an amine or phosphine, e.g. $NR_{23}R_{24}R_{25}$ or $PR_{23}R_{24}R_{25}$, to the salt.

The isolation of the products is performed in a manner known per se, for example by evaporation of the solvent, distillation, crystallisation from a suitable solvent or solvent mixture or by chromatography.

Aromatic hydrocarbon compounds ArH as well as suitable alcohols and amines $R_1(H)_x$ are commercially available or prepared according to methods known from usual textbooks of chemistry and obvious to the person skilled in the art.

Subject of the invention also is a process for the preparation of compounds of the formula I, wherein a compound of the formula (F)

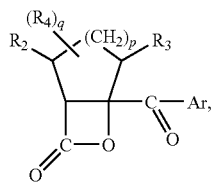
(F)

wherein p, q, $R_2$, $R_3$, $R_4$ and Ar are as defined above,

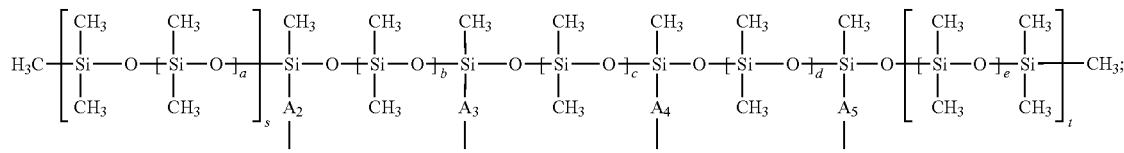

is reacted with $R_1(H)_x$, wherein $R_1$ and x are as defined above.

Interesting further is a process wherein, 1. an aromatic hydrocarbon ArH is reacted with a cyclic hydrocarbon anhydride of formula (B) as described above in the presence of a Friedel-Crafts catalyst, optionally in a solvent, and optionally at elevated temperature and optionally under inert conditions in the molar ratios as described above;

2. treating the product thus obtained with bromine, for example in acetic acid, to give a compound of the formula (D) as described above;

3. subsequently treating the compound of formula (D) with acid to give the compounds of formula (E1) or (E2) or a mixture of compounds of the formula (E1) and (E2) as defined above; and 4. treating the thus obtained compound(s) with a hydrogencarbonate solution to achieve a compound of the formula (F).

In another interesting process after 1., 2., 3. and 4. in the process described above a group $R_1$ is introduced by reacting a compound of the formula (F) with an alcohol or amine $R_1(H)_x$, wherein $R_1$ and x are as defined above, to give a compound of the formula I as described above.

Subject of the invention also are novel intermediate compounds of the formula (F)

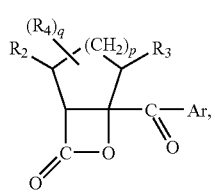
(F)

wherein
p, q, $R_2$, $R_3$, $R_4$ and Ar are as defined above.

Interesting further are compounds of the formula I as described above, wherein x is an integer from 1-4;

p is 2;

q is 0;

Ar is phenyl or phenyl which is substituted by one or more Cl, $OR_5$ or $C_1$-$C_6$alkyl which optionally is substituted by one or more $OR_6$ or $COOR_6$;

$R_1$ if x is 1, is $OR_7$, $O^-X^+$, $NR_8R_9$ or $C_1$-$C_{20}$alkyl;

$R_1$ if x is 2, is O-A-O, $NR'_{15}$-A-$NR_{15}$, $NR_{15a}$-$A_1$-$NR_{15b}$ or $NR'_{15}$—$(CH_2)_{x'}$-A-$(CH_2)_{x'}$—$NR_{15}$;

x' has one of the meanings as given for x;

$R_1$ if x is 3, is $N(R_{30}O)_3$—;

$R_1$ if x is 4, is a tetravalent siloxane of the formula XII $A_2$, $A_3$, $A_4$ and $A_5$ are $C_1$-$C_{10}$alkylene which optionally is substituted by $[O(CH_2)_g$—$O]_h$;

g is 2;

h is 1;

a is 0 b, c, d, e, s and t are 1;

$R_2$ and $R_3$ are hydrogen;

$R_5$ is $C_1$-$C_4$alkyl, $C_1$-$C_4$alkoxy or $(C_2$-$C_4$alkyleneO$)_n$—$R_6$;

$R_6$ is hydrogen, $C_1$-$C_4$alkyl or or $C_2$-$C_4$alkanoyl;

n is an integer from 1-4;

$R_6$ is hydrogen;

$R_7$ is hydrogen, $C_2$-$C_{20}$alkyl which optionally is substituted by OH; or is $C_2$-$C_{20}$alkyl which is interrupted by one ore more O and optionally is substituted by OH; or is $C_1$-$C_{20}$haloalkyl which optionally is substituted by OH;

$R_8$ and $R_9$ independently of one another are hydrogen, $C_1$-$C_{20}$alkyl; $C_1$-$C_8$alkyl substituted by $Si(R_{14})_y(OR_{13})_z$;

or $R_8$ and $R_9$ together are $C_3$-$C_7$alkylene which optionally is substituted by $COOR_{11}$;

z is an integer from 0-3;

y is an integer from 0-3, wherein the sum of y+z is 3;

$R_{11}$ and $R_{13}$ are $C_1$-$C_4$alkyl;

$R_{14}$ is $C_1$-$C_4$alkyl;

$R_{15}$ and $R'_{15}$ are hydrogen or $C_1$-$C_{20}$alkyl;

$R_{15a}$ and $R_{15b}$ independently of one another form an aliphatic ring with a carbon atom of $A_1$ or $R_{15a}$ and $R_{15b}$ together are $C_1$-$C_3$alkylene;

$R_{30}$ is $C_2$-$C_8$-alkylene;

A is $C_2$-$C_{20}$alkylene which optionally is interrupted by one or more O; $C_2$-$C_{20}$haloalkylene; $C_5$-$C_{20}$cycloalkylene; or is a divalent siloxane of the formula X

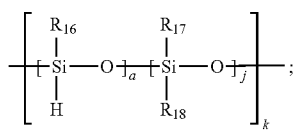

a is 0;
j is 1;
k is 2; and
$R_{16}$ $R_{17}$ and $R_{18}$ are $C_1$-$C_{18}$alkyl;
$A_1$ is $C_2$-$C_{20}$alkylene; and
X is $NR_{22}R_{23}R_{24}R_{25}$;
$R_{22}$, $R_{23}$, $R_{24}$, $R_{25}$ independently of one another are hydrogen; or $C_1$-$C_{20}$alkyl which optionally is substituted by OH, $NR_{26}R_{27}$, benzoyl or $Si(OH)_y(OC_1$-$C_4$alkyl$)_z$;

or two of $R_{22}$, $R_{23}$, $R_{24}$ or $R_{25}$ together form a 6-membered saturated ring which optionally includes O as additional heteroatom; and $R_{26}$ and $R_{27}$ are hydrogen or $C_1$-$C_4$alkyl which optionally is substituted by OH.

Subject of the invention therefore also is the use of the compounds of the formula (F) as intermediates for the preparation of compounds of the formula I.

x and x' are for example an integer from 1-3, in particular an integer 1 or 2, preferably 1.

p preferably is 2.

q is for example an integer from 0-2, in particular from 0 or 1, preferably 0.

Ar is for example phenyl, which is unsubstituted or substituted by one or more halogen, CN, $OR_5$, $C_3$-$C_5$alkenyl or $C_1$-$C_6$alkyl which optionally is substituted by one or more $OR_6$, $COOR_6$ or halogen.

Ar preferably is phenyl, which is unsubstituted or substituted by one or two Cl, $OR_5$, $C_3$-$C_5$alkenyl or $C_1$-$C_4$alkyl which optionally is substituted by one or more $OR_6$, $COOR_6$ or halogen, in particular with $R_5$ denoting $C_1$-$C_4$alkyl or hydrogen and $R_6$ denoting $C_1$-$C_{12}$alkyl, phenyl or $C_2$-$C_{12}$alkyl interrupted by one or more O.

Ar in particular is phenyl which is unsubstituted or is substituted by $C_1$-$C_4$alkyl, by $C_1$-$C_4$alkoxy (which means in the group $OR_5$ $R_5$ is alkyl), or by $C_2$-$C_8$alkyl which is interrupted by one or more, especially two, O.

Especially preferred is Ar as phenyl which is unsubstituted or is substituted by one or two methyl or methoxy.

$R_1$, if x is 1, for example is $OR_7$, $O^-X^+$, $NR_8R_9$, $C_1$-$C_{20}$alkyl optionally substituted by one or more $COOR_{10}$, or is $C_2$-$C_{20}$alkyl interrupted by one ore more O; preferably $OR_7$, $O^-X^+$ or $NR_8R_9$; especially $OR_7$ or $NR_8R_9$.

$R_1$, if x is 2, for example is O-A-O, O-A-$NR_{15}$, $NR_{15}$-A-O, $NR'_{15}$-A-$NR_{15}$, $NR_{15a}$-$A_1$-$NR_{15b}$ or $NR'_{15}$—$(CH_2)_x$-A-$(CH_2)_{x'}$—$NR_{15}$ or is $O^-X^{2+}O^-$, preferably O-A-O, $NR'_{15}$-A-$NR_{15}$, $NR_{15a}$-$A_1$-$NR_{15b}$ or $NR'_{15}$—$(CH_2)_x$-A-$(CH_2)_{x'}$—$NR_{15}$, espcially O-A-O.

$R_2$ and $R_3$ for example independently of one another are hydrogen or $C_1$-$C_4$alkyl, or $R_2$ and $R_3$ together are O, $C_1$-$C_3$alkylene or CH=$CH_2$, in particular hydrogen or $C_1$-$C_4$alkyl, preferably hydrogen.

$R_4$ preferably is hydrogen.

$R_5$ is for example hydrogen, $C_1$-$C_4$alkyl, phenyl which optionally is substituted by one or more $C_1$-$C_4$alkyl, $C_1$-$C_4$alkoxy or halogen; or is $(C_2$-$C_6$alkyleneO$)_n$—$R_6$; in particular is hydrogen, $C_1$-$C_4$alkyl or phenyl, especially hydrogen or $C_1$-$C_4$alkyl, preferably $C_1$-$C_4$alkyl.

$R_6$ is for example hydrogen, $C_1$-$C_4$alkyl, $C_2$-$C_5$alkenyl or $C_2$-$C_6$alkanoyl; in particular hydrogen or $C_1$-$C_4$alkyl, especially hydrogen.

$R_7$ is for example hydrogen, allyl; $C_1$-$C_{12}$alkyl which optionally is substituted by OH; or $C_1$-$C_{12}$alkyl which is interrupted by one or more O and optionally is substituted by OH; preferably hydrogen, $C_1$-$C_{12}$alkyl which optionally is substituted by OH; or $C_1$-$C_{12}$alkyl which is interrupted by one or more O and optionally is substituted by OH.

$R_8$ and $R_9$ independently of each other especially represent hydrogen, $C_1$-$C_8$alkyl, cyclohexyl, allyl, benzyl, phenyl; or $C_2$-$C_8$alkyl which is substituted by one or two $NR_{11}R_{12}$, $OR_{11}$ or $Si(R_{14})_y(OR_{13})_z$, where $R_{11}$ and $R_{12}$ independently of each other in particular denote hydrogen or methyl, or $R_8$ and $R_9$ together are $C_3$-$C_7$alkylene which optionally is interrupted by one ore more O or $NR_{15}$, where $R_{15}$ in particular is hydrogen or $C_1$-$C_4$alkyl.

Preferably $R_8$ and $R_9$ independently of each other especially represent hydrogen, $C_1$-$C_8$alkyl, or $C_2$-$C_8$alkyl which is substituted by one or two $NR_{11}R_{12}$, $OR_{11}$ or $Si(R_{14})_y(OR_{13})_z$, in particular by $Si(R_{14})_y(OR_{13})_z$.

A is for example $C_2$-$C_{20}$alkylene which optionally is interrupted by one or more O or $NR_{15}$, in particular by O; or is $C_2$-$C_{20}$haloalkylene which optionally is interrupted by one or more O or $NR_{15}$, in particular by O; or A is a divalent siloxane. Preferably A is $C_2$-$C_{12}$alkylene which optionally is interrupted by one or more O, $C_2$-$C_{12}$haloalkylene or a divalent siloxane; especially $C_2$-$C_{12}$alkylene.

$A_1$ is for example $C_2$-$C_{20}$alkylene which optionally is interrupted by one or more, e.g. one or two, O or $NR_{15}$; in particular O; preferably $A_1$ is for example $C_2$-$C_{12}$alkylene which optionally is interrupted by one or more, e.g. one or two, O or $NR_{15}$; and in particular is $C_2$-$C_{12}$alkylene.

X for example represents an alkali metal cation, such as $Li^+$, $Na^+$, $K^+$ or $Cs^+$, or is $N^+R_{22}R_{23}R_{24}R_{25}$ or $P^+R_{22}R_{23}R_{24}R_{25}$; e.g. $Li^+$, $Na^+$, $K^+$, $N^+R_{22}R_{23}R_{24}R_{25}$ or $P^+R_{22}R_{23}R_{24}R_{25}$, in particular $Li^+$, $Na^+$, $K^+$ or $N^+R_{22}R_{23}R_{24}R_{25}$.

$R_{22}$, $R_{23}$, $R_{24}$, $R_{25}$ independently of one another for example are are hydrogen; or $C_1$-$C_8$alkyl which optionally is substituted by OH, $NR_{26}R_{27}$, benzoyl or $Si(OH)_y(OC_1$-$C_4$alkyl$)_z$;

or two of $R_{22}$, $R_{23}$, $R_{24}$ or $R_{25}$ together form a 6-membered saturated ring which optionally includes O as additional heteroatom, in particular two of $R_{22}$, $R_{23}$, $R_{24}$ or $R_{25}$ together form a morpholino ring.

In particular preferred are such compounds of the formula I, which are of the formula (I'),

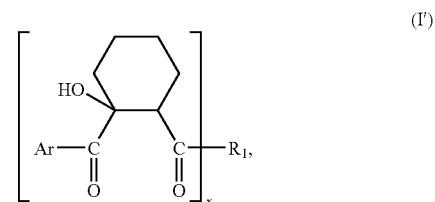

i.e. the compounds of the formula I, wherein q is 0, $R_2$ and $R_3$ are hydrogen, and p is 2. Of these compounds such are especially preferred, wherein x is 1.

Interesting are compounds of the formula I', wherein

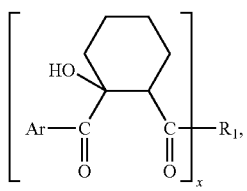

(I')

wherein
Ar is phenyl or naphthyl each of which optionally is substituted by one or more Cl, CN, $OR_5$, $C_3$-$C_5$alkenyl or by $C_1$-$C_6$alkyl which optionally is substituted by one or more $OR_6$, $COOR_6$ or halogen and $R_1$, $R_5$, $R_6$ and x are as defined above.

Preferred are such compounds of the formula I, wherein
x is an integer from 1-4;
p is 2;
q is 0;
Ar is phenyl or phenyl which is substituted by one or more Cl, $OR_5$ or $C_1$-$C_6$alkyl which optionally is substituted by one or more $OR_6$ or $COOR_6$;
$R_1$ if x is 1, is $OR_7$, $O^-X^+$, $NR_8R_9$ or $C_1$-$C_{20}$alkyl;
$R_1$ if x is 2, is O-A-O, $NR'_{15}$-A-$NR_{15}$, $NR_{15a}$-$A_1NR_{15b}$ or $NR'_{15}$—$(CH_2)_{x'}$-A-$(CH_2)_{x'}$—$NR_{15}$;
x' has one of the meanings as given for x;
$R_1$ if x is 3, is $N(R_{30}O)_3$—;
$R_1$ if x is 4, is a tetravalent siloxane of the formula XII A is $C_2$-$C_{20}$alkylene which optionally is interrupted by one or more O; $C_2$-$C_{20}$haloalkylene; $C_5$-$C_{20}$cycloalkylene; or is a divalent siloxane of the formula X

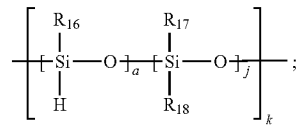

a is 0;
j is 1;
k is 2; and
$R_{16}$ $R_{17}$ and $R_{18}$ are $C_1$-$C_{18}$alkyl;
$A_1$ is $C_2$-$C_{20}$alkylene; and
X is $NR_{22}R_{23}R_{24}R_{25}$;
$R_{22}$, $R_{23}$, $R_{24}$, $R_{25}$ independently of one another are hydrogen; or $C_1$-$C_{20}$alkyl which optionally is substituted by OH, $NR_{26}R_{27}$, benzoyl or $Si(OH)_y(OC_1$-$C_4alkyl)_z$;
or two of $R_{22}$, $R_{23}$, $R_{24}$ or $R_{25}$ together form a 6-membered saturated ring which optionally includes O as additional heteroatom; and
$R_{26}$ and $R_{27}$ are hydrogen or $C_1$-$C_4$alkyl which optionally is substituted by OH.

In particular preferred are the compounds 2-benzoyl-2-hydroxy-cyclohexanecarboxylic acid;
2-hydroxy-2-(4-methyl-benzoyl)-cyclohexanecarboxylic acid;
2-(3,4-dimethyl-benzoyl)-2-hydroxy-cyclohexanecarboxylic acid;

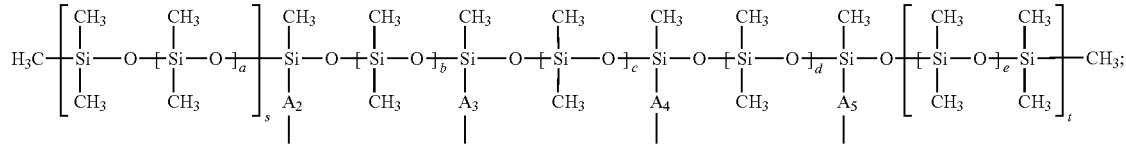

$A_2$, $A_3$, $A_4$ and $A_5$ are $C_1$-$C_{10}$alkylene which optionally is substituted by $[O(CH_2)_g$—$O]_h$;
g is 2;
h is 1;
a is 0
b, c, d, e, s and t are 1;
$R_2$ and $R_3$ are hydrogen;
$R_5$ is $C_1$-$C_4$alkyl;
$R_6$ is hydrogen;
$R_7$ is hydrogen, $C_2$-$C_{20}$alkyl which optionally is substituted by OH; or is $C_2$-$C_{20}$alkyl which is interrupted by one ore more O and optionally is substituted by OH; or is $C_1$-$C_{20}$haloalkyl which optionally is substituted by OH;
$R_8$ and $R_9$ independently of one another are hydrogen, $C_1$-$C_{20}$alkyl; $C_1$-$C_8$alkyl substituted by $Si(R_{14})_y(OR_{13})_z$;
or $R_8$ and $R_9$ together are $C_3$-$C_7$alkylene which optionally is substituted by $COOR_{11}$;
z is an integer from 0-3;
y is an integer from 0-3, wherein the sum of y+z is 3;
$R_{11}$ and $R_{13}$ are $C_1$-$C_4$alkyl;
$R_{14}$ is $C_1$-$C_4$alkyl;
$R_{15}$ and $R'_{15}$ are hydrogen or $C_1$-$C_{20}$alkyl;
$R_{15a}$ and $R_{15b}$ independently of one another form an aliphatic ring with a carbon atom of $A_1$ or $R_{15a}$ and $R_{15b}$ together are $C_1$-$C_3$alkylene;
$R_{30}$ is $C_2$-$C_8$-alkylene;

2-hydroxy-2-(4-methoxy-benzoyl)-cyclohexanecarboxylic acid;
2-(3,4-dimethoxy-benzoyl)-2-hydroxy-cyclohexanecarboxylic acid;
2-benzoyl-2-hydroxy-cyclohexanecarboxylic acid methyl ester;
2-benzoyl-2-hydroxy-cyclohexanecarboxylic acid ethyl ester;
2-benzoyl-2-hydroxy-cyclohexanecarboxylic acid 3-methyl-butyl ester;
2-benzoyl-2-hydroxy-cyclohexanecarboxylic acid 4-hydroxy-butyl ester;
2-hydroxy-2-(4-methyl-benzoyl)-cyclohexanecarboxylic acid ethyl ester;
2-(3,4-dimethyl-benzoyl)-2-hydroxy-cyclohexanecarboxylic acid ethyl ester;
2-hydroxy-2-(4-methoxy-benzoyl)-cyclohexanecarboxylic acid ethyl ester;
2-(3,4-dimethoxy-benzoyl)-2-hydroxy-cyclohexanecarboxylic acid ethyl ester;
2-hydroxy-2-(4-methoxy-benzoyl)-cyclohexanecarboxylic acid 2-hydroxy-ethyl ester;
2-hydroxy-2-(4-methoxybenzoyl)-cyclohexanecarboxylic acid 2-(2-hydroxyethoxy)ethyl ester;
2-(4-chloro-benzoyl)-2-hydroxy-cyclohexanecarboxylic acid ethyl ester;

2-benzoyl-2-hydroxy-cyclohexanecarboxylic acid 6-hydroxy-hexyl ester;
2-(3,4-dimethyl-benzoyl)-2-hydroxy-cyclohexanecarboxylic acid 6-hydroxy-hexyl ester;
2-hydroxy-2-(4-methyl-benzoyl)-cyclohexanecarboxylic acid 6-hydroxy-hexyl ester;
2-hydroxy-2-(4-methoxy-benzoyl)-cyclohexanecarboxylic acid 6-hydroxy-hexyl ester;
2-benzoyl-2-hydroxy-cyclohexanecarboxylic acid 2-(2-hydroxy-ethoxy)-ethyl ester;
2-(3,4-dimethyl-benzoyl)-2-hydroxy-cyclohexanecarboxylic acid 2-(2-hydroxy-ethoxy)-ethyl ester;
2-hydroxy-2-(4-methoxy-3-methyl-benzoyl)-cyclohexanecarboxylic acid 2-(2-hydroxy-ethoxy)-ethyl ester;
2-hydroxy-2-(4-methoxy-benzoyl)-cyclohexanecarboxylic acid 2-(2-hydroxy-ethoxy)-ethyl ester;
2-benzoyl-2-hydroxy-cyclohexanecarboxylic acid 2-[2-(2-hydroxy-ethoxy)-ethoxy]-ethyl ester;
2-(3,4-dimethyl-benzoyl)-2-hydroxy-cyclohexanecarboxylic acid 2-[2-(2-hydroxy-ethoxy)-ethoxy]-ethyl ester;
2-hydroxy-2-(4-methoxy-benzoyl)-cyclohexanecarboxylic acid 2-[2-(2-hydroxy-ethoxy)-ethoxy]-ethyl ester;
2-hydroxy-2-(4-methoxy-benzoyl)-cyclohexanecarboxylic acid 2-hydroxy-propyl ester;
2-benzoyl-2-hydroxy-cyclohexanecarboxylic acid butylamide;
2-benzoyl-2-hydroxy-cyclohexanecarboxylic acid butyl-methyl-amide;
2-(3,4-dimethyl-benzoyl)-2-hydroxy-cyclohexanecarboxylic acid butyl-methyl-amide;
2-hydroxy-2-(4-methoxy-benzoyl)-cyclohexanecarboxylic acid butylamide;
2-hydroxy-2-(4-methoxy-benzoyl)-cyclohexanecarboxylic acid butyl-methyl-amide;
2-hydroxy-2-(4-methoxy-benzoyl)-cyclohexanecarboxylic acid (3-dimethylamino-propyl)-amide;
2-benzoyl-2-hydroxy-cyclohexanecarboxylic acid methyl-(2-methylamino-ethyl)-amide;
2-hydroxy-2-(4-methoxy-benzoyl)-cyclohexanecarboxylic acid methyl-(2-methylamino-ethyl)-amide;
2-hydroxy-2-(4-methoxy-benzoyl)-cyclohexanecarboxylic acid {2-[2-(2-amino-ethoxy)-ethoxy]-ethyl}-amide;
[1-hydroxy-2-(piperazine-1-carbonyl)-cyclohexyl]-(4-methoxy-phenyl)-methanone;
2-hydroxy-2-(4-methoxy-benzoyl)-cyclohexanecarboxylic acid {3-[3-(3-amino-propyl)-1,1,3,3-tetramethyl-disiloxanyl]-propyl}-amide;
and
2-Hydroxy-2-(4-methoxy-benzoyl)-cyclohexanecarboxylic acid 2-methyl-propyl-amide.

The compounds of the formula I are photoinitiators for the photopolymerization of radically poymerizable components Subject of the invention therefore also is a photopolymerizable composition, comprising
(a) at least one ethylenically unsaturated compound; and
(b) at least one photoinitiator compound of the formula I according to claim 1.

The unsaturated compounds (a) may include one or more olefinic double bonds. They may be of low (monomeric) or high (oligomeric) molecular mass. Examples of monomers containing a double bond are alkyl, hydroxyalkyl or amino acrylates, or alkyl, hydroxyalkyl or amino methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride. Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, polyesters containing acrylate-, vinyl ether- or epoxy-groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the abovementioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl) amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol di methacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-R-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl(meth) acrylates.

Other suitable polymers with acrylate or methacrylate groups in the side chains are, for example, solvent soluble or alkaline soluble polyimide precursors, for example poly (amic acid ester) compounds, having the photopolymerizable side groups either attached to the backbone or to the ester groups in the molecule, i.e. according to EP 624826. Such oligomers or polymers can be formulated with the new photoinitiator and optionally reactive diluents, like polyfunctional (meth)acrylates in order to prepare highly sensitive polyimide precursor resists.

Examples of the component (a) are also polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid, for example, photosensitive compounds as described in JP 10-301276 and commercial products such as for example EB9696, UCB Chemicals; KAYARAD TCR1025, Nippon Kayaku Co., LTD., NK OLIGO EA-6340, EA-7440 from Shin-Nakamura Chemical Co., Ltd., or an addition product formed between a carboxyl group-containing resin and an unsaturated compound having an α,β-unsaturated double bond and an epoxy group (for example, ACA200M, Daicel Industries, Ltd.). Additional commercial products as examples of component (a) are ACA200, ACA210P, ACA230AA, ACA250, ACA300, ACA320 from Daicel Chemical Industries, Ltd.).

The photopolymerizable compounds are used alone or in any desired mixtures. It is preferred to use mixtures of polyol (meth)acrylates.

A preferred composition comprises at least one compound having at least one free carboxylic group, said compound being either subject of component (a) or of a binder polymer.

As diluent, a mono- or multi-functional ethylenically unsaturated compound, or mixtures of several of said compounds, can be included in the above composition up to 70% by weight based on the solid portion of the composition.

The unsaturated compounds (a) can also be used in admixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are cross-linked by means of thermal after treatment.

The invention also provides compositions comprising as component (a) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 mol to 1.0 mol of polymerizable double bonds per 100 g of prepolymer and an average molecular weight of, for example, at least 400, in particular from 500 to 10'000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane(meth) acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl(meth)acrylate polymers, are described for example in EP 41125, and suitable water dispersible, radiation-curable prepolymers of urethane acrylates can for example be found in DE 2936039.

Further, additives may be included in these radiation-curable aqueous prepolymer dispersions, for example dispersion auxiliaries, emulsifiers, antioxidants, e.g. 2,2-thiobis(4-methyl-6-t-butylphenol) or 2,6-di-t-butylphenol, light stabilizers, dyes, pigments (specific examples given below), fillers, such as glass or alumina, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

For curing of such compositions comprising as component (a) at least one ethylenically unsaturated photopolymerizable compound which is emulsified or dissolved in water in particular compounds of the formula I with "salt groups", that is compounds wherein $R_1$ is $O^-X^+$, $O^-X^{2+}O^-$, 3 $O^-X^{3+}$ or 4 $O^-X^{4+}$.

The composition according to the invention may comprise additionally to the photoinitiator (b) at least one further photoinitiator (c), and/or other additives (d).

In certain cases it may be of advantage to use mixtures of two or more of the novel photoinitiators. It is of course also possible to use mixtures with known photoinitiators (c), for example mixtures with camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxybenzophenone, [4-(4-methylphenylthio)phenyl]-phenyl-methanone, methyl-2-benzoylbenzoate, 3-methyl-4'-phenylbenzophenone, 2,4,6-trimethyl-4'-phenylbenzophenone, 4,4'-bis(dimethylamino)-benzophenone, 4,4'-bis(diethylamino)benzophenone; ketal compounds, as for example benzildimethylketal (IRGACURE® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (DAROCUR® 1173), 1-hydroxy-cyclohexyl-phenyl-ketone (IRGACURE® 184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (IRGACURE®2959); 2-hydroxy-1-{4-[4-(2-hydroxy-2-methyl-propionyl)-benzyl]-phenyl}-2-methyl-propan-1-one (IRGACURE®127); 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholino-ethane (IRGACURE® 907), (4-morpholinobenzoyl)-1-benzyl-1-dimethyl-aminopropane (IRGACURE® 369), (4-morpholinobenzoyl)-1-(4-methylbenzyl)-1-dimethyl-aminopropane (IRGACURE® 379), (4-(2-hydroxyethyl) aminobenzoyl)-1-benzyl-1-dimethyl-aminopropane), 2-benzyl-2-dimethylamino-1-(3,4-dimethoxyphenyl)butanone-1; 4-aroyl-1,3-dioxolanes, benzoin alkyl ethers and benzil ketals, e.g. dimethyl benzil ketal, phenylglyoxalic esters and derivatives thereof, e.g. oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (IRGACURE® 754); oximeesters, e.g. 1,2-octanedione 1-[4-(phenylthio)phenyl]-2-(O-benzoyloxime) (IRGACURE® OXE01), ethanone 1-[9-ethyl-6-(2-methylbenzoyl)-9H-carbazol-3-yl]-1-(O-acetyloxime) (IRGACURE® OXE02), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethylbenzoyl)diphenylphosphine oxide (DAROCUR® TPO), ethyl (2,4,6 trimethylbenzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide (IRGACURE® 819), bis(2,4,6-trimethylbenzoyl)-2,4-dipentoxy-phenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl)-titanium (IRGACURE®784). Further, borate compounds can be used as coinitiators.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17-25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example (η⁶-iso-propylbenzene)(η⁵-cyclopentadienyl)piron(II) hexafluorophosphate or oxime sulfonates.

The DAROCUR® and IRGACURE® compounds are available from Ciba Specialty Chemicals.

The new photoinitiators, either alone or in mixtures with other known photoinitiators and sensitizers, can be used also in the form of a dispersion or emulsion in water or aqueous solutions.

The photopolymerizable compositions generally comprise 0.05 to 20% by weight, preferably 0.01 to 10% by weight, in particular 0.01 to 5% by weight of the photoinitiator, based on the solid composition. The amount refers to the sum of all photoinitiators added, if mixtures of initiators are employed. Accordingly, the amount either refers to the photoinitiator (b) or the photoinitiators (b)+(c).

In addition to the photoinitiator the photopolymerizable mixtures may include various additives (d). Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine.

Pot life of in particular 2- and multicomponent polyurethane-forming compositions is for example increased by addition of about 0.05-3% of acids with pK 2.8-4.5 (e. g. salicylic or phthalic acid or sodium aluminosilicate, silicic acid). Further suitable for obtaining prolonged potlife is for example the addition of highly disperse silica.

To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer on top of the coating, for example poly(vinylalcohol-co-vinylacetate). Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilisers are disclosed in WO 04/074328, page 12, line 9 to page 14, line 23, said disclosure hereby is incorporated by reference To accelerate the photopolymerization it is possible to add amines as component (d), for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention as component (d). Examples are mercaptans, amines and benzothiazol.

Photopolymerization can also be accelerated by adding further photosensitizers or coinitiators (as component (d)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

As photosensitizers, it is also possible, for example, to consider the amines given above. Examples of suitable sensitizer compounds (d) are disclosed in WO 06/008251, page 36, line 30 to page 38, line 8, the disclosure of which is hereby incorporated by reference.

The curing process can be assisted by adding a component which under thermal conditions forms free radicals, for example an azo compound such as 2,2'-azobis(4-methoxy-2, 4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (d) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP 445624.

Another example for a further additive (d) is a color forming agent that generates color under UV exposure. Example of color forming agents are leuco dyes, like triphenylmethan leuco dye, phthalide derivatives and fluoran derivatives. Specific examples are leuco crystal violet, leuco malachite green, 4,4'-[(9-Butyl-9H-carbazol-3-yl)methylene]bis[N-methyl-N-phenylaniline] and crystal violet lactone.

Further additives known in the art may be added as component (d), as for example flow improvers, adhesion promoters, such as vinyltrimethoxysilane, vinyltriethoxysilane vinyltris(2-methoxyethoxy)silane, N-(2-aminoethyl)-3-aminopropylmethyldimethoxysilane, N-(2-amino-ethyl)3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane and 3-mercaptopropyltrimethoxysilane. Surfactants, optical brighteners, pigments, dyes, wetting agents, levelling assistants, dispersants, aggregation preventers, antioxidants or fillers are further examples for additives (d).

In order to cure thick and pigmented coatings it is appropriate to add glass microspheres or pulverized glass fibres, as described for example in U.S. Pat. No. 5,013,768.

The choice of additive(s) (d) is made depending on the field of application and on properties required for this field. The additives described above are customary in the art and accordingly are added in amounts which are usual in the respective application.

Binders (e) as well can be added to the novel compositions. This is particularly expedient when the photopolymerizable compounds are liquid or viscous substances. The quantity of binder may, for example, be 2-98%, preferably 5-95% and especially 20-90%, by weight relative to the overall solids content. The choice of binder is made depending on the field of application and on properties required for this field, such as the capacity for development in aqueous and organic solvent systems, adhesion to substrates and sensitivity to oxygen. Examples of suitable binders are polymers having a molecular weight of about 2'000 to 2'000'000, preferably 5'000 to 1'000'000. Examples of alkali developable binders are acrylic polymer having carboxylic acid function as a pendant group, such as conventionally known copolymers obtained by copolymerizing an ethylenic unsaturated carboxylic acid such as (meth)acrylic acid, 2-carboxyethyl(meth)acrylic acid, 2-carboxypropyl(meth)acrylic acid itaconic acid, crotonic acid, maleic acid, fumaric acid and ω-carboxypolycaprolactone mono(meth)acrylate, with one or more monomers selected from esters of (meth)acrylic acid, such as methyl(meth)acrylate, ethyl(meth)acrylate, propyl(meth)acrylate, butyl(meth)acrylate, benzyl(meth)acrylate, 2-ethylhexyl(meth)acrylate, hydroxyethyl(meth)acrylate, hydroxypropyl(meth)acrylate, glycerol mono(meth)acrylate, tricyclo[5.2.1.0$^{2,6}$]decan-8-yl (meth)acrylate, glycidyl(meth)acrylate, 2-methylglycidyl (meth)acrylate, 3,4-epoxybutyl(meth)acrylate, 6,7-epoxyheptyl(meth)acrylate, N,N-dimethylaminoethyl(meth)acrylate, N,N-diethylaminoethyl(meth)acrylate, N,N-diethylaminoethyl(meth)acrylate, N,N-dimethylaminopropyl(meth)acrylate; vinyl aromatic compounds, such as styrene, α-methylstyrene, vinyltoluene, p-chlorostyrene, vinylbenzyl glycidyl ether, 4-vinylpyridine; amide type unsaturated compounds, (meth)acrylamide diacetone acrylamide, N-methylolacrylamide, N-butoxymethacrylamide N,N-dimethylacrylamide, N,N-dimethylaminopropyl(meth)acrylamide; and polyolefin type compounds, such as butadiene, isoprene, chloroprene and the like; methacrylonitrile, methyl isopropenyl ketone, mono-2-[(meth)acryloyloxy]ethyl succinate, N-phenylmaleimide, maleic anhydride, vinyl acetate, vinyl propionate, vinyl pivalate, vinylpyrrolidone, N,N-dimethylaminoethyl vinyl ether, diallylamine, polystyrene macromonomer, or polymethyl(meth)acrylate macromonomer. Examples of copolymers are copolymers of acrylates and methacrylates with acrylic acid or methacrylic acid and with styrene or substituted styrene, phenolic resins, for example novolak, (poly) hydroxystyrene, and copolymers of hydroxystyrene with alkyl acrylates, acrylic acid and/or methacrylic acid. Preferable examples of copolymers are copolymers of methyl methacrylate/methacrylic acid, copolymers of benzyl methacrylate/methacrylic acid, copolymers of methyl methacrylate/ ethyl acrylate/methacrylic acid, copolymers of benzyl methacrylate/methacrylic acid/styrene, copolymers of benzyl methacrylate/methacrylic acid/hydroxyethyl methacrylate, copolymers of methyl methacrylate/butyl methacrylate/ methacrylic acid/styrene, copolymers of methyl methacrylate/benzyl methacrylate/methacrylic acid/hydroxyphenyl methacrylate. Examples of solvent developable binder polymers are poly(alkyl methacrylates), poly(alkyl acrylates), poly(benzylmethacrylate-co-hydroxyethylmethacrylate-co-methacrylic acid), poly(benzylmethacrylate-co-methacrylic acid); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), and polyesters such as poly(ethylene glycol terephtalate) and poly(hexamethylene glycol succinate) and polyimide binder resins.

The polyimide binder resin can either be a solvent soluble polyimide or a polyimide precursor, for example, a poly(amic acid).

Interesting is a photopolymerizable composition, comprising as binder polymer (e), a copolymer of methacrylate and methacrylic acid. Interesting further are polymeric binder components as described e.g. in JP 10-171119-A.

The novel photoinitiators of the present invention may also be employed in "dual curable" or "double curable" compositions.

Accordingly, the invention further relates to a dual curable coating composition, comprising
(a) at least one ethylenically unsaturated compound;
(f) a thermal crosslinkable compound; and
(b) at least one compound of the formula I, as described above, as photoinitiator.

The invention also relates to a double (thermal and UV) curable coating composition, comprising
(a) at least an ethylenically unsaturated compound;
(b) at least one compound of the formula I as described above as UV-photoinitiator effective to enable UV-curing of the ethylenically unsaturated compound; and
(g) at least one thermal radical initiator effective to enable IR-curing or NIR-curing or to enable the convection heat curing of the ethylenically unsaturated compound.

"Thermal curing" refers to the application of convection heat or IR- or NIR-radiation after the composition has been applied to the substrate. In case of powder coatings the adhered powder coating is first melted to form a surface layer preferably by convection heat. Suitable temperatures to initiate and complete free-radical polymerization are 60-180° C.

"Double curable compositions" comprise ethylenically unsaturated monomers, which can be polymerized by UV radiation or which can be polymerized thermally induced by IR or NIR radiation or by convection heat. In a double cure system the thermal curing is preferably followed by UV-curing. However, it is also possible that the UV-curing follows the thermal curing.

"Dual curable compositions" comprise ethylenically unsaturated monomers, which can be polymerized thermally induced by IR or NIR radiation or by convection heat. Furthermore, at least one second thermal crosslinkable compound is present. The second compound preferably crosslinks via a polyol-isocyanate reaction to form a polyurethane.

Examples for ethylenically unsaturated compounds (a) are given above.

In dual curing compositions at least one second thermal crosslinkable compound (f) is present. Examples of said compounds are:

1. surface coatings based on cold- or hot-crosslinkable alkyd, acrylate, polyester, epoxy or melamine resins or mixtures of such resins, optionally with the addition of a curing catalyst;

2. two-component polyurethane surface coatings based on hydroxyl-group-containing acrylate, polyester or polyether resins and aliphatic or aromatic isocyanates, isocyanurates or polyisocyanates;

3. two-component polyurethane surface coatings based on thiol-group-containing acrylate, polyester or polyether resins and aliphatic or aromatic isocyanates, isocyanurates or polyisocyanates;

4. one-component polyurethane surface coatings based on blocked isocyanates, isocyanurates or polyisocyanates which are deblocked during stoving; the addition of melamine resins is also possible, if desired;

5. one-component polyurethane surface coatings based on aliphatic or aromatic urethanes or polyurethanes and hydroxyl-group-containing acrylate, polyester or polyether resins;

6. one-component polyurethane surface coatings based on aliphatic or aromatic urethane acrylates or polyurethane acrylates having free amine groups in the urethane structure and melamine resins or polyether resins, optionally with the addition of a curing catalyst;

7. two-component surface coatings based on (poly) ketimines and aliphatic or aromatic isocyanates, isocyanurates or polyisocyanates;

8. two-component surface coatings based on (poly)ketimines and an unsaturated acrylate resin or a polyacetoacetate resin or a methacrylamidoglycolate methyl ester;

9. two-component surface coatings based on carboxyl- or amino-group-containing polyacrylates and polyepoxides;

10. two-component surface coatings based on anhydride-group-containing acrylate resins and a polyhydroxy or polyamino component;

11. two-component surface coatings based on acrylate-containing anhydrides and polyepoxides;

12. two-component surface coatings based on (poly)oxazolines and anhydride-group-containing acrylate resins or unsaturated acrylate resins or aliphatic or aromatic isocyanates, isocyanurates or polyisocyanates;

13. two-component surface coatings based on unsaturated (poly)acrylates and (poly)malonates;

14. thermoplastic polyacrylate surface coatings based on thermoplastic acrylate resins or extrinsically crosslinking acrylate resins in combination with etherified melamine resins;

15. surface-coating systems, especially clearcoats, based on malonate-blocked isocyanates with melamine resins (e.g. hexamethoxymethylmelamine) as crosslinkers (acid-catalysed);

16. UV-curable systems based on oligomeric urethane acrylates and/or acylate acrylates, optionally with the addition of other oligomers or monomers;

17. dual-cure systems, which are cured first thermally and then by UV, or vice versa, the constituents of the surface-coating formulation containing double bonds that can be caused to react by UV light and photoinitiators and/or by electron-beam curing.

The thermal radical initiator (g) effective to enable IR-curing or NIR-curing or to enable the convection heat is for example a compound selected from the group consisting of peroxides, such as for example benzoyl peroxide (other suitable peroxides are described in U.S. Pat. No. 4,950,581 column 19, lines 17-25); azobisisobutyronitrile (AIBN), benzpinacol or an N-substituted imide as for example described in WO06/051047, the disclosure of which hereby is incorporated by reference.

Photoinitiators and photopolymerizable compositions find a widespread use known to the person skilled in the art. The following description of examples is not meant to be exclusive with respect to the novel photoinitiators and photocurable compositions of the present invention.

The photopolymerizable compositions can be used for various purposes, for example as printing ink, e.g. screen printing inks, inks for offset- or flexo printing, as a clear finish, as a white or colored finish, for example for wood or metal, as powder coating, as a coating material for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image, the coating of metals, in the case, for example, of the coating of metal plates and tubes, cans or bottle caps, and the photocuring of polymer coatings, for example of floor or wall coverings based on PVC, the photocuring of paper coatings e.g. the colourless varnishing of labels, record sleeves and book covers, as a daylight-curable coating for the marking of buildings and roadmarking, for photographic reproduction techniques, for recording materials, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as resists, as etch resists, solder resists, electroplating resists, or permanent resists, both liquid and dry films, as photostructurable dielectric, for printed circuit boards and electronic circuits, for TFT applications, as resists to manufacture color filters for a variety of display applications or to generate structures in the manufacturing process of plasma-display panels and electroluminescence displays, (as for example described in U.S. Pat. No. 5,853,446, EP 863534, JP 09-244230-A, JP 10-62980-A, JP 08-171863-A, U.S. Pat. No. 5,840,465, EP 855731, JP 05-271576-A, JP 05-67405-A) for the production of optical switches wherein advantage is taken of the development of a difference in the index of refraction between irradiated and unirradiated areas, for the production of holographies, waveguides, optical lattices (interference lattice), light circuits, for protective layers, dielectric layers, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and integrated circuits, or as coatings for optical fibres, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE 19700064 and EP 678534. The compositions comprising the novel photoinitiator can, for example, also be used as repair materials and as putty materials.

The novel photoinitiator may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

The novel photoinitiator can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a free-radical photoinitiator, such formulations being as described, for example, in the paper "Radiation Curing of Powder Coating", Conference Proceedings, Radtech Europe 1993 by M. Wittig and Th. Gohmann. Free-radically UV-curable powder coatings can also be formulated by mixing unsaturated polyester resins with solid acrylates, methacrylates or vinyl ethers and with the novel photoinitiator. The powder coatings in general can also contain binders, as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator, the powder coating formulations may also include UV absorbers. Appropriate examples are listed in WO 04/074328, page 12, line 9 to page 14, line 23, said disclosure hereby is incorporated by reference.

The use of photocurable compositions for imaging techniques and for the optical production of information carriers is also important. In such applications the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists. When used in image-forming materials the novel photoinitiators provide excellent performance in generating so called printout images, whereby a color change is induced due to irradiation. To form such printout images different dyes and/or their leuco form are used and examples for such print out image systems can be fount e.g. in WO 96/41240, EP 706091, EP 511403, U.S. Pat. No. 3,579,339, and U.S. Pat. No. 4,622,286.

The novel radiation-sensitive compositions find application as negative resists, having a very high sensitivity to light and being able to be developed in an aqueous alkaline medium without swelling. They are suitable for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

The novel composition also relates to a photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of imagewise exposing a layer of the resin composition selectively to an actinic ray through a photomask having a pattern and developing the unexposed part of the layer.

In addition to a process in which the light-sensitive resin composition is coated on a substrate and dried, the light-sensitive resin composition of the present invention can be used as well for a layer transfer material.

The term "imagewise" exposure includes both, exposure through a photomask comprising a predetermined pattern, for example a slide, a chromium mask, a stencil mask or a reticle, as well as exposure by means of a laser or light beam, which for example is moved under computer control over the surface of the coated substrate and in this way produces an image. Suitable UV laser exposure systems for the purpose are, for example, provided by Etec and Orbotech (DP-100™ DIRECT IMAGING SYSTEM). And the computer-controlled irradiation can also be achieved by electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.- P. Nicolay in Offset Printing 1997, 6, p. 34-37.

Following the imagewise exposure of the material and prior to development, it may be advantageous to carry out thermal treatment for a short time. After the development a thermal post bake can be performed to harden the composition and to remove all traces of solvents. The temperatures employed are generally 50-250° C., preferably 80-220° C.; the duration of the thermal treatment is in general between 0.25 and 60 minutes.

A diluted aqueous solution of an alkaline substance can be used as a developing solution for the light-sensitive resin composition of the present invention if the composition contains alkali soluble resin or alkali soluble monomers or oligomers, and further a developer solution prepared by adding a small amount of a water-miscible organic solvent thereto is included as well. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents. Depending on the substrate also solvents, e.g. organic solvents, can be used as developer, or, as mentioned above mixtures of aqueous alkalis with such solvents. Particularly useful solvents for solvent development include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butylolactone, dimethylformamide, dimethylacetamide, hexamethylphosphoramide, ethyl lactate, methyl lactate, epsilon-caprolactam, and N-methyl-pyrrolidinone. Optionally, water can be added to these solvents up to a level at which still a clear solution is obtained and at which sufficient solubility of the unexposed areas of the light sensitive composition is maintained. Further, a publicly known surface active agent can be added. The concentration of the surface active agent is preferably 0.001 to 10 weight %.

The light sensitive resin composition of the present invention can also be developed with organic solvents, including blends of two or more solvents, not containing alkaline compounds. The developer solution can be used in all forms known to the person skilled in the art, for example in form of a bath solution, puddle, or a spraying solution.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 5 to about 60 minutes.

The novel photoinitiator is also suitable for a photopatternable composition for forming a dielectric layer of a multilayer layer circuit board produced by a sequential build-up process.

Because the photocurable compositions according to the invention have a good thermal stability and are sufficiently resistant to inhibition by oxygen, they are suitable for the production of color filters or color mosaic systems, such as described, for example, in EP 320 264.

In a color filter resist composition the whole amount of the monomers contained in the photopolymerizable composition is preferably 5 to 80% by weight, in particular 10 to 70% by weight based on the whole solid contents of the composition, i.e. the amount of all components without the solvent(s).

It is obvious to those skilled in the art, that the photosensitive compositions of the present invention can be used for generating red, green and blue color pixels and a black matrix, for the manufacture of a color filter, regardless of differences in processing, regardless, of additional layers which can be applied and regardless of differences in the design of the color filter. The use of a composition according to the present invention to form colored elements shall not be regarded as limited by different designs and manufacturing processes of such color filters.

The photosensitive compositions according to the invention are also suitable for manufacturing interlayer insulating layers or dielectric layers in a liquid crystal display (LCD), and more particularly in a reflection type liquid crystal display including an active matrix type display having a thin film transistor (TFT) as a switching device, and a passive matrix type without a switching device.

The photosensitive compositions according to the invention can further be used for manufacturing spacers, which control a cell gap of the liquid crystal part in liquid crystal display panels.

The photosensitive compositions according to the invention are also suitable for manufacturing microlens arrays used in liquid crystal display panels, image sensors and the like. Microlenses are microscopic passive optical components that fit on active optoelectronic devices such as detectors, displays, and light emitting devices (light-emitting diodes, transversal and vertical cavity lasers) to improve their optical input or output quality. The areas of applications are wide and cover areas such as telecommunications, information technology, audio-visual services, solar cells, detectors, solid-state light sources, and optical interconnects. Because the photocurable compositions according to the invention have low yellowing properties, both thermally and photochemically, they are suitable for the production of microlens arrays as described above.

The novel radiation-sensitive compositions are also suitable for photo-lithographic steps used in the production process of plasma display panels (PDP), the DC (direct current) type and AC (alternating current) type as well, particularly for the imaging forming process of barrier rib, phosphor layer and electrodes.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

Photocuring is of great importance for printings, since the drying time of the ink is a critical factor for the production rate of graphic products, and should be in the order of fractions of seconds. UV-curable inks are particularly important for screen printing and offset inks. The photoinitiators of the present invention are also suitable in said UV-curable printing inks. Such printing inks are known to the person skilled in the art, are used widely in the art and are described in the literature. They are, for example, pigmented printing inks and printing inks coloured with dyes. A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks. Suitable pigments, like the printing ink formulations customary in the art, are generally known and widely described.

The printing inks can be used, for example, for intaglio printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks. Of interest are, for example, printing inks based on aqueous acrylate.

For intaglio or flexographic printing, a printing ink is usually prepared by dilution of a printing ink concentrate and can then be used in accordance with methods known per se. The printing inks may, for example, also comprise alkyd systems that dry oxidatively.

The ink usually comprises a pigment or a dye or a combination of pigments or dyes, a dispersant and a binder. It will be understood that the printing inks may comprise further auxiliaries, such as are customary, for example preservatives, anti-oxidants, degassers/defoamers, viscosity regulators, thickeners, flow improvers, anti-settling agents, gloss improvers, lubricants, adhesion promoters, anti-skin agents, matting agents, emulsifiers, stabilisers, hydrophobic agents, light stabilisers, handle improvers, anti-statics, buffer substances, surfactants, humectants and substances that inhibit the growth of fungi and/or bacteria.

The printing inks may also be prepared in customary manner by mixing the individual components together, for example in the desired amount of water.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

As already mentioned above, the photocurable compositions are highly suitable also for producing printing plates, such as for example relief printing plates, planographic printing plates, intaglio printing plates; also so-called processless plates, which do not need a separate development step upon exposure. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Also of interest is the use of the novel photoinitiators for curing shaped articles made from composite compositions. The composite compound consists of a self-supporting matrix material, for example a glass fibre fabric, or alternatively, for example, plant fibres [cf. K.- P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, surfboards etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc.

The photoinitiator systems according to present invention are also suitable for use in compositions as coatings for optical fibers. In general, optical fibers are coated with protective coats directly after their production. The fiber of glass is drawn and then one or more coatings are applied to the glass string. Usually, one, two or three coats are applied, the top coating, for example, is colored ("ink layer or ink coating"). Further, several thus coated optical fibers may be put together to a bundle and be coated all together, i.e. cabling of the fibers. The compositions according to the present invention in general are suitable for any of these coatings, which have to exhibit good softness over a broad temperature range, good tensile strength and toughness and rapid UV-curing characteristics.

Each of the coats, inner primary (usually a soft coating), outer primary or secondary (usually a harder coating than the inner coating), tertiary or the cabling coat, may comprise at least one radiation-curable oligomer, at least one radiation curable monomer diluent, at least one photoinitiator, and additives.

The preparation of suitable radiation-curable oligomers and the preparation of compositions for optical fiber coatings including appropriate additives, such as for example antioxidants, light stabilizers, UV absorbers, wetting agents, silane coupling agents, optical brighteners, pigments etc. is known to the person skilled in the art and for example published in U.S. Pat. No. 6,136,880, incorporated herein by reference.

In this application it may be of advantage to use the novel photoinitiator compounds in admixture with further photoinitiators, in particular for example with mono- or bisacylphosphine oxide, such as 2,4,6-trimethylbenzoyl-di-phenyl phosphine oxide (DAROCUR®TPO) or bis(2,4,6-trimethylbenzoyl)-phenyl phosphine oxide (IRGACURE®819).

The compositions according to the present invention are also suitable for the production of adhesives, e.g. laminating, structure or pressure sensitive adhesives, such as for example pressure sensitive hot-melt adhesives.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are, for example, silicon wafers. The layer thickness of the photosensitive layer for photographic materials and offset printing forms is generally from about 0.5 µm to 10 µm, while for printed circuits it is from 0.1 µm to about 100 µm. Following the coating of the substrates, the solvent is removed, generally by drying, to leave a coat of the photoresist on the substrate.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate, ethyl 3-ethoxypropionate, 2-methoxypropylacetate, methyl-3-methoxypropionate, 2-heptanone, 2-pentanone, and ethyl lactate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, or a glass substrate by transferring the layer via lamination.

The quantity applied (coat thickness) and the nature of the substrate (layer support) are dependent on the desired field of application. The range of coat thicknesses generally comprises values from about 0.1 µm to more than 100 µm, for example 0.1 µm to 1 cm, preferably 0.5 µm to 1000 µm.

Following the coating of the substrates, the solvent is removed, generally by drying, to leave an essentially dry film on the substrate.

The photosensitivity of the novel compositions can extend in general from about 150 nm to 600 nm, for example 190-600 nm, (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, low-, medium-, high- and super high-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 5 cm to 200 cm. Laser light sources, for example excimer lasers, such as $F_2$ excimer lasers at 157 nm exposure, KrF excimer lasers for exposure at 248 nm and ArF excimer lasers for exposure at 193 nm are also suitable. Further suitable are solid state UV lasers (e.g. Gemini from ManiaBarco, DI-2050 from PENTAX) and violet laser diodes with 405 nm output (DI-2080, DI-PDP from PENTAX). Lasers in the visible region can also be employed.

Curing may further be effected by exposing the compositions comprising the photoinitiators according to the present invention to a plasma, for example a plasma provided by a discharge in an arc or a plasma chamber.

The invention also provides a process for the photopolymerization of compounds containing ethylenically unsaturated double bonds, i.e. nonvolatile monomeric, oligomeric or polymeric compounds containing at least one ethylenically unsaturated double bond, which comprises irradiating a composition as described above with electromagnetic radiation, for example with light of the wavelength 150 to 600 nm, in particular 190-600 nm, with electron beam, or with X-rays. The invention further pertains to the use of a photoinitiator as described above for the photopolymerization of nonvolatile monomeric, oligomeric or polymeric compounds having at least one ethylenically unsaturated double bond by irradiation with light in the wavelength range from 150 to 600 nm.

The invention, as described above, provides compositions for the preparation of pigmented and nonpigmented surface coatings, printing inks, screen printing inks, offset printing inks, flexographic printing inks, ink jet printing inks, overprint varnishes, powder coatings, printing plates, adhesives, pressure-sensitive adhesives, dental materials, optical waveguides, optical switches, colour testing systems, composite materials, gel coats, glass-fibre cable coatings, screen printing stencils, resist materials, resist materials for printed circuit board production, primary imaging resist and solder resist, colour filters, resist materials for plasma display panel production, for the encapsulation of electrical and electronic components, for the preparation of magnetic recording materials, for the preparation of three-dimensional objects by means of stereolithography, of photographic reproductions, image recording material, for holographic recordings, for the preparation of decolouring materials, for the preparation of image recording materials using microcapsules; as well as a process for the preparation of pigmented and nonpigmented surface coatings, printing inks, screen printing inks, offset printing inks, flexographic printing inks, ink jet printing inks, powder coatings, printing plates, adhesives, pressure-sensitive adhesives, dental materials, optical waveguides, optical switches, colour testing systems, composite materials, gel coats, glass-fibre cable coatings, screen printing stencils, resist materials, resist materials for printed circuit board production, primary imaging resist and solder resist, colour filters, resist materials for plasma display panel production, for the encapsulation of electrical and electronic components, for the preparation of magnetic recording materials, for the preparation of three-dimensional objects by means of stereolithography, of photographic reproductions, image recording material, for holographic recordings, for the preparation of decolouring materials, for the preparation of image recording materials using microcapsules.

The invention further provides a coated substrate which is coated on at least one surface with a composition as described above, and describes a process for the photographic production of relief images, in which a coated substrate is subjected to imagewise exposure and then the unexposed portions are removed with a developer.

The new photoinitiators claimed in this patent application in particular efficiently allow the curing of clear coatings using UV-A light (320-450 nm). These curing conditions are especially useful for car refinish systems, decorative coatings, do it yourself and industrial applications. Application is mainly in combination with bisacylphosphine oxide photoinitiators (BAPO), where the mixtures with the new compounds exceed state-of-the-art α-hydroxyketone/BAPO mixtures regarding curing efficiency and color before and after cure as well as upon weathering.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case. All compounds of the following examples give analytical data in agreement with the proposed structures.

EXAMPLE 1

2-Benzoyl-2-hydroxy-cyclohexanecarboxylic acid

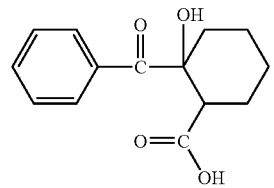 [SMILES: O=C(O)C1CCCCC1(O)C(=O)c1ccccc1]

1.1: 2-benzoyl-cyclohexanecarboxylic acid

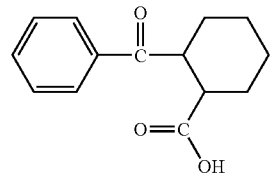 [SMILES: O=C(O)C1CCCCC1C(=O)c1ccccc1]

In a 2.5 l sulfuration flask equipped with a mechanical stirrer, thermometer and a refrigerator, 154.17 g (0.5 mol) of hexahydrophtalic anhydride are dissolved in 800 ml of benzene. The solution is cooled in an ice bath and 133.34 g (1.1 mol) of AlCl₃ are added portion wise over one hour while maintaining the temperature between 0° C. and 5° C. When the addition is complete, the ice bath is removed and the reaction mixture is stirred for 2 hours at room temperature and subsequently heated to reflux during one hour. After cooling to room temperature, the reaction mixture is poured onto a mixture of ice and water while stirring with a mechanical stirrer. The precipitated product is filtered off and washed several times with water until the pH of the wash water is neutral. The material is dried in vacuum and the remaining product dissolved in chloroform. The solution is filtered over hyflo and the volume of the filtrate reduced in vacuum. The product precipitates as an off-white solid that is filtered off, washed with additional solvent and dried in vacuum. 66 g (57% yield) of the product are obtained as a white solid with a melting point of 130-132° C. ¹H-NMR analysis is in agreement with the presence of a compound possessing the cis configuration of the substituents on the cyclohexane ring.

1.2: 3a-chloro-3-hydroxy-3-phenyl-hexahydro-isobenzofuran-1-one

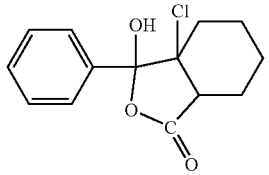 [SMILES: O=C1OC(O)(c2ccccc2)C2(Cl)CCCCC12]

1.2.1: Chlorination Using Chlorine 23.2 g (0.1 mol) of 2-benzoyl-cyclohexanecarboxylic acid and 100 ml of chorobenzene are heated to 55° C. while stirring. Chlorine gas is then slowly introduced into the suspension over two hours while maintaining the temperature at 58-60° C. When no more starting material is detected by thin layer chromatography (TLC) analysis, the slightly yellowish solution is purged with nitrogen during one hour and subsequently cooled to room temperature. The solvent is then distilled off in vacuum to give a yellowish oil which according to TLC analysis consists of two main products. These products are isolated via preparative column chromatography on silica gel, using white spirit/ethyl acetate 1:4 as the eluant. The first fraction isolated is obtained as white solid with a melting point of 89-92° C. and is identified by ¹H-NMR and elemental analysis as 3a-chloro-3-hydroxy-3-phenyl-hexahydro-isobenzofuran-1-one 9.3 g (35% yield). The second fraction is obtained as viscous yellowish oil, which is identified by ¹H-NMR and elemental analysis as 3,3a-dichloro-3-phenyl-hexahydro-isobenzofuran-1-one (6.7 g, 25% yield)

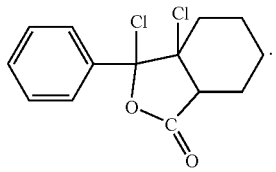 [SMILES: O=C1OC(Cl)(c2ccccc2)C2(Cl)CCCCC12]

1.2.2: Chlorination Using Sulfuryl Chloride 23.2 g (0.1 mol) of 2-benzoyl-cyclohexanecarboxylic acid are suspended in 60 ml of xylene at 55° C. 27.0 g (0.2 mol) of sulfurylchloride are subsequently added over 3 hours while maintaining the temperature at 51-55° C. The slightly greenish suspension is kept at this temperature for 7 hours until gas chromatography (GC) analysis indicates no more changes in the composition of the reaction mixture. The reaction mixture is cooled to room temperature, washed 4 times with water and the solvent is evaporated. GC analysis of the crude product indicates a composition of 66% 3a-chloro-3-hydroxy-3-phenyl-hexahydro-isobenzofuran-1-one and 24% of the dichloro compound 3,3a-dichloro-3-phenyl-hexahydro-isobenzofuran-1-one. This crude product mixture is used for the hydrolysis step without further purification.

1.3: 2-benzoyl-2-hydroxy-cyclohexanecarboxylic acid 1.3.1: Hydrolysis of 3a-chloro-3-hydroxy-3-phenyl-hexahydro-isobenzofuran-1-one Obtained According to 1.2.1 with Sodium Methanolate and Water 3.25 g of a 30% solution of sodium methanolate in methanol are diluted with 10 ml of methanol and heated to reflux. 4.0 g (0.015 mol) of 3a-chloro-3-hydroxy-3-phenyl-hexahydroisobenzofuran-1-one, obtained according to example 1.2.1, dissolved in 10 ml of methanol are added dropwise to this solution while stirring. The turbid reaction mixture is kept at reflux for one hour before 15 ml of methanol are distilled off. Then 20 ml of water are added dropwise and the resulting suspension is heated to 70° C. for one hour. After cooling to room temperature, ethyl acetate is added and the organic phase is separated. The basic aqueous solution is neutralized an extracted several times with ethyl acetate. The combined organic phases are dried over magnesium sulfate, the solvent is evaporated in vacuum the residual viscous crude product purified by chromatography on silica gel using petroleum ether/ethyl acetate 8:1 as the eluant. 2.8 g (72%) of 2-benzoyl-2-hydroxy-cyclohexane carboxylic acid are obtained as viscous material that solidifies upon standing. White solid with a mp. 165-167° C.

1.3.2: Hydrolysis of the Product Mixture Obtained According to 1.2.2

The crude product mixture obtained as described in example 1.2.2 is dissolved in 85 ml of xylene at room temperature. 75 g of aqueous 15% NaOH (0.28 mol NaOH) are added dropwise to this solution while stirring and cooling in a water bath. While the temperature rises to 33° C., a yellowish suspension is formed in the reaction mixture which turns into a viscous mass while stirring over night at room temperature. The mixture is cooled in an ice bath and 25 ml of concentrated HCl are slowly added until a pH of 1 is measured. The suspension is now easily stirrable and the crude product is filtered off and washed with xylene. The product is purified by recrystallization from methanol/water 70:5 to give 2-benzoyl-2-hydroxycyclohexanecarboxylic acid as a white solid with a melting point of 166-167° C. Yield 9.2 g, 37% based on 2-benzoyl-cyclohexanecarboxylic acid.

EXAMPLES 2-7

The compounds of examples 2-7 are prepared following the same procedure as described for example 1, except that the aromatic compound listed in Table 1 is used instead of benzene in step 1.1.

TABLE 1

| ex. | starting material | structure | name | mp [°C.] |
|---|---|---|---|---|
| 2 | toluene | 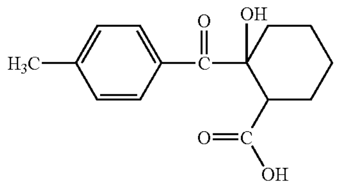 [SMILES: Cc1ccc(C(=O)C2(O)CCCCC2C(=O)O)cc1] | 2-hydroxy-2-(4-methylbenzoyl)-cyclohexane-carboxylic acid | 143-147 |
| 3 | 1,2-xylene | 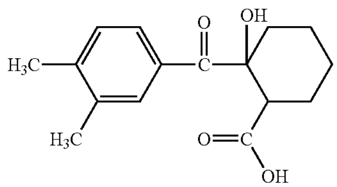 [SMILES: Cc1ccc(C(=O)C2(O)CCCCC2C(=O)O)cc1C] | 2-(3,4-dimethyl-benzoyl)-2-hydroxy-cyclohexanecarboxylic acid | 161-163 |
| 4 | 1,3-xylene | 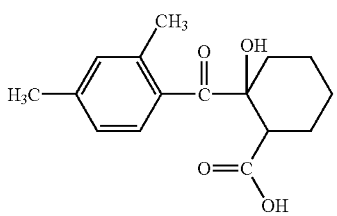 [SMILES: Cc1ccc(C(=O)C2(O)CCCCC2C(=O)O)c(C)c1] | 2-(2,4-dimethyl-benzoyl)-2-hydroxy-cyclohexanecarboxylic acid | 116-117 |
| 5 | isopropyl benzene | 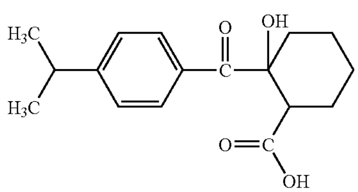 [SMILES: CC(C)c1ccc(C(=O)C2(O)CCCCC2C(=O)O)cc1] | 2-hydroxy-2-(4-isopropyl-benzoyl)-cyclohexanecarboxylic acid | 153-157 |
| 6 | anisole | 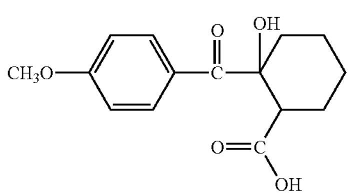 | 2-hydroxy-2-(4-methoxy-benzoyl)-cyclohexane carboxylic acid | 121-123 |
| 7 | chlorobenzene | 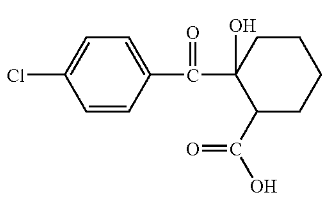 [SMILES: O=C(O)C1CCCCC1(O)C(=O)c1ccc(Cl)cc1] | 2-(4-chloro-benzoyl)-2-hydroxy-cyclohexanecarboxylic acid | 172-174 |

EXAMPLES 8-9

The compounds of examples 8 and 9 (Table 2) are prepared by an analogous reaction sequence as given in example 1, with the exception that the functional group on the aromatic starting material is protected before the Friedel-Crafts acylation is performed.

solution over 1 hour 40 minutes while keeping the temperature at 20° C. After addition of ⅓–½ equivalent of the bromine solution, a yellowish suspension is formed. The reaction mixture is stirred for 30 minutes at 20° C., followed by 1 hour at 0° C. in order to achieve complete precipitation of the product. The yellowish solid is filtered and washed with acetic phenyl)-3-oxo-octahydro-isobenzo-furan-1-yl acetate as a

TABLE 2

| ex. | starting material | structure | name | mp [°C.] |
|---|---|---|---|---|
| 8 | 2-hydroxyethyl benzene | 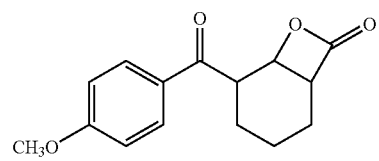 | 2-hydroxy-2-[4-(2-hydroxy-ethyl)-benzoyl]-cyclo-hexanecarboxylic acid | resin |
| 9 | phenyl acetic acid | 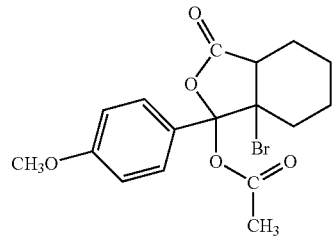 | 2-(4-carboxymethyl-benzoyl]-2-hydroxy-cyclo-hexanecarboxylic acid | — |

EXAMPLE 10

6-(4-Methoxy-benzoyl)-7-oxa-bicyclo[4.2.0]octan-8-one 10.1: 7a-bromo-1-(4-methoxy-phenyl)-3-oxo-octahydro-isobenzo-furan-1-yl acetate 40 g (0.153 mol) of 2-hydroxy-2-(4-methoxy-benzoyl)-cyclohexanecarboxylic acid (=compound of example 6) are dissolved in 125 ml of acetic anhydride. 24.37 g (0.153 mol) of bromine in 24 ml of acetic acid are added slowly to this yellowish-white solid that is dried in vacuum at 40° C. and used for the next step without further purification.

10.2: Preparation of a Mixture of 2-bromo-2-(4-methoxy-benzoyl)-cyclohexanecarboxylic acid and 3a-bromo-3-hydroxy-3-(4-methoxy-phenyl)-hexahydro-isobenzofuran-1-one

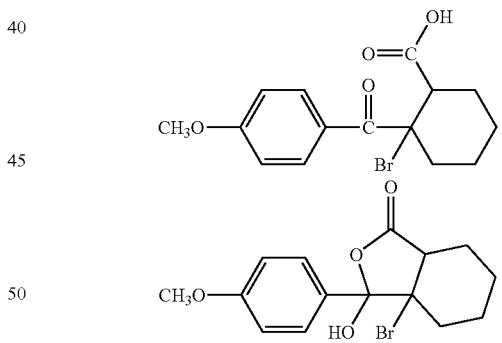

The crude product prepared according to example 10.1 is dissolved in 180 ml of acetic acid. 23.7 ml of concentrated HCl are slowly added to the solution while stirring. The resulting suspension is heated to 50° C. and turns into a clear solution. TLC analysis shows no remaining starting material, and the solution is quickly cooled to room temperature and subsequently poured under vigorous stirring onto 600 ml of water. The precipitated product is filtered off and washed several times with water. The crude material is dissolved in 200 ml of ethyl acetate and the organic solution is washed twice with 250 ml water. The water phase is extracted twice with ethyl acetate, the united organic phases are dried over Na₂SO₄ and the solvent is distilled off in vacuum. The white solid thus obtained (44 g, 97%) according to ¹H-NMR analysis consists of approximately 69% 2-bromo-2-(4-methoxy-benzoyl)-cyclohexanecarboxylic acid and 31% 3a-bromo-3-hydroxy-3-(4-methoxy-phenyl)-hexahydro-isobenzo-furan-1-one. This mixture is used without further purification in the next reaction step.

10.3: Preparation of 6-(4-methoxy-benzoyl)-7-oxa-bicyclo[4.2.0]octan-8-one

The crude product prepared according to example 10.2 is dissolved in 135 ml of tert-butyl methyl ether and slowly dropped into a solution of 7 g NaHCO$_3$ in 340 ml water. The mixture is stirred and 12 ml of an 8% solution of NaHCO$_3$ are added portionwise to keep a pH of 7. After stirring for one hour, the organic phase is separated, dried over sodium sulfate and the solvent is distilled off in vacuum. 20.8 g (62%) 6-(4-methoxy-benzoyl)-7-oxa-bicyclo[4.2.0]-octan-8-one is obtained as a white solid with a mp of 77.5-78.5° C.

EXAMPLES 11-12

The compounds of examples 11 and 12 (Table 3) are prepared following the same procedure as given for example 10, except that the carboxylic acid derivatives reported in Table 3 are used as starting materials.

is kept at this temperature for 4 hours and subsequently heated to reflux over night. The reaction mixture is cooled to room temperature and the solvent distilled off in vacuum. The remaining yellowish mass is washed several times with cold hexane and dried in vacuum. The product 2-hydroxy-2-(4-methoxy-benzoyl)-cyclohexanecarboxylate dipropyl-ammonium is quantitatively obtained as a beige solid with a melting point of 114-124° C.

EXAMPLE 14

2-(3,4-Dimethyl-benzoyl)-2-hydroxy-cyclohexanecarboxylate dipropyl ammonium

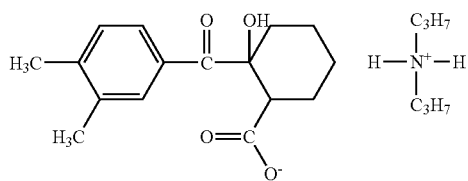

TABLE 3

| ex. | carboxylic acid | structure | name | mp [°C.] |
|---|---|---|---|---|
| 11 | ![structure] of example 1 | ![structure] | 6-benzoyl-7-oxa-bicyclo-[4.2.0]octan-8-one | liquid |
| 12 | ![structure] of example 3 | ![structure] | 6-(3,4-dimethyl-benzoyl)-7-oxa-bicyclo[4.2.0]octan-8-one | 62-64 |

EXAMPLE 13

2-Hydroxy-2-(4-methoxy-benzoyl)-cyclohexanecarboxylate dipropyl-ammonium

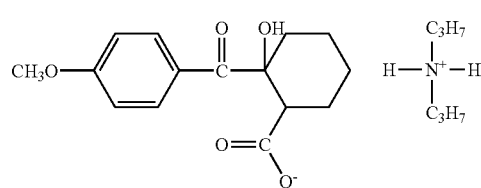

6.96 g (0.025 mol) of the compound of example 6 and 2.53 g of dipropylamine and 50 ml of toluene are heated to 65° C. in a 100 ml reaction flask while stirring. The white dispersion 5.53 g (0.02 mol) of 2-(3,4-dimethyl-benzoyl)-2-hydroxy-cyclohexanecarboxylic acid (=compound of example 3) are dissolved in 30 ml of acetone. A solution of 2.02 g (0.02 mol) of dipropylamine in 30 ml of acetone and the reaction mixture are stirred at room temperature for 30 minutes. The solvent is evaporated in vacuum and the remaining residue is dried in vacuum. 7.4 g of 2-(3,4-dimethyl-benzoyl)-2-hydroxy-cyclohexanecarboxylate dipropyl-ammonium are obtained as slightly yellowish crystals with a melting range of 122-129° C.

EXAMPLES 15-32

The compounds of examples 15-32 (Table 4) are prepared following the same procedure as described for example 15, except that the 2-benzoyl-2-hydroxy-cyclohexanecarboxylic acid derivatives and the amines listed in Table 4 are used as starting materials.

TABLE 4

| ex. | carboxylic acid/ amine | structure and name | mp [°C.] |
|---|---|---|---|
| 15 | ex. 1/ H₂N—(CH₂)₃—Si(OH)₂—OC₂H₅ | 2-benzoyl-2-hydroxy-cyclohexanecarboxylate 3-(ethoxy-dihydroxy-silanyl) propyl ammonium | resin |
| 16 | ex. 3/ (H₃C)₂N—(CH₂)₂—N(CH₃)₂ | 2-(3,4-dimethyl-benzoyl)-2-hydroxy-cyclohexane-carboxylate (2-dimethylamino-ethyl)-dimethyl-ammonium | resin |
| 17 | ex. 3/ (H₃C)₂N—(CH₂)₃—NH₂ | 2-(3,4-Dimethyl-benzoyl)-2-hydroxy-cyclohexanecarboxylate (3-aminopropyl)-dimethyl-ammonium | resin |
| 18 | ex. 3/ (C₂H₅)₂N—(CH₂)₃—NH₂ | 2-(3,4-dimethyl-benzoyl)-2-hydroxy-cyclohexanecarboxylate (3-amino-propyl)-diethyl-ammonium | resin |
| 19 | ex. 3/ H₃C—N(CH₂CH₂OH)₂ | 2-(3,4-dimethyl-benzoyl)-2-hydroxy-cyclohexanecarboxylate bis-(2-hydroxy-ethyl)-methyl-ammonium | resin |
| 20 | ex. 3/ [bis-(2-hydroxy-propyl)-amino-ethyl]-bis-(2-hydroxy-propyl)amine | 2-(3,4-dimethyl-benzoyl)-2-hydroxy-cyclohexanecarboxylate {2-[bis-(2-hydroxy-propyl)-amino]-ethyl}-bis-(2-hydroxy-propyl)-ammonium | glass |

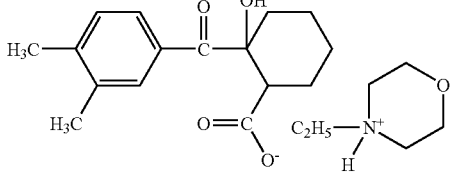

TABLE 4-continued

| ex. | carboxylic acid/ amine | structure and name | mp [°C.] |
|---|---|---|---|
| 27 | ex. 6/ morpholine-N-C₂H₅ | 2-hydroxy-2-(4-methoxy-benzoyl)-cyclohexane-carboxylate 4-ethyl-morpholin-4-ium | 55-58 |
| 28 | ex. 6/ (CH₃)₂N-(CH₂)₂-N(CH₃)₂ | 2-hydroxy-2-(4-methoxy-benzoyl)-cyclohexane-carboxylate (2-dimethylamino-ethyl)-dimethyl-ammonium | 132-142 |
| 29 | ex. 6/ H₃C-N(CH₂CH₂OH)₂ | 2-hydroxy-2-(4-methoxy-benzoyl)-cyclohexane-carboxylate 4-(1,1-dimethyl-2-oxo-2-phenyl-ethyl)-morpholin-4-ium | 95-99 |
| 30 | ex. 6/ Ph-CO-C(CH₃)₂-N(morpholine) | 2-hydroxy-2-(4-methoxy-benzoyl)-cyclohexane-carboxylate 4-(1,1-dimethyl-2-oxo-2-phenyl-ethyl)-morpholin-4-ium | resin |
| 31 | ex. 6/ Ph-CO-(CH₂)₂-N(CH₃)₂ | 2-Hydroxy-2-(4-methoxy-benzoyl)-cyclohexane-carboxylate dimethyl-(3-oxo-3-phenyl-propyl)-ammonium | resin |

TABLE 4-continued

| carboxylic acid/ ex. amine | structure and name | mp [°C.] |
|---|---|---|
| 32 ex. 6/ | 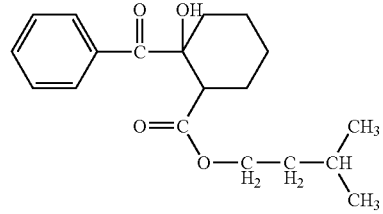<br>2-hydroxy-2-(4-methoxy-benzoyl)-cyclohexane-carboxylate {2-[bis-(2-hydroxy-propyl)-amino]-ethyl}-bis-(2-hydroxy-propyl)-ammonium | glass |

EXAMPLE 33

2-Benzoyl-2-hydroxy-cyclohexanecarboxylic acid methyl ester

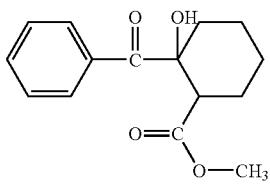 [SMILES: COC(=O)C1CCCCC1(O)C(=O)c1ccccc1]

9.93 g (0.04 mol) of 2-benzoyl-2-hydroxy-cyclohexanecarboxylic acid prepared according to the method of example 1 and 1.4 g of methanol (0.044 mol) are dissolved in 200 ml of dichloromethane. 9.91 g (0.044 mol) dicyclohexylcarbodiimide are added to the solution and the resulting suspension is stirred for 3 hours at room temperature. After this time, no more carboxylic acid is detected by TLC analysis. The reaction mixture is filtered and the solid dicyclohexylurethane is washed with dichloromethane. The organic solution is washed with sodium bicarbonate and water, dried over $MgSO_2$ and evaporated in vacuum. The residual crude product is purified by chromatography on silica gel (eluant: petroleum ether/ethyl acetate 9:1) to give 7.03 g (71%) 2-benzoyl-2-hydroxy-cyclohexanecarboxylic acid methyl ester as a viscous resin.

$^1$H-NMR ($CDCl_3$), δ [ppm]: 8.31 (dxd, 2 aromt H); 7.55-7.35 (m. 3 aromt. H); 4.63 (d, OH); 3.65 (s, 3H, $OCH_3$); 3.14 (1H, dxd, H—C(1)); 2.25 (1H); 2.05-1.2 (m, 7H).

EXAMPLE 34

2-Benzoyl-2-hydroxy-cyclohexanecarboxylic acid 3-methyl-butyl ester 10 g (0.04 mol) of 2-benzoyl-2-hydroxy-cyclohexanecarboxylic acid (of example 1), 7.05 mol 3-methyl-butan-1-ol and 0.5 g $H_2SO_4$ are dissolved in 200 ml $CHCl_3$ and heated to reflux during 18 hours using a water separator to remove the water formed during the reaction. The reaction mixture is then cooled to room temperature, washed with sodium bicarbonate and water and dried over $Mg_2SO_4$. After distillation of the solvent, the crude reaction product is purified by flash chromatography (silica gel, eluant petroleum ether/ethyl acetate 1:1) to give 3 g 2-benzoyl-2-hydroxy-cyclohexanecarboxylic acid 3-methyl-butyl ester as a colorless liquid.

$^1$H-NMR ($CDCl_3$), δ [ppm]: 8.21 (dxd, 2 aromt H); 7.55-7.35 (m. 3 aromt. H); 4.70 (d, OH); 4.09 (m, 2H—O—$CH_2$—); 3.13 (1H, dxd, H—C(1)); 2.25 (1H); 2.05-1.2 (m, 13H); 0.90 (d, 6H).

EXAMPLES 35-44

The compounds of examples 35-44, which are listed in Table 5 are prepared following the procedure of example 33, except that the carboxylic acid derivatives and the alcohol reported in the table are used as starting materials. In the preparation of the compounds of examples 42-44 toluene is used as solvent. For the preparation of monoesters of diols, a large excess of the diol is used as indicated in the table.

TABLE 5

| ex. | carboxylic acid/ alcohol | structure and name | mp [°C.] |
|---|---|---|---|
| 35 | ex. 1/ ethanol | 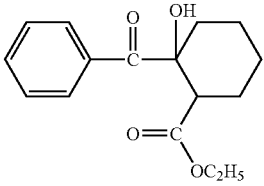 [SMILES: CCOC(=O)C1CCCCC1(O)C(=O)c1ccccc1] 2-benzoyl-2-hydroxy-cyclohexanecarboxylic acid ethyl ester | liquid |
| 36 | ex. 1/ 1,4-butandiol 10 equivalents | 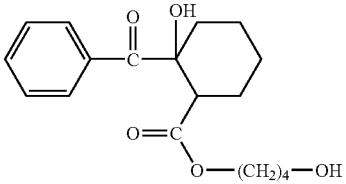 2-benzoyl-2-hydroxy-cyclohexanecarboxylic acid 4-hydroxy-butyl ester | liquid |
| 37 | ex. 2/ ethanol | 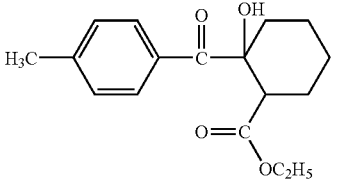 [SMILES: CCOC(=O)C1CCCCC1(O)C(=O)c1ccc(C)cc1] 2-hydroxy-2-(4-methylbenzoyl)-cyclo-hexanecarboxylic acid ethyl ester | liquid |
| 38 | ex. 3/ ethanol | 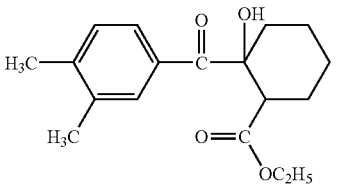 2-(3,4-dimethyl-benzoyl)-2-hydroxy-cyclohexanecarboxylic acid ethyl ester | viscous oil |
| 39 | ex. 4/ ethanol | 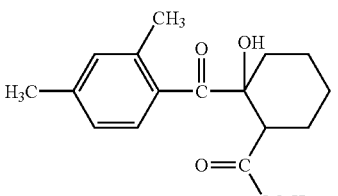 2-(2,4-dimethyl-benzoyl)-2-hydroxy-cyclohexanecarboxylic acid ethyl ester | viscous oil |
| 40 | ex. 5/ ethanol | 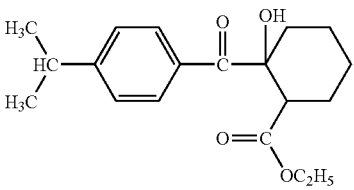 [SMILES: CCOC(=O)C1CCCCC1(O)C(=O)c1ccc(C(C)C)cc1] 2-hydroxy-2-(4-isopropyl-benzoyl)-cyclohexane-carboxylic acid ethyl ester | viscous oil |

TABLE 5-continued

| ex. | carboxylic acid/ alcohol | structure and name | mp [°C.] |
|---|---|---|---|
| 41 | ex. 6/ ethanol | 2-hydroxy-2-(4-methoxy-benzoyl)-cyclohexane-carboxylic acid ethyl ester | liquid |
| 42 | ex. 6/ 1,2-ethandiol 10 equivalents | 2-hydroxy-2-(4-methoxy-benzoyl)-cyclohexane-carboxylic acid 2-hydroxy-ethyl ester | 84-89 |
| 43 | ex. 6/ diethylene-gycole 10 equivalents | 2-hydroxy-2-(4-methoxy-benzoyl)-cyclohexane-carboxylic acid 2-(hydroxy-ethoxy)-ethyl ester | resin |
| 44 | ex. 7/ ethanol | 2-(4-chloro-benzoyl)-2-hydroxy-cyclohexanecarboxylic acid ethyl ester | viscous oil |

EXAMPLES 45-54

The polyester compounds of examples 45-47, and 49-54 listed in Table 6 are prepared following the procedure as described in example 34, but using toluene as the solvent and 0.5 equivalents of the diol per equivalent of the carboxylic acid derivatives. The compound of example 48 is prepared following the procedure as described in example 33, but using 0.33 equivalents of the triol per equivalent of the carboxylic acid derivatives. In case of examples 45-47 and 49-54, the crude products are mixtures containing both the mono- and the diester of the diol. Example 48 is obtained as a mixture of the mono-, di- and triester of the triol. The compounds are separated by flash chromatography, using petroleum ether/ ethyl acetate 9:1 as the eluant.

TABLE 6

| ex. | carboxylic acid/ alcohol | structure and name | mp [°C.] |
|---|---|---|---|
| 45 | ex. 1/ 1,2-ethandiol 0.5 equivalents | 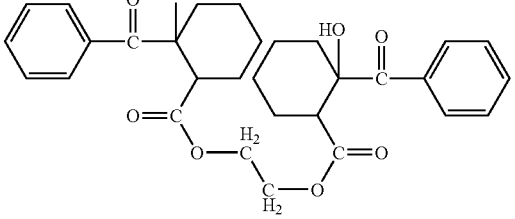 2-benzoyl-2-hydroxy-cyclohexanecarboxylic acid 2-((1S,2R)-2-benzoyl-2-hydroxy-cyclohexane-carbonyloxy)-ethyl ester | resin |
| 46 | ex. 1/ 1,4-butandiol 0.5 equivalents | 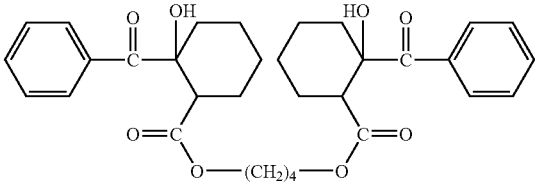 2-benzoyl-2-hydroxy-cyclohexanecarboxylic acid 4-((1S,2R)-2-benzoyl-2-hydroxy-cyclohexane-carbonyloxy)-butyl ester | 81-85 |
| 47 | ex. 1/ 1,6-hexanediol 0.5 equivalents | 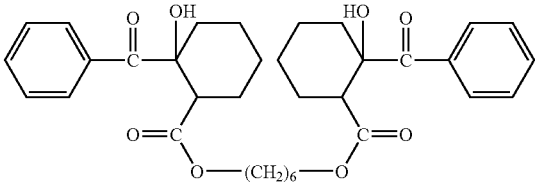 2-benzoyl-2-hydroxy-cyclohexanecarboxylic acid 6-((1S,2R)-2-benzoyl-2-hydroxy-cyclohexane-carbonyloxy)-hexyl ester | 94-99 |
| 48 | ex. 1/ triethanol-amine 0.33 equivalents | 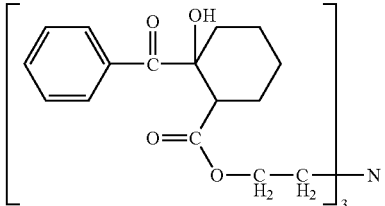 2-benzoyl-2-hydroxy-cyclohexanecarboxylic acid 2-{[2-((1S,2R)-2-benzoyl-2-hydroxy-cyclo-hexanecarbonyloxy)-ethyl]-[2-((1S,2R)-2-benzoyl-2-hydroxy-cyclohexanecarbonyloxy)-ethyl]-amino}-ethyl ester | resin |
| 49 | ex. 2/ 1.6-hexandiol 0.5 equivalents | 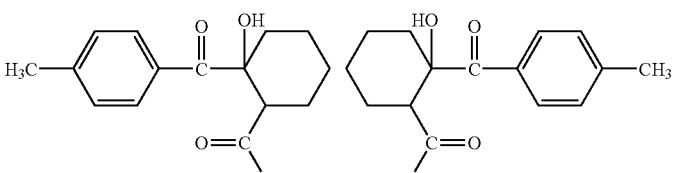 2-hydroxy-2-(4-methyl-benzoyl)-cyclo-hexanecarboxylic acid 6-[(1S,2R)-2-hydroxy-2-(4-methyl-benzoyl)-cyclohexanecarbonyloxy]-hexyl ester | resin |
| 50 | ex. 3/ 1.6-hexandiol 0.5 equivalents | 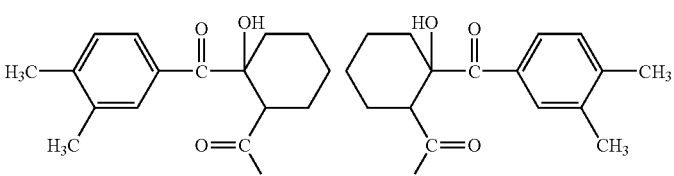 2-(3,4-Dimethyl-benzoyl)-2-hydroxy-cyclo-hexanecarboxylic acid 6-[(1S,2R)-2-(3,4-dimethyl-benzoyl)-2-hydroxy-cyclohexanecarbonyloxy]-hexyl ester | resin |

TABLE 6-continued

| ex. | carboxylic acid/ alcohol | structure and name | mp [°C.] |
|---|---|---|---|
| 51 | ex. 3/ diethyleneglycole 0.5 equivalents | 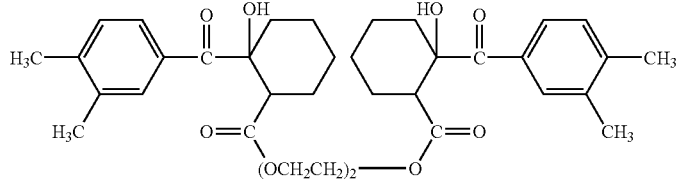<br>2-(3,4-dimethyl-benzoyl)-2-hydroxy-cyclo-hexanecarboxylic acid<br>2-{2-[(1S,2R)-2-(3,4-dimethyl-benzoyl)-2-hydroxy-cyclohexanecarbonyloxy]-ethoxy}-ethyl ester | resin |
| 52 | ex. 3/ triethylenegycole 0.5 equivalents | 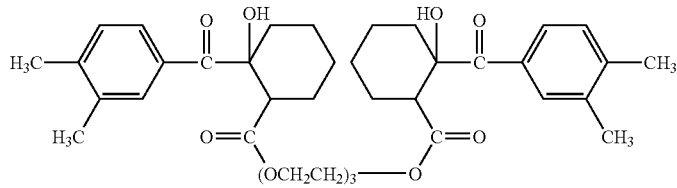<br>2-(3,4-dimethyl-benzoyl)-2-hydroxy-cyclo-hexanecarboxylic acid<br>2-(2-{2-[(1S,2R)-2-(3,4-dimethyl-benzoyl)-2-hydroxy-cyclohexane-carbonyloxy]-ethoxy}-ethoxy)-ethyl ester | resin |
| 53 | ex. 6/ 1,6-hexanediol 0.5 equivalents | 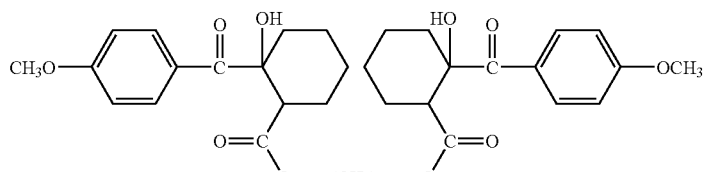<br>2-hydroxy-2-(4-methoxy-benzoyl)-cyclo-hexanecarboxylic acid<br>2-{2-[(1S,2R)-2-hydroxy-2-(4-methoxy-benzoyl)-cyclohexanecarbonyloxy]-ethoxy}-ethyl ester | resin |
| 54 | ex. 6/ diethylene-gycole 0.5 equivalents | 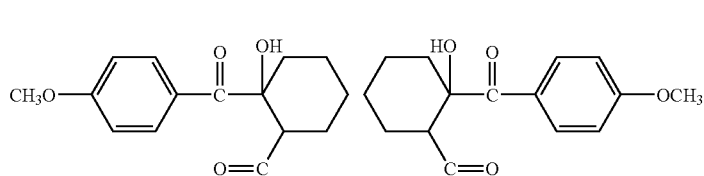<br>2-hydroxy-2-(4-methoxy-benzoyl)-cyclo-hexanecarboxylic acid<br>2-{2-[(1S,2R)-2-hydroxy-2-(4-methoxy-benzoyl)-cyclohexanecarbonyloxy]-ethoxy}-ethyl ester | resin |

EXAMPLES 55 AND 56

2-Hydroxy-2-(4-methoxy-benzoyl)-cyclohexanecarboxylic acid 2,2,3,3,4,4,5,5-octafluoro-6-hydroxy-hexyl ester (Example 55) and 2-hydroxy-2-(4-methoxy-benzoyl)-cyclohexanecarboxylic acid 2,2,3,3,4,4,5,5-octafluoro-6-[2-hydroxy-2-(4-methoxy-benzoyl)-cyclohexanecarbonyloxy]-hexyl ester (Example 56)

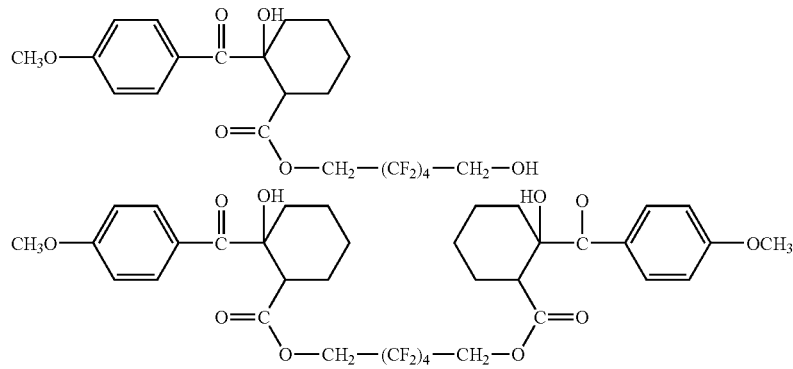

35.4 g (0.136 mol) of 6-(4-methoxybenzoyl)-7-oxa-bicyclo[4.2.0]octan-8-one (=compound of example 10) are dissolved in 100 ml dichloromethane. A catalytic amount of $H_2SO_4$ and 17.83 g of 2,2,3,3,4,4,5,5-octafluorohexan-1,6-diol are added and the reaction mixture is stirred at room temperature during 48 hours. After this time, TLC analysis indicates consumption of the starting material and the formation of two main products. The solvent is evaporated in vacuum and the residual dark mixture filtered over silica gel. ¹H-NMR analysis indicates a mixture of 53% the monoester and 47% of the diester. The two compounds are subsequently purified and separated by repeated chromatography on silica gel using heptane/ethyl acetate 6:4 as eluant. 2.24 g of a fraction containing the pure monoester 2-hydroxy-2-(4-methoxy-benzoyl)-cyclohexanecarboxylic acid 6-hydroxy-2,2,3,3,4,4,5,5-octafluoro-hexyl ester (=compound of example 55) are isolated, besides a fraction containing 5 g of the pure diester 2-hydroxy-2-(4-methoxy-benzoyl)-cyclohexanecarboxylic acid 2,2,3,3,4,4,5,5-octafluoro-6-[2-hydroxy-2-(4-methoxy-benzoyl)-cyclohexanecarbonyloxy]-hexyl ester (=compound of example 56), and a fraction of 8.6 g that is a mixture of the monoester (53%) and the diester (47%).

2-Hydroxy-2-(4-methoxy-benzoyl)-cyclohexanecarboxylic acid 2,2,3,3,4,4,5,5-octafluoro-6-hydroxy-hexyl ester (Example 55)

¹H-NMR (CDCl₃), δ [ppm]: 8.29 (d, 2 aromt H); 6.92 (d. 2 aromt. H); 4.74 (q, 1H, COOCH₂CF₂); 4.43 (q, 1H, COOCH₂CF₂); 4.4 (d, OH); 4.09 (t, 2H, —CF₂CH₂OH); 3.88 (s, 3H, CH₃O); 3.27 (dxd, H—C(1)); 2.66 (br s, OH); 2.25 (dxd, 1H); 2.1-1.2 (m, 8H).

2-Hydroxy-2-(4-methoxy-benzoyl)-cyclohexanecarboxylic acid 2,2,3,3,4,4,5,5-octafluoro-6-[2-hydroxy-2-(4-methoxy-benzoyl)-cyclohexanecarbonyloxy]-hexyl ester (Example 56)

¹H-NMR (CDCl₃), δ [ppm]: 8.30 (d, 4 aromt H); 6.92 (d. 4 aromt. H); 4.77 (q, 2H, COOCH₂CF₂); 4.40 (q, 2H, COOCH₂CF₂); 4.37 (d, OH); 3.88 (s, 6H, CH₃O); 3.27 (dxd, 2H—C(1)); 2.25 (dxd, 2H); 2.1-1.2 (m, 16H).

EXAMPLE 57

3,7,11,15-Tetrakis-(3-{2-[2-hydroxy-2-(4-methoxy-benzoyl)-cyclohexane-carbonyloxy]-ethoxy}-propyl)-octadecamethyl-decasiloxane

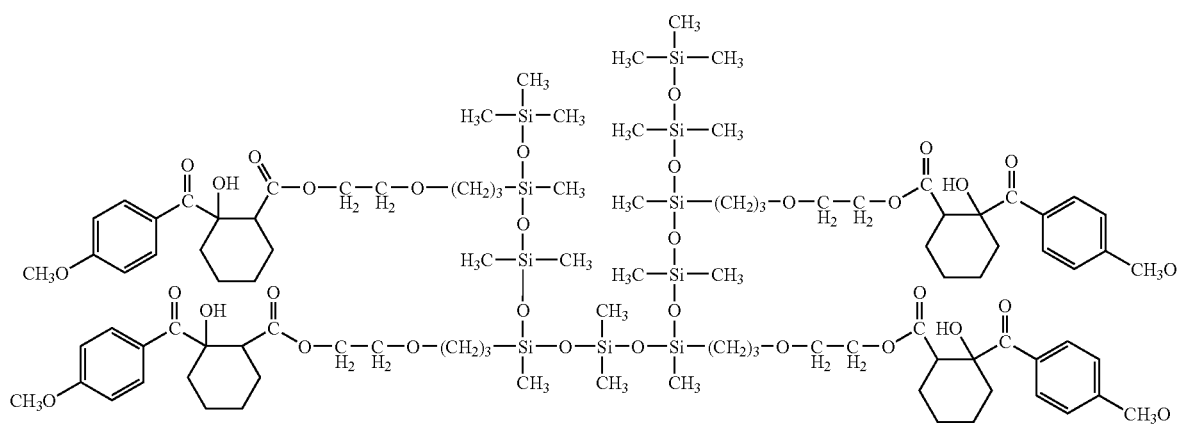 [SMILES: COc1ccc(C(=O)C2(O)CCCCC2C(=O)OCCOCCC[Si](C)(O[Si](C)(C)C)O[Si](C)(C)O[Si](C)(CCCOCCOC(=O)C2CCCCC2(O)C(=O)c2ccc(OC)cc2)O[Si](C)(C)O[Si](C)(CCCOCCOC(=O)C2CCCCC2(O)C(=O)c2ccc(C=O)cc2)O[Si](C)(C)O[Si](C)(CCCOCCOC(=O)C2CCCCC2(O)C(=O)c2ccc(C=O)cc2)O[Si](C)(C)O[Si](C)(C)C)cc1]

This compound is prepared following the procedure described for example 55, using 3.32 g (approximately 0.003 mol) of the siloxane carbinol QC 02668 (Wacker) and 3.12 g (0.012 mol) of 6-(4-methoxy-benzoyl)-7-oxa-bicyclo[4.2.0]octan-8-one (example 10) as starting material. After the evaporation of the solvent, the brownish crude product is filtered over silica gel to give 5 g (approximately 78%) of 3,7,11,15-tetrakis-(3-{2-[2-hydroxy-2-(4-methoxybenzoyl)-cyclohexanecarbonyloxy]-ethoxy}-propyl)-octadecamethyl-decasiloxane as a viscous oil. An estimation from the $^1$H-NMR suggests that approximately 3.25 of the 4 hydroxyl groups per siloxane carbinol are esterified.

$^1$H-NMR (CDCl$_3$), δ [ppm]: 8.30 (d, aromt H); 6.93 (d, aromt. H); 5.5, broad s, OH; 4.18 (m, —COO—CH$_2$—); 3.89 (s, CH$_3$O); 3.7-3.3 (m, —CH$_2$—O—CH$_2$—); 3.20 (dxd, H—C(1)); 2.30-1.2 (m); 0.55 (m, —CH$_2$—Si); 0.1 (overlapping s, —Si—CH$_3$).

EXAMPLE 58

2-Hydroxy-2-(4-methoxy-benzoyl)-cyclohexanecarboxylic acid butyl-amide

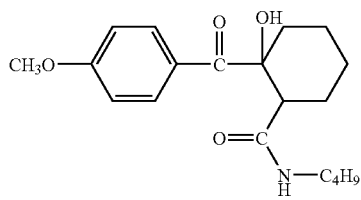

20.8 g (0.08 mol) of 6-(4-methoxy-benzoyl)-7-oxa-bicyclo[4.2.0]octan-8-one (example 10) are dissolved in 200 ml of tert-butyl methyl ether. 10.46 g (0.143 mol) of n-butylamine are slowly added to this solution over one hour. The reaction mixture is stirred overnight at room temperature and the solvent is subsequently distilled off under vacuum. The yellowish oil thus obtained crystallizes upon standing and is purified by recrystallization from heptane. 22.5 g (85%) 2-(4-methoxybenzoyl)-2-hydroxy-cyclohexanecarboxylic acid butyl-amide are thus obtained as white solid with a melting point of 94-95° C.

$^1$H-NMR (CDCl$_3$), δ [ppm]: 8.31 (dxd, 2 aromt H); 6.90 (dxd, 2 aromat H); 6.06 (broad s, OH); 5.91 (broad t, NH): 3.86 (s, 3H, CH$_3$O); 3.21 (q, 2H, —NH—CH$_2$—); 2.89 (1H, dxd, H—C(1)); 2.19 (m, 1H); 2.05-1.2 (m, 12H); 0.90 (t, 3H, —CH$_2$—CH$_3$).

EXAMPLES 59-65

The compounds of examples 59-65 (Table 7) are prepared following the procedure described for example 58, using the lactones and amines reported in Table 7 as starting materials.

TABLE 7

| ex. | lactone/amine | structure and name | mp [°C.] |
|---|---|---|---|
| 59 | ex. 11/ H$_2$N—C$_4$H$_9$ | 2-benzoyl-2-hydroxy-cyclohexanecarboxylic acid butyl-amide | 75-77 |
| 60 | ex. 11/ H$_3$C—NH—C$_4$H$_9$ | 2-benzoyl-2-hydroxy-cyclohexanecarboxylic acid butyl-methyl-amide | oil |

TABLE 7-continued

| ex. | lactone/amine | structure and name | mp [°C.] |
|---|---|---|---|
| 61 | ex. 11/ (piperidine-4-carboxylic acid ethyl ester) | 1-(2-benzoyl-2-hydroxy-cyclohexanecarbonyl)-piperidine-4-carboxylic acid ethyl ester | viscous oil |
| 62 | ex. 12/ H$_3$C—NH—C$_4$H$_9$ | 2-(3,4-dimethyl-benzoyl)-2-hydroxy-cyclohexane-carboxylic acid butyl-methyl-amide | viscous oil |
| 63 | ex. 10/ H$_3$C—NH—C$_4$H$_9$ | 2-hydroxy-2-(4-methoxy-benzoyl)-cyclohexane-carboxylic acid butyl-methyl-amide | oil |
| 64 | ex. 10/ H$_3$C—(CH$_2$)$_3$—Si(CH$_3$)(OSi(CH$_3$)$_3$)$_2$ | 2-hydroxy-2-(4-methoxy-benzoyl)-cyclohexane-carboxylic acid 3-[bis(trimethylsiloxy)-methyl-silanyl]propyl-amide | 77-79 |
| 65 | ex. 10/ H$_2$N—(CH$_2$)$_3$—Si(OSi(CH$_3$)$_3$)$_3$ | 2-hydroxy-2-(4-methoxy-benzoyl)-cyclohexane-carboxylic acid 3-[tris(trimethylsiloxy)silanyl]propyl-amide | 72-73 |

EXAMPLES 66-75

The compounds of examples 66-75 (Table 8) are prepared following the procedure described for example 58, using the lactones and 0.5 mol-equivalents of the diamines reported in Table 8.

TABLE 8

| ex. | lactone/diamine | structure and name | mp [°C.] |
|---|---|---|---|
| 66 | ex. 11/ H₂N—CH₂—CH₂—NH₂ | 2-benzoyl-2-hydroxy-cyclohexanecarboxylic acid {2-[(2-benzoyl-2-hydroxy-cyclohexanecarbonyl)-methyl-amino]-ethyl}-methyl-amide | foam |
| 67 | ex. 11/ HN⟨piperidine⟩—(CH₂)₃—⟨piperidine⟩NH | [2-(4-{3-[1-(2-benzoyl-2-hydroxy-cyclohexane-carbonyl)-piperidin-4-yl]-propyl}-piperidine-1-carbonyl)-1-hydroxy-cyclohexyl]-phenyl-methanone | foam |
| 68 | ex. 11/ O—(CH₂)₂—NH₂ / (CH₂)₂ / O—(CH₂)₂—NH₂ | 2-benzoyl-2-hydroxy-cyclohexanecarboxylic acid [2-(2-{2-[(2-benzoyl-2-hydroxy-cyclohexanecarbonyl)-amino]-ethoxy}-ethoxy)-ethyl]-amide | resin |
| 69 | ex. 12/ HN⟨piperidine⟩—(CH₂)₃—⟨piperidine⟩NH | {2-[4-(3-{1-[2-(3,4-dimethyl-benzoyl)-2-hydroxy-cyclohexanecarbonyl]-piperidin-4-yl}-propyl)-piperidine-1-carbonyl]-1-hydroxy-cyclohexyl}-(3,4-dimethyl-phenyl)-methanone | solid |
| 70 | ex. 10/ HN(CH₃)—(CH₂)₂—NH(CH₃) | 2-hydroxy-2-(4-methoxy-benzoyl)-cyclohexane-carboxylic acid (2-{[2-hydroxy-2-(4-methoxy-benzoyl)-cyclohexanecarbonyl]-methyl-amino}-ethyl)-methyl-amide | 237-240 |

TABLE 8-continued

| ex. | lactone/diamine | structure and name | mp [°C.] |
|---|---|---|---|
| 71 | ex. 10/ O—(CH₂)₂—NH₂ (CH₂)₂ O—(CH₂)₂—NH₂ | 2-hydroxy-2-(4-methoxy-benzoyl)-cyclohexane-carboxylic acid {2-[2-(2-{[2-hydroxy-2-(4-methoxy-benzoyl)-cyclohexanecarbonyl]-amino}-ethoxy)-ethoxy]-ethyl}-amide | resin |
| 72 | ex. 10/ HN⟨piperidine⟩—(CH₂)₃—⟨piperidine⟩NH | {2-[4-(3-{1-[2-hydroxy-2-(4-methoxy-benzoyl)-cyclo-hexanecarbonyl]-piperidin-4-yl}-propyl)-piperidine-1-carbonyl]-1-hydroxy-cyclohexyl}-(4-methoxy-phenyl)-methanone | foam |
| 73 | ex. 10/ HN⟨piperazine⟩NH | {4-[2-hydroxy-2-(4-methoxy-benzoyl)-cyclohexanecarbonyl]-piperazin-1-yl}-[2-hydroxy-2-(4-methoxy-benzoyl)-cyclohexyl]-methanone | 238-240 |
| 74 | ex. 10/ H₂N—CH₂—⟨cyclohexane⟩—CH₂—NH₂ | 2-hydroxy-2-(4-methoxy-benzoyl)-cyclohexane-carboxylic acid [3-({[2-hydroxy-2-(4-methoxy-benzoyl)-cyclohexanecarbonyl]-amino}-methyl)-cyclohexylmethyl]-amide | solid |
| 75 | ex. 10/ NH₂(CH₂)₃Si(CH₃)₂—O—Si(CH₃)₂(CH₂)₃NH₂ | 2-hydroxy-2-(4-methoxy-benzoyl)-cyclohexane-carboxylic acid {3-[3-(3-{[2-hydroxy-2-(4-methoxy-benzoyl)-cyclohexanecarbonyl]-amino}-propyl)-1,1,3,3-tetramethyl-disiloxanyl]-propyl}-amide | resin |

EXAMPLE 76

2-Hydroxy-2-(4-methoxy-benzoyl)-cyclohexanecarboxylic acid 3-(diethoxyhydroxy-silanyl)propyl-amide

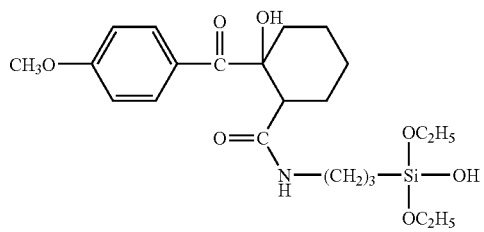

6.96 g (0.025 mol) of 2-hydroxy-2-(4-methoxy-benzoyl)-cyclohexanecarboxylic acid (prepared according to example 6) are added to a solution of 5.5 g (0.025 mol) of 3-aminopropyltriethoxysilane in 50 ml ethanol. The reaction mixture is stirred at room temperature for 2 hours before the solvent is evaporated in vacuum, providing 11 g of a colorless viscous resin. $^1$H-NMR analysis of the product indicates the structure of 2-hydroxy-2-(4-methoxy-benzoyl)-cyclohexanecarboxylic acid 3-(diethoxy-hydroxy-silanyl)propyl-amide for the product.

$^1$H-NMR (CDCl$_3$), δ [ppm]: 8.30 (dxd, 2 aromt H); 7.53 (broad s, OH); 6.84 (dxd, 2 aromat H);): 3.83 (s, 3H, CH$_3$O); 3.74 (q, 4H, —Si—O—CH$_2$—CH$_3$); 2.9-2.6 (3H, —NH—CH$_2$— and H—C(1)); 2.19-1.5 (m, 12H); 1.18 (t, 3H, —Si—CH$_2$—CH$_3$).

EXAMPLE 77

2-Hydroxy-2-(4-methoxy-benzoyl)-cyclohexanecarboxylic acid 2-methylpropyl-amide

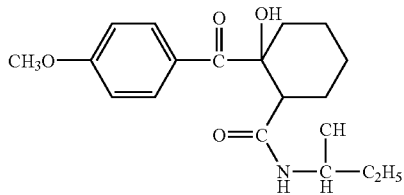

20.8 g (0.08 mol) of 6-(4-methoxy-benzoyl)-7-oxa-bicyclo[4.2.0]octan-8-one (compound of example 10) are dissolved in 270 ml of tert-butyl methyl ether. 10.46 g (0.143 mol) of sec-butylamine are slowly added to this solution over one hour. The reaction mixture is stirred for 24 hours at room temperature. After this time, $^1$H-NMR analysis shows that the reaction mixture consists of 60% starting material and 40% of the product. Another 10.46 g (0.143 mol) of sec-butylamine are added and the reaction mixture is stirred for another four hours at room temperature. After that time the solvent is partially distilled off and substituted by the slow addition of 50 ml heptane. The precipitation formed is collected and the remaining liquid further diluted with hexane, resulting in the formation of an additional precipitation. The solids are collected and washed with hexane to give a white powder that according to $^1$H-NMR analysis consists of 64% product and 36% of the starting material. These compounds are separated by flash chromatography on silicagel (eluent: toluene/ethyl acetate 9:1), providing 2-hydroxy-2-(4-methoxy-benzoyl)-cyclohexanecarboxylic acid 2-methyl-propyl-amide as a colorless solid with a melting point of 143-147° C.

$^1$H-NMR (CDCl$_3$), δ [ppm]: 8.28 (dxd, 2 aromt H); 6.87 (dxd, 2 aromat H); 6.06 (broad s, OH); 5.48 (broad d, NH): 3.85 (s, 3H, CH$_3$O); 3.78 (qxt, 1H, —NH—CH(CH$_3$)—); 2.83 (1H, dxd, H—C(1)); 2.17 (br d, 1H); 2.10-1.2 (m, 9H); 1.08 (d, 3H, —NH—CH(CH$_3$)—); 0.85 (t, 3H, —CH$_2$—CH$_3$).

EXAMPLE 78

Curing of Acrylic Coatings Under UV-A Irradiation

A photocurable composition is prepared by mixing the following ingredients:

| % by weight | Products | Description | Supplier |
|---|---|---|---|
| 94.5 | Desmolux ® VP LS 2308 | aliphatic urethane acrylate approx. 80% in hexandiol diacrylate (HDDA) | Bayer Material Science |
| 5.0 | HDDA | Reactive diluent | Cytec Surface Specialties |
| 0.5 | BYK ® 306 | Levelling agent | Byk Additives & Instruments |

3% by weight of the photoinitiator compound is added to the formulation well dissolved by stirring at 40° C. for 1 hour. Individual paint samples are prepared using photoinitiator of examples 1; 2; 3; 4; 5; 7; 15; 16; 17; 18; 19; 20; 21; 22; 27; 30; 31; 32; 33; 34; 35; 36; 37; 38; 39; 40, 41; 42; 44; 45; 48; 51; 54; 55; 56; 57; 58; 59; 61; 64; 65; 66; 67; 70; 72; 73. The cold formulation containing photoinitiator is then applied on a white coil coat aluminum panel to achieve a dry film thickness of 35 μm. Samples are exposed to UVA-light for 5 minutes using a Panacol F-450 lamp with a black light filter with a distance of 20 cm between substrate and lamp. The successful curing of the paint samples is tested by dry rub test. By this method a tissue is manually rubbed over the irradiated paint sample. If the paint is cured, the film is solid and cannot be removed from the panel.

All paint samples are cured after irradiation with UV-A light.

EXAMPLE 79

Curing of Acrylic Coatings in the Presences of Light Stabilizers Using UV-A Irradiation The following paint formulation is prepared:

| % by weight | Product | Description | Supplier |
|---|---|---|---|
| 92.2 | DESMOLUX VP LS 2308 | aliphatic urethane acrylate approx. 80% in HDDA | Bayer Material Science |
| 4.9 | HDDA | acrylic monomer | Cytec Surface Specialties |
| 0.5 | BYK ® 306 | slip and levelling Agent | BYK Additives & Instruments |
| 1.5 | TINUVIN ® 400 | UV-absorber | Ciba Inc. |
| 1.0 | TINUVIN ® 158 | hindered amine light stabilizer | Ciba Inc. |

3% by weight of the photoinitiator compound is added to the formulation well dissolved by stirring at 40° C. for 1 hour. Individual paint samples are prepared using photoinitiator of examples 2; 3; 41; 58; 63. The cold formulation is then applied on a white pre-coated aluminum panel to achieve a dry film thickness of 35 μm. Another sample is prepared by applying the paint sample onto polyester film. Both samples are exposed to UVA-light for 5 minutes using a Panacol F-450 Lamp with a black light filter with a distance of 20 cm between substrate and lamp.

Pendulum Hardness according to Koenig is measured on the samples painted onto metal substrate and given in [s].

The coated film is peeled off from the polyester film to measure the double bond conversion (DBC) on the top surface and the film bottom of the coating using AT-IR spectroscopy. The reaction extent is followed by monitoring the acrylate double bond at 810 cm$^{-1}$. The reference peak is assigned to the —CH— peak at 1525 cm$^{-1}$. The double bond conversion is calculated in % in reference to the liquid, unirradiated sample. The results are shown in following table 9.

TABLE 9

| | photoinitiator | | | | |
|---|---|---|---|---|---|
| | of Ex. 2 | of Ex. 3 | of Ex. 41 | of Ex. 58 | of Ex. 63 |
| DBC Top [%] | 76 | 73 | 76 | 84 | 84 |
| DBC Bottom [%] | 88 | 89 | 89 | 91 | 90 |
| Pendulum Hardness [s] | 139 | 125 | 96 | 139 | 143 |

EXAMPLE 80

Curing of Acrylic Coatings Under Conventional UV-Light

A UV-curable paint is prepared using the following formulation:

| % by weight | Component | Description | Supplier |
|---|---|---|---|
| 89.0 | Ebecryl 604 | unsaturated epoxy-acrylate approx. 80% in HDDA | Cytec Surface Specialties |
| 10.0 | SR 344 | polyethylene Glycol (400) diacrylate | Sartomer |
| 1.0 | Ebecryl 350 | unsaturated silicone acrylate | Cytec Surface Specialties |

3% by weight of the photoinitiator compound is added to the formulation well dissolved by stirring at 50° C. for 1 hour. Individual paint samples are prepared using photoinitiator of examples 3; 37; 38; 41; 45; 58; 63. The cold paint samples are applied onto white pre-coated aluminum panels to achieve a dry film thickness of 35-40 μm and cured using UV-curing lab equipment by IST GmbH equipped with 2 Hg bulbs at 100 W/cm and a line speed of 10 m/min. After curing pendulum hardness according to Koenig is measured and given in s. The results are presented in following table 10.

TABLE 10

| | photoinitiator | | | | | | |
|---|---|---|---|---|---|---|---|
| | of Ex. 3 | of Ex. 37 | of Ex. 38 | of Ex. 41 | of Ex. 45 | of Ex. 58 | of Ex. 63 |
| Pendulum Hardness [s] | 196 | 193 | 189 | 183 | 197 | 196 | 190 |

EXAMPLE 81

Curing of Acrylic Coatings Under UV-A Fluorescent Lamps

2 UV-curable formulations as described in example 77 and 78 are prepared. Individual paint samples are prepared using the photoinitiator compounds according to example 58. 3% by weight of photoinitiator is added to the formulation and well dissolved by stirring at 40° C. for 1 hour. The cold formulation containing photoinitiator is then applied on a white coil coat aluminum panel to achieve a dry film thickness of 35 μm. For irradiation, the samples are placed under 5 fluorescent light bulbs at a distance of 20 cm. Two different types of lamps are used individually. The first sample is irradiated for 25 min using Philips TL-K 40W Actinice BL, with an emission peak at 365 nm, the second is irradiated for 60 min using custom made 40W lamps with an emission peak at 340 nm. The successful curing is determined by dry rub test as described above.

Both samples are cured after irradiation.

EXAMPLE 82

Curing of Unsaturated Polyester

A formulation based on unsaturated polyester in styrene is prepared by mixing the following ingredients:

| % by weight | Product | Description | Supplier |
|---|---|---|---|
| 99.5 | Roskydal ® 502 | Unsaturated polyester approx. 66% in styrene | Bayer Material Science |
| 0.5 | Byk ® 300 | Slip and levelling agent | Byk Additives & Instruments |

3% by weight of the photoinitiator compound of example 58 is added and well dissolved by stirring for 60 min at 40° C. The cold paint is applied onto white pre-coated aluminum panels to achieve a dry film thickness of about 35 μm and irradiated on IST laboratory UV-curing equipment using 2 Hg-bulbs at 100 W/cm and a line speed of 10 m/min. The successful curing is determined by dry rub test as described above.

The sample is cured after irradiation.

EXAMPLE 83

Curing of Water Borne UV-Curable Formulation

A water dilutable UV-curable paint is prepared using following formulation:

| % by weight | Product | Description | Supplier |
|---|---|---|---|
| 99.3 | Bayhydrol UV 2282 | water dilutable UV-curable polyurethane dispersion (approx. 39% in water) | Bayer Material Science |
| 0.4 | Byk ® 347 | slip and levelling agent | Byk Additives & Instruments |
| 0.3 | Borchi ® Gel L 75 N | thickener for water borne coatings | Borchers GmbH |

1.25% of photoinitiator is added to the formulation and dissolved by stirring at room temperature. Individual paint samples are prepared using photoinitiator compounds as described in examples 20; 21; 29; 30. The paint is applied onto white pre-coated aluminum panels to achieve a dry film thickness of approx. 35 μm. Samples are cured by first drying-off water in a convection oven for 10 min at 60° C. and then by irradiation on laboratory UV-curing equipment by IST GmbH using 2 Hg bulbs at 100 W/cm and a line speed of 5 m/min. The double bond conversion (DBC) is determined by AT-IR spectroscopy of the paint surface. The reaction extent is followed by monitoring the acrylate double bond at 810 cm$^{-1}$. The reference peak is assigned to the —CH— peak at 2900 cm$^{-1}$. The double bond conversion is calculated in % in reference to the dried but unirradiated sample. The results are shown in following table 11.

TABLE 11

| | photoinitiator | | | |
|---|---|---|---|---|
| | of Ex. 20 | of Ex. 21 | of Ex. 29 | of Ex. 32 |
| DBC Top [%] | 76 | 79 | 81 | 80 |

The invention claimed is:
1. Compounds of the formula I'

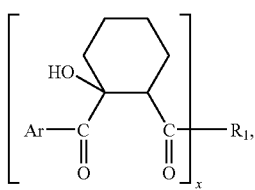

(I')

wherein
x is an integer from 1-4;
Ar is phenyl, naphthyl, anthryl or phenanthryl each of which optionally is substituted by one or more CN, OR$_5$, C$_3$-C$_5$alkenyl or C$_1$-C$_6$alkyl which optionally is substituted by one or more OR$_6$, COOR$_6$ or halogen;
R$_1$ when x is 1, is OR$_7$, O$^-$X$^+$, NR$_8$R$_9$, C$_1$-C$_{20}$alkyl optionally substituted by one or more COOR$_{10}$, or is C$_2$-C$_5$alkenyl or phenyl-C$_1$-C$_4$alkyl;
R$_1$ when x is 2, is C$_1$-C$_{20}$alkylene, C$_2$-C$_{20}$alkylene which optionally is interrupted by one or more O, or is O-A-O, O-A-NR$_{15}$, NR$_{15}$-A-O, NR'$_{15}$-A-NR$_{15}$, NR$_{15a}$-A$_1$-NR$_{15b}$ or NR'$_{15}$—(CH$_2$)$_{x'}$-A-(CH$_2$)$_{x'}$—NR$_{15}$ or is O$^-$X$^{2+}$O$^-$;
x' is an integer from 1-4;
R$_1$ when x is 3, is N(R$_{30}$O)$_3$—; C$_3$-C$_{20}$alkanetriyltrioxy which optionally is substituted by OH; C$_3$-C$_{20}$alkanetriyltriamino; a trivalent siloxane, or O$_3^-$X$^{3+}$;
R$_1$ when x is 4, is C$_4$-C$_{20}$alkanetetrayltetraoxy optionally substituted by OH; C$_4$-C$_{20}$alkanetetrayltetraamino; a tetravalent siloxane; or O$_4^-$X$^{4+}$;
R$_5$ is hydrogen, C$_1$-C$_4$alkyl, phenyl which optionally is substituted by one or more C$_1$-C$_4$alkyl, C$_1$-C$_4$alkoxy or halogen; or is (C$_2$-C$_6$alkyleneO)$_n$—R$_6$;
n is an integer from 1-20;
R$_6$ is hydrogen, C$_1$-C$_4$alkyl, C$_2$-C$_5$alkenyl or C$_2$-C$_6$alkanoyl;
R$_7$ is hydrogen, C$_2$-C$_5$alkenyl, C$_2$-C$_{20}$alkyl which is substituted by one or more OH, NR$_{11}$R$_{12}$ or Si(R$_{14}$)$_y$(OR$_{13}$)$_z$; or is C$_2$-C$_{20}$alkyl which is interrupted by one or more O or NR$_{15}$ and optionally is substituted by one or more OH, NR$_{11}$R$_{12}$ or Si(R$_{14}$)$_y$(OR$_{13}$)$_z$; or is C$_1$-C$_{20}$haloalkyl which optionally is substituted by one or more OH, NR$_{11}$R$_{12}$ or Si(R$_{14}$)$_y$(OR$_{13}$)$_z$; or is C$_2$-C$_{20}$haloalkyl which is interrupted by one or more O or NR$_{15}$;
R$_8$ and R$_9$ independently of one another are hydrogen, C$_1$-C$_{20}$alkyl; C$_1$-C$_8$alkyl substituted by CN, COOR$_{11}$ or Si(R$_{14}$)$_y$(OR$_{13}$)$_z$; C$_2$-C$_8$alkyl substituted by one or more NR$_{11}$R$_{12}$ or OR$_{11}$; or are C$_3$-C$_8$cycloalkyl, C$_3$-C$_5$alkenyl, phenyl-C$_1$-C$_4$alkyl or phenyl which optionally is substituted by C$_1$-C$_4$alkyl, OR$_{11}$ or halogen;
or R$_8$ and R$_9$ together are C$_3$-C$_7$alkylene which optionally is interrupted by one or more O or NR$_{15}$ and which C$_3$-C$_7$alkylene or interrupted C$_3$-C$_7$alkylene optionally is substituted by one or more C$_1$-C$_4$alkyl or COOR$_{11}$;
z is an integer from 0-3;
y is an integer from 0-3, wherein the sum of y+z is 3;
R$_{10}$ is hydrogen or C$_1$-C$_4$alkyl;
R$_{11}$ and R$_{12}$ independently of one another are hydrogen or C$_1$-C$_4$alkyl which optionally is substituted by OH;
R$_{13}$ is hydrogen, C$_1$-C$_4$alkyl or Si(R$_{14}$)(R'$_{14}$)(R''$_{14}$);
R$_{14}$, R'$_{14}$ and R''$_{14}$ independently of each other are hydrogen or C$_1$-C$_4$alkyl;
R$_{15}$ and R'$_{15}$ independently of one another are hydrogen; C$_1$-C$_{20}$alkyl which optionally is substituted by OH, COOR$_{11}$ or CN; or is C$_2$-C$_{20}$alkyl which optionally is interrupted by one or more O; or is C$_3$-C$_5$alkenyl, phenyl-C$_1$-C$_4$alkyl, C$_1$-C$_5$alkanoyl or benzoyl;
R$_{15a}$ and R$_{15b}$ independently of one another form an aliphatic ring with a carbon atom of A$_1$ or R$_{15a}$ and R$_{15b}$ together are C$_1$-C$_3$alkylene;
R$_{30}$ is C$_2$-C$_8$-alkylene optionally interrupted by one or more O;
A is C$_2$-C$_{20}$alkylene which optionally is interrupted by one or more O or NR$_{15}$; C$_2$-C$_{20}$haloalkylene which optionally is interrupted by one or more O or NR$_{15}$; C$_5$-C$_{20}$cycloalkylene; or A is a divalent siloxane
A$_1$ is C$_2$-C$_{20}$alkylene which optionally is interrupted by one or more O or NR$_{15}$; and
X is a x-valent cationic counter ion.
2. Compounds according to claim 1,
wherein
Ar is phenyl or naphthyl each of which optionally is substituted by one or more CN, OR$_5$,
C$_3$-C$_5$alkenyl or by C$_1$-C$_6$alkyl which optionally is substituted by one or more OR$_6$, COOR$_6$ or halogen; and
R$_1$, R$_5$, R$_6$ and x are as defined in claim 1.
3. Compounds according to claim 1, wherein
x is an integer from 1-4;
Ar is phenyl or phenyl which is substituted by one or more OR$_5$ or C$_1$-C$_6$alkyl which optionally is substituted by one or more OR$_6$ or COOR$_6$;

$R_1$ when x is 1, is $OR_7$, $O^-X^+$, $NR_8R_9$ or $C_1$-$C_{20}$alkyl;
$R_1$ when x is 2, is O-A-O, $NR'_{15}$-A-$NR_{15}$, $NR_{15a}$-$A_1$-$NR_{15b}$ or $NR'_{15}$—$(CH_2)_{x'}$-A-$(CH_2)_{x'}$—$NR_{15}$;
x' is an integer from 1-4;
$R_1$ when x is 3, is $N(R_{30}O)_3$–;
$R_1$ when x is 4, is a tetravalent siloxane of the formula XII

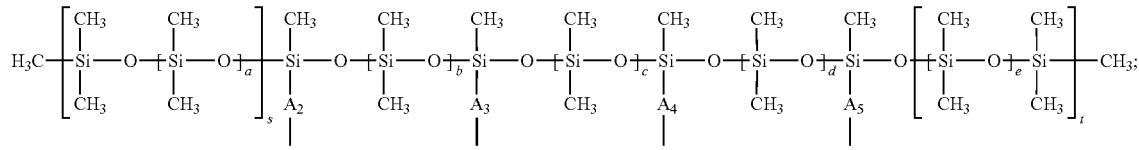

$A_2$, $A_3$, $A_4$ and $A_5$ are $C_1$-$C_{10}$alkylene which optionally is substituted by $[O(CH_2)_g—O]_h$;
g is 2;
h is 1;
a is 0
b, c, d, e, s and t are 1;
$R_5$ is $C_1$-$C_4$alkyl;
$R_6$ is hydrogen;
$R_7$ is hydrogen, $C_2$-$C_{20}$alkyl which is substituted by OH; or is $C_2$-$C_{20}$alkyl which is interrupted by one or more O and optionally is substituted by OH; or is $C_1$-$C_{20}$haloalkyl which optionally is substituted by OH;
$R_8$ and $R_9$ independently of one another are hydrogen, $C_1$-$C_{20}$alkyl; $C_1$-$C_5$alkyl substituted by $Si(R_{14})_y(OR_{13})_z$;
or $R_8$ and $R_9$ together are $C_3$-$C_7$alkylene which optionally is substituted by $COOR_{11}$;
z is an integer from 0-3;
y is an integer from 0-3, wherein the sum of y+z is 3;
$R_{11}$ and $R_{13}$ are $C_1$-$C_4$alkyl;
$R_{14}$ is $C_1$-$C_4$alkyl;
$R_{15}$ and $R'_{15}$ are hydrogen or $C_1$-$C_{20}$alkyl;
$R_{15a}$ and $R_{15b}$ independently of one another form an aliphatic ring with a carbon atom of $A_1$ or $R_{15a}$ and $R_{15b}$ together are $C_1$-$C_3$alkylene;
$R_{30}$ is $C_2$-$C_5$-alkylene;
A is $C_2$-$C_{20}$alkylene which optionally is interrupted by one or more O; $C_2$-$C_{20}$haloalkylene; $C_5$-$C_{20}$cycloalkylene; or is a divalent siloxane of the formula X

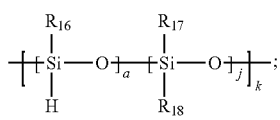

a is 0;
j is 1;
k is 2; and
$R_{16}$ $R_{17}$ and $R_{18}$ are $C_1$-$C_{18}$alkyl;
$A_1$ is $C_2$-$C_{20}$alkylene; and
X is $NR_{22}R_{23}R_{24}R_{25}$;
$R_{22}$, $R_{23}$, $R_{24}$, $R_{25}$ independently of one another are hydrogen; or $C_1$-$C_{20}$alkyl which optionally is substituted by OH, $NR_{26}R_{27}$, benzoyl or $Si(OH)_y(OC_1$-$C_4alkyl)_z$;
or two of $R_{22}$, $R_{23}$, $R_{24}$ or $R_{25}$ together form a 6-membered saturated ring which optionally includes O as additional heteroatom; and $R_{26}$ and $R_{27}$ are hydrogen or $C_1$-$C_4$alkyl which optionally is substituted by OH.

4. Process for the preparation of compounds of the formula (I') comprising a step of reacting a compound of the formula (F)

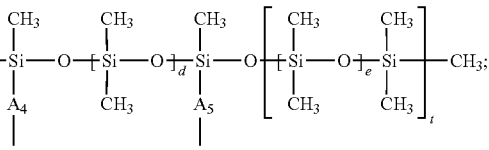

with $R_1(H)_x$, wherein
p is an integer from 1-3;
q is an integer from 0-3;
$R_2$ and $R_3$ independently of one another are hydrogen or $C_1$-$C_5$alkyl, or $R_2$ and $R_3$ together are O, $C_1$-$C_3$alkylene or CH=CH;
$R_4$ is $C_1$-$C_4$alkyl;
Ar, $R_1$ and x are as defined in claim 1.

5. Compounds of the formula (F)

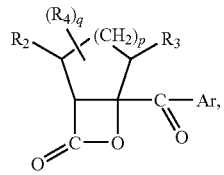

wherein
p is an integer from 1-3;
q is an integer from 0-3;
Ar is phenyl, naphthyl, anthryl or phenanthryl each of which optionally is substituted by one or more $C_1$, CN, $OR_5$, $C_3$-$C_5$alkenyl or $C_1$-$C_6$alkyl which optionally is substituted by one or more $OR_6$, $COOR_6$ or halogen;
$R_2$ and $R_3$ independently of one another are hydrogen or $C_1$-$C_5$alkyl, or $R_2$ and $R_3$ together are O, $C_1$-$C_3$alkylene or CH=CH;
$R_4$ is $C_1$-$C_4$alkyl;
$R_5$ is hydrogen, $C_1$-$C_4$alkyl, phenyl which optionally is substituted by one or more $C_1$-$C_4$alkyl, $C_1$-$C_4$alkoxy or halogen; or is $(C_2$-$C_6alkyleneO)_n$—$R_6$;
n is an integer from 1-20; and
$R_6$ is hydrogen, $C_1$-$C_4$alkyl, $C_2$-$C_5$alkenyl or $C_2$-$C_6$alkanoyl.

6. A photopolymerizable composition comprising
(a) at least one ethylenically unsaturated compound; and
(b) at least one photoinitiator compound of the formula (I') according to claim 1.

7. A photopolymerizable composition according to claim 6, comprising, in addition to components (a) and (b), further photoinitiators (c) and/or further additives (d).

8. A process for the photopolymerization of monomeric, oligomeric or polymeric compounds having at least one ethylenically unsaturated double bond, which comprises irradiating a composition according to claim 6 with light in the range from 150 to 600 nm.

9. A process according to claim 8 for the preparation of pigmented and nonpigmented surface coatings, printing inks, screen printing inks, offset printing inks, flexographic printing inks, ink jet printing inks, overprint varnishes, powder coatings, printing plates, adhesives, pressure-sensitive adhesives, dental materials, optical waveguides, optical switches, colour testing systems, composite materials, gel coats, glass-fibre cable coatings, screen printing stencils, resist materials, resist materials for printed circuit board production, primary imaging resist and solder resist, colour filters, resist materials for plasma display panel production, for the encapsulation of electrical and electronic components, for the preparation of magnetic recording materials, for the preparation of three-dimensional objects by means of stereolithography, of photographic reproductions, image recording material, for holographic recordings, for the preparation of decolouring materials, for the preparation of image recording materials using microcapsules.

10. A coate substrate which has been coated on at least one surface with a composition according to claim 6.

11. A process for the photographic production of relief images in which a coated substrate according to claim 10 is subjected to imagewise exposure and then the unexposed portions are removed with a solvent.

12. A composition according to claim 6, which is a dual curable coating composition, comprising
  (a) at least one ethylenically unsaturated compound;
  (b) at least one compound of the (I'), as defined in claim 1, as photoinitiator
  (f) a thermal crosslinkable compound.

13. A composition according to claim 6, which is a double (thermal and UV) curable coating composition, comprising
  (a) at least an ethylenically unsaturated compound;
  (b) at least one compound of the formula (I'), as defined in claim 1, as UV-photoinitiator effective to enable UV-curing of the ethylenically unsaturated compound; and
  (g) at least one thermal radical initiator effective to enable IR-curing or NIR-curing or to enable the convection heat curing of the ethylenically unsaturated compound.

* * * * *